US008642088B2

(12) United States Patent
Reed et al.

(10) Patent No.: US 8,642,088 B2
(45) Date of Patent: Feb. 4, 2014

(54) TANNIN-CHITOSAN COMPOSITES

(75) Inventors: Jess Dreher Reed, Middleton, WI (US); Christian Gerald Krueger, Cambridge, WI (US); Sergio Madrigal-Carballo, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 65 days.

(21) Appl. No.: 12/875,820

(22) Filed: Sep. 3, 2010

(65) Prior Publication Data

US 2011/0059162 A1    Mar. 10, 2011

Related U.S. Application Data

(60) Provisional application No. 61/240,033, filed on Sep. 4, 2009.

(51) Int. Cl.
*A61K 47/36* (2006.01)
*A61K 31/722* (2006.01)
*A61F 13/00* (2006.01)
*C08H 7/00* (2011.01)

(52) U.S. Cl.
CPC ............... *A61K 47/36* (2013.01); *A61K 31/722* (2013.01); *A61F 2013/00523* (2013.01); *A61F 2013/00676* (2013.01); *A23V 2250/21166* (2013.01); *C08H 6/00* (2013.01)
USPC ............................................ 424/488; 514/55

(58) Field of Classification Search
None
See application file for complete search history.

(56) References Cited

U.S. PATENT DOCUMENTS

| | | | |
|---|---|---|---|
| 4,090,919 | A | 5/1978 | Chibata et al. |
| 5,153,281 | A | 10/1992 | Shimizu et al. |
| 6,020,422 | A | 2/2000 | Connors et al. |
| 6,780,504 | B2 | 8/2004 | Rupprecht et al. |
| 6,960,617 | B2 | 11/2005 | Omidian et al. |
| 7,122,574 | B2 | 10/2006 | Romanczyk, Jr. et al. |
| 7,288,532 | B1 | 10/2007 | Payne et al. |
| 7,482,503 | B2 | 1/2009 | Gregory et al. |
| 7,767,235 | B2 | 8/2010 | Shrikhande et al. |
| 2001/0051189 | A1* | 12/2001 | Alonso Fernandez et al. ............................. 424/499 |
| 2003/0232895 | A1* | 12/2003 | Omidian et al. ................ 521/99 |
| 2004/0151778 | A1 | 8/2004 | Richard et al. |
| 2005/0150489 | A1* | 7/2005 | Dunfield et al. ......... 128/200.14 |
| 2005/0281886 | A1* | 12/2005 | Cattaneo ...................... 424/490 |
| 2007/0071871 | A1* | 3/2007 | Shrikhande et al. .......... 426/599 |
| 2007/0292539 | A1* | 12/2007 | Vorsa et al. ................... 424/732 |
| 2008/0095810 | A1* | 4/2008 | Alonso Fernandez et al. ............................. 424/401 |
| 2008/0286254 | A1 | 11/2008 | Sakamoto et al. |
| 2009/0035440 | A1 | 2/2009 | Velikov |

FOREIGN PATENT DOCUMENTS

| | | |
|---|---|---|
| DE | 4141889 | 6/1993 |
| EP | 507272 | 10/1992 |
| EP | 1304346 | 4/2003 |
| JP | 4308525 | 10/1992 |
| JP | 7236419 | 9/1995 |
| JP | 11057314 | 3/1999 |
| JP | 2001335698 | 12/2001 |
| JP | 2004026785 | 1/2004 |
| WO | WO 99/04764 | 2/1999 |
| WO | WO 03/091237 | 11/2003 |

OTHER PUBLICATIONS

N Aelenei, MI Popa, O Novac, G Lisa, L Balatia. "Tannic acid incorporation in chitosan-based microparticles and in vitro controlled release." Journal of Materials Sciece: Materials in Medicine, vol. 20, 2009, pp. 1095-1102.*

AP Kulkarni, HS Mahal, S Kapoor, SM Aradhya. "In Vitro Studies on the Binding, Antioxidant, and Cytotoxic Actions of Punicalagin." Journal of Agricultural and Food Chemistry, vol. 55, 2007, pp. 1491-1500.*

CC Neto, CG Krueger, TL Lamoureaux, M Kondo, AJ Vaisberg, RAR Hurta, S Curtis, MD Matchett, H Yeung, MI Sweeney, JD Reed. "MALDI-TOF MS characterization of proanthocyanidins from cranberry fruit (*Vaccinium macrocarpon*) that inhibit tumor cell growth and matrix metalloproteinase expression in vitro." J. Sci. Food Agric, vol. 86, 2006, pp. 18-25.*

MNV Ravi Kumar, RAA Muzzarelli, C Muzzarelli, H Sashiwa, AJ Domb. "Chitosan Chemistry and Pharmaceutical Perspectives." Chemical Reviews, vol. 104, 2004, pp. 6017-6084.*

JF Grcic, NS Basnet, I Jalsenjak. "Mucoadhesive Chitosan-Coated Liposomes: Characteristics and Stability." Journal of Microencapsulation, vol. 18 No. 1, 2001, pp. 3-12.*

Madrigal-Carballo et al. 2009. Chitosomes loaded with cranberry proanthocyanidins attenuate the bacterial lipopolysaccharide-induced expression of iNOS and COX-2 in raw 264.7 macrophages. *J. Liposome Res.* 19(3): 189-196.

(Continued)

*Primary Examiner* — Frederick Krass
*Assistant Examiner* — Issac Shomer
(74) *Attorney, Agent, or Firm* — Michael H. Haukaas, Esq.

(57) ABSTRACT

The invention provides a composition comprising a matrix of chitosan and a tannin wherein the chitosan is electrostatically bonded to the tannin to form a chitosan-tannin composite material. The chitosan can be partially or fully deacetylated, and the tannin can be a monomeric or an oligomeric proanthocyanidin or a hydrolysable tannin. The chitosan-tannin composite material can be a nanoparticle, a hydrogel film, a bio-foam, or a biogel, or the chitosan-tannin composite material can coat a liposome. The composite materials can be used for drug delivery, for antibacterial and/or antifungal applications, for tissue engineering applications, for wound healing applications, or they can be used as adjuvants for vaccination, including oral vaccinations. The invention also provides methods of preparing the composite materials and their various forms.

9 Claims, 30 Drawing Sheets

(56) References Cited

OTHER PUBLICATIONS

Beecher, Proceedings of the Third International Scientific Symposium on Tea and Human Health: Role of Flavonoids in the Diet, J. Nutrition 2003, pp. 3248S-3254S.

Kumar, Ravi et al. 2004. Chitosan chemistry and pharmaceutical perspectives. Chemical Reviews. 104:6017-6084.

Reed J.D. et al. 2005. MALDI-TOF Mass spectrometry of oligomeric food polyphenols. Phytochem. 66(18): 2248-2263.

Krueger, C.G. et al. Matrix-assisted laser desorption/ionization time-of-flight mass spectrometry of heteropolyflavan-3-ols and glucosylated heteropolyflavans in sorghum [*Sorghum bicolor* (L.) Moench)]. J. Agric. Food Chem. 2003. 53, 538-543.

Krueger, C.G. et al. Matrix-assisted laser desorption/Ionization time-of-flight mass spectrometry of anthocyanin-polyflavan-3-ol polymers in cranberry fruit [*Vaccinium macrocarpon*, Ait.] and spray dried cranberry juice. ACS Symposium, Uncovering the Mysteries of Red Wine Pigments. vol. 886: pp. 232-246. 2004.

Krueger, C.G. et al. 2000. Matrix-assisted laser desorption/ionization time-of-flight mass spectrometry of polygalloyl polyflavan-3-ols in grape seed extract. J Agric. Food Chem. 48: 1663-1667.

Aelenei et al., Tannic Acid Incorporation in Chitosan-Based Microparticles and in Vitro Controlled Release, J Mater Sci: Mater Med (2009) 20:1095-1102.

Rinaudo, M. 2006. Chitin and chitosan: Properties and applications. Progress in Polymer Science. 31:603-632.

Garlea et al., Chitosan-Polyphenols Nanostructured Matrices Drug Release Kinetics Studies, Analele Stiintifice ale Universitatii "Al. I. Cuza" din Iaşi (Serie Noua), Tomul IV, Biofizica, Fizica Medicala, Fizica Mediului, (2008), pp. 25-30, ISSN 1841-5318.

Hedqvist et al., Characterisation of Tannins and In Vitro Protein Digestibility of Several *Lotus corniculatus* Varieties, Animal Feed Science and Technology 87 (2000) 41-56.

Kim et al., Chitosan/Gelatin-Based Films Crosslinked by Proanthocyanidin, Wiley InterScience (www.interscience.wiley.com) Jul. 26, 2005, pp. 442-450. DOI: 10.1002/jbm.b.30324.

Roussy et al., Treatment of Ink-Containing Wastewater by Coagulation/Flocculation Using Biopolymers, Water SA vol. 31 No. 3 (http://www.wrc.org.za) Jul. 2005, pp. 369-376. ISSN 0378-4738.

Quideau et al., Ellagitannin Chemistry, Chemical Reviews, 1996, vol. 96, No. 1, pp. 475-503.

Zhang et al., Biopolymeric Delivery System for Controlled Release of Polyphenolic Antioxidants, European Polymer Journal 43 (2007) 2956-2966.

Zhu et al., Rapid Identification of Gallotannins from Chinese Galls by Matrix-Assisted Laser Desorption/Ionization Time-of-Flight Quadrupole Ion Trap Mass Spectrometry, Rapid Commun. Mass Spectrom. 2009; 23: 1678-1682.

Kim et al., "Chitosan/Gelatin-Based Films Crosslinked by Proanthocyanidin," Wiley InterScience [www.interscience.wiley.com] (Jul. 26, 2005) pp. 442-450.

\* cited by examiner

TANNIN-CHITOSAN COMPOSITES

RELATED APPLICATIONS

This application claims priority under 35 U.S.C. §119(e) to U.S. Provisional Patent Application No. 61/240,033, filed Sep. 4, 2009, which is incorporated herein by reference.

GOVERNMENT SUPPORT

This invention was made with government support under Grant No. AT003846 awarded by the National Institutes of Health. The United States Government has certain rights in the invention.

BACKGROUND OF THE INVENTION

Natural polymers have been used in many pharmaceutical applications and medical device technologies. One natural polymer, chitosan, has been used for the preparation of nanoparticles, microspheres, hydrogels, films, fibers, and tablets. Chitosan has been used to prepare potential drug delivery systems such as oral, nasal, parenteral, transdermal and ophthalmic formulations. Chitosan has also been used to prepare wound dressings and tissue scaffolds (Kumar et al., *Chem. Rev.* 2004, 104, 6017-6084). However, chitosan formulations and materials suffer from numerous drawbacks including limited stability, biodegradability and tensile strength. Materials such as modified chitosan and synthetic composite materials have tested for many of the same uses for which chitosan has been evaluated but many of these materials suffer from similar drawbacks, including insufficient biocompatibility.

Accordingly, there is a need for new materials that are biocompatible and biodegradable, and that have suitable stability and mechanical properties for use in human and other mammalian treatments and therapies. These new materials and compositions would preferably have advantages over chitosan alone, such as additional and/or improved antimicrobial and antifungal properties, and improved physical properties. The ability to use these materials as tissue scaffolds and/or systems for the delivery of therapeutic agents would further aid researchers in the areas of biomaterials and drug delivery.

SUMMARY

The invention provides biodegradable and biocompatible tannin-chitosan composites. The new composites can be formed into a variety of materials such as hydrogel films, three-dimensional foams, nanoparticles, and liposome coatings. The tannin-chitosan composite materials are stronger and have better mechanical properties than known chitosan materials. The tannin component of the composite adds antifungal, antibacterial, and antioxidant properties to the antimicrobial property of the chitosan component, thereby significantly increasing the effectiveness of the composite in therapeutic applications.

The invention therefore provides a composition comprising a matrix of chitosan and one or more tannins wherein the chitosan is electrostatically bonded to the tannins to form a chitosan-tannin composite material. The tannins can be at least dimeric in composition. For example, the tannins can be oligomeric proanthocyanidins or oligomeric hydrolysable tannins The compositions, or the tannins used to form the composition, can be substantially free or completely free of monomeric tannin components. The chitosan can have a deacetylation degree of about 80% to about 99%. The mean molecular weight of the chitosan can be about 170 kDa to about 400 kDa. In some embodiments, the mass of the tannins in the composite material can be about 1% to about 50% of the mass of the chitosan in the composite material. In some embodiments, the mass of the tannins is about 5% to about 30% of the mass of the chitosan.

By the selection of appropriate starting material (e.g., fruits, juice, presscake) and isolation procedures, the amount and proportion of tannins obtained with higher degrees of polymerization (DP) can be controlled. For example, tannins with DPs of greater than 2, 3, 4, 5, 6, 7, 8, 9, 10, 11, 12, or 13 can be isolated and used in the compositions described herein. Additionally, the tannins isolated can be biased or controlled in terms of the nature of interflavan linkages (A-type vs. B-type), as well as their structural heterogeneity.

In one embodiment, the tannin can be a proanthocyanidin (PA). The proanthocyanidin can have a degree of polymerization of at least, for example, 4, 5, 6, or 7. The proanthocyanidin can have at least one A-type interflavan bond. By the isolation processes described herein, proanthocyanidins with DPs of 2 to about 13, about 14 to about 20, about 2 to about 20, or about 8 to about 20, can be selectively isolated.

In another embodiment, the tannin can be a hydrolysable tannin (HT). In some embodiments, the hydrolysable tannin can include 2-5, 2-8, 2-10, or 2-12 glucose units in its core structure. The hydrolysable tannin can include punicalagin. In some embodiments, the hydrolysable tannin can include at least about 80%, at least about 85%, at least about 90%, or at least about 95% punicalagin or another specific tannin described herein.

The chitosan-tannin composition can be a nanoparticle, a hydrogel film, a bio-foam, or a biogel. Nanoparticles can be formulated into various therapeutic agent delivery systems, such as oral solutions, IV solutions, or aerosols. Films can be formed into wound healing or packaging materials. Foams can be used as scaffolds, such as for tissue engineering. The chitosan-tannin composition can also be used as a surface coating, for example, on the surface of a liposome.

The diameter of a chitosan-tannin composite material-coated liposome can be about 300 nm to about 800 nm. The chitosan-tannin composite material can form a nanoparticle that has a diameter of about 75 nm to about 450 nm, or about 100 nm to about 350 nm. In such embodiments, the nanoparticle can protect an encapsulated material in various environments, such as in the acidic conditions of the stomach. In some embodiments, the chitosan-tannin composite material can be crystalline.

The ratio of chitosan to tannins can be varied, in certain embodiments, from about 5:1 to about 1:5. The composite material can be optionally crosslinked. The amount of crosslinking agent used in preparing nanoparticles, with respect to the mass of chitosan, can be about 1:4 to about 1:25. Crosslinking agents that can be used include tripolyphosphate (TPP) anions, glutaraldehyde, glyoxal, sucrose, and the like.

The invention also provides a method for delivering a bioactive agent to a mammal comprising administering to a mammal a chitosan-tannin composite material described herein. The chitosan-tannin composite material can form a nanoparticle that encapsulates the bioactive agent, for example, a drug or nutrient. Examples of drugs and nutrients include lipids such as fatty acids, including omega-3 and omega-6 fatty acids, fat soluble vitamins (e.g., vitamin A, D, E, and/or K), antibiotics, probiotics, micronutrients such as β-carotene and/or ascorbic acid, proteins, and peptides. In some embodiments, monomeric tannins and other nutritional supplements can also be included in a chitosan-tannin composite matrix, or in a composition that includes a chitosan-tannin composite matrix.

The invention further provides methods to inhibit bacterial growth or fungi growth in an animal, a plant, food, or in vitro. The methods can include treatment of the animal, plant, or food, prophylactically or after colonization by bacteria or fungi, by administering an effective amount of a chitosan-tannin composite material described herein, wherein the composite material inhibits the bacterial growth or fungi growth. The bacteria or fungus can be any genera or species known to infect animals, plants, or food. The bacteria can be gram positive or gram negative bacteria. Examples of bacteria that can be killed or whose growth can be inhibited include bacteria of the genera *Escherichia, Erwinia,* or *Xanthomonas,* for example, *Escherichia coli, Erwinia carotovora* or *Xanthomonas* spp. Examples of fungi that can be killed or whose growth can be inhibited include fungus of the genera *Bothytis, Fusarium,* or *Colletotrichum,* for example, *Bothytis cines* or *Fusarium oxysporum,* or *Colletotrichum acutatum.*

The invention additionally provides an adjuvant for oral vaccination that includes a chitosan-tannin composite material as described herein, such as a nanoparticle, and an antigen. The adjuvant can be a protein, a peptide, a nucleic acid, or DNA. The antigen can be encapsulated in the nanoparticle or adsorbed to the surface of the nanoparticle. For example, the composite material can encapsulate the antigen and gradually release it under physiological conditions. The composite material can therefore protect an encapsulated antigen to allow for oral delivery. The composite material can also facilitate uptake by M cells in the nasal-associated lymphoid tissue (NALT) when administered nasally or by the M cells of the gut-associated lymphoid tissue (GALT) when administered orally, thus providing a vehicle for mucosal immunization.

The chitosan-tannin composite materials can be tailored to degrade over a range of rates under various conditions by varying the amounts of the components and methods for preparing the composite materials. Thus, the invention also provides a method of preparing a chitosan-tannin composite material. The invention further provides for the use of a composition described herein for the manufacture of medicaments useful for the treatment of conditions such as bacterial infection and/or fungal infection in a mammal, such as a human.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

FIG. 10 illustrates DSC thermograms of chitosan (dashed line) and tannin-chitosan composites (solid line).

DETAILED DESCRIPTION

Figure 1:
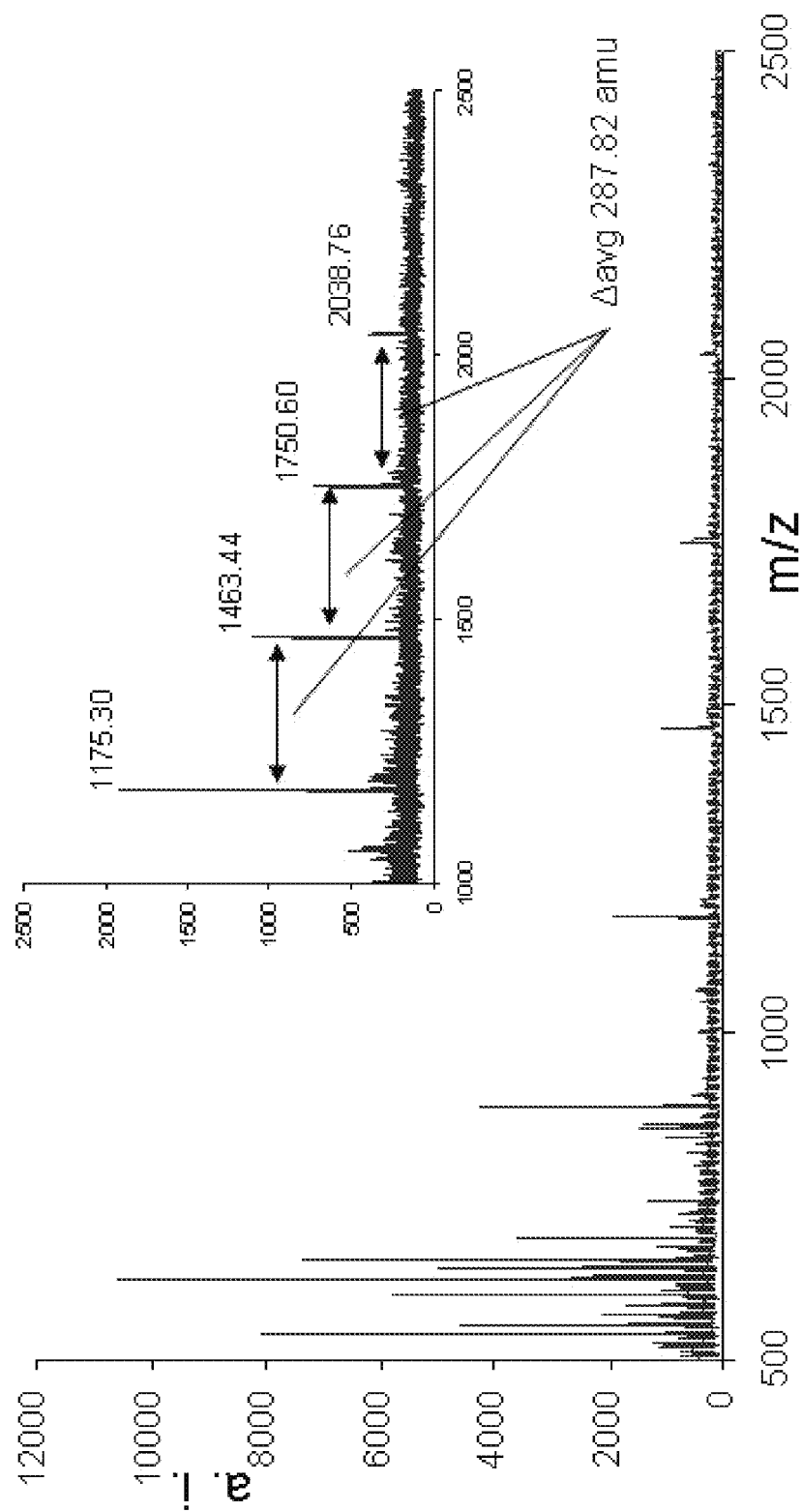
FIG. 1 illustrates a Matrix Assisted Laser Desorption/Ionization Time-of-Flight Mass Spectrometry (MALDI-TOF MS) spectrum in positive reflectron mode for the cranberry PA fraction. The section between m/z 1000 and 2500 has been amplified to identify the degree of polymerization, the nature of interflavan linkage and structural composition of subunits of oligomeric PA.

The invention provides new biodegradable, biocompatible composite materials comprising a combination of chitosan and tannins The chitosan-tannin composites are extremely versatile and can be formulated into various kinds of biomaterials, such as dermal patches, three-dimensional sponges for drug delivery and wound healing, biodegradable sutures, and scaffolds for cell proliferation in tissue engineering, as well as nanoparticles and liposomes for sustained drug delivery.

The chitosan-tannin composites can also be used in the formulation of vaccine antigens, including proteins, peptides, DNA, and the like. In these formulations, the antigen can be either entrapped or adsorbed onto the surface of the particles. The particles can also be tailored to degrade over a range of times, at various rates. They can therefore act as a depot from which the encapsulated antigen is gradually released. Additionally, chitosan-tannin nanoparticles can offer protection to encapsulated antigens delivered orally, as well as facilitate uptake by M cells in the nasal-associated lymphoid tissue (NALT) when administered nasally and M cells in the gut-associated lymphoid tissue (GALT) when administered orally, thus serving as a vehicle for mucosal immunization. Accordingly, chitosan-tannin complexes can be used in various important fields, such as environmental, drug delivery, tissue engineering, and other biomedical application.

Definitions

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", "an example embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect such aspect, feature, structure, moiety, or characteristic in connection with other embodiments, whether or not explicitly described.

The term "and/or" means any one of the items, any combination of the items, or all of the items with which this term is associated.

The singular forms "a," "an," and "the" include plural reference unless the context clearly dictates otherwise. Thus, for example, a reference to "a compound" includes a plurality of such compounds, so that a compound X includes a plurality of compounds X.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment. In addition, a recited range (e.g., weight percents, carbon groups, and the like) includes each specific value, integer, decimal, or identity within the range. Specific values listed herein for ranges and the like are for illustration only; they do not exclude other defined values or other values within defined ranges.

The phrase "one or more" is readily understood by one of skill in the art, particularly when read in context of its usage. For example, one or more substituents on a phenyl ring refers to one to five, or one to up to four, for example if the phenyl ring is disubstituted.

The term "contacting" refers to the act of touching, making contact, or of bringing to immediate or close proximity, including at the molecular level, for example, to bring about a chemical reaction or physical change, e.g., in a solution or other reaction mixture.

An "effective amount" generally means an amount which provides the desired effect. An effective amount therefore means a dosage sufficient to enhance the efficacy of treatment for a disease state or condition being treated. Thus the effective amount can vary depending on the patient, the disease, and the treatment being effected.

The term "patient" or "subject" refers to any animal, such as a mammal, including mice, rats, other rodents, rabbits, dogs, cats, swine, cattle, sheep, horses, or primates, and humans.

In reference to tannins, the phrase "substantially free of monomeric components" means that the tannins are at least dimeric in composition and few or no monomeric tannin species are present in the sample. For example, a tannin that is substantially free of monomeric components can include less than about 5 wt. % monomeric tannins, less than about 3 wt. % monomeric tannins, less than about 1 wt. % monomeric tannins, less than about 0.5 wt. % monomeric tannins, less than about 0.1 wt. % monomeric tannins, or no monomeric tannins. An example of a monomeric tannin is the compound tannic acid (pentagalloyl-D-glucose ($C_{76}H_{52}O_{46}$, mw=1701.18)). Other compounds that can be specifically included or excluded from the composites described herein include catechin (mw=290.26), quercetin (mw=302.24), cyanidin (mw=287.24), gelatin, epchlorohydrin moieties, or combinations thereof.

Tannins.

Tannins include oligomeric polyphenols that occur naturally in a variety of plants. Isolated tannins typically form a heterogeneous mixture of tannin compounds. Tannin compounds can be subdivided into two groups: condensed tannins, also known as proanthocyanidins ("PA" or "PAC"), and hydrolysable tannins (HT). Tannin oligomers typically occur as dimers, trimers, tetramers, pentamers, hexamers, heptamers, octamers, nonamers, or decamers. Oligomers with greater than ten monomeric segments can also be isolated, such as oligomers that include up to 50 units, as described herein. For a review of tannin nomenclature, see Beecher (*J. Nutrition* 2003, 3248S-3254S), which is incorporated herein by reference. In some embodiments, certain monomeric tannins or low DP tannins can be excluded from a particular composition. For example, a composition may exclude catechin, tannic acid, or other monomeric tannins, dimeric tannins, trimers, or tetramers, PA tannins, or alternatively, HT tannins, a certain molecular weight range of tannins, or a type, class, or specific tannin cited in Beecher.

Proanthocyanidins are polymers of flavan-3-ols and flavans linked through an interflavan bond between carbon 4 of the C ring and carbon 8 of the A ring, as shown in Scheme 1. Scheme 1 illustrates a cranberry polyflavan-3-ol showing structural variation in the nature of interflavan linkage and substitution to an anthocyanin terminal unit through a $CH_3$—CH bridge.

Scheme 1. Representative structures of a proanthocyanidin (PA).

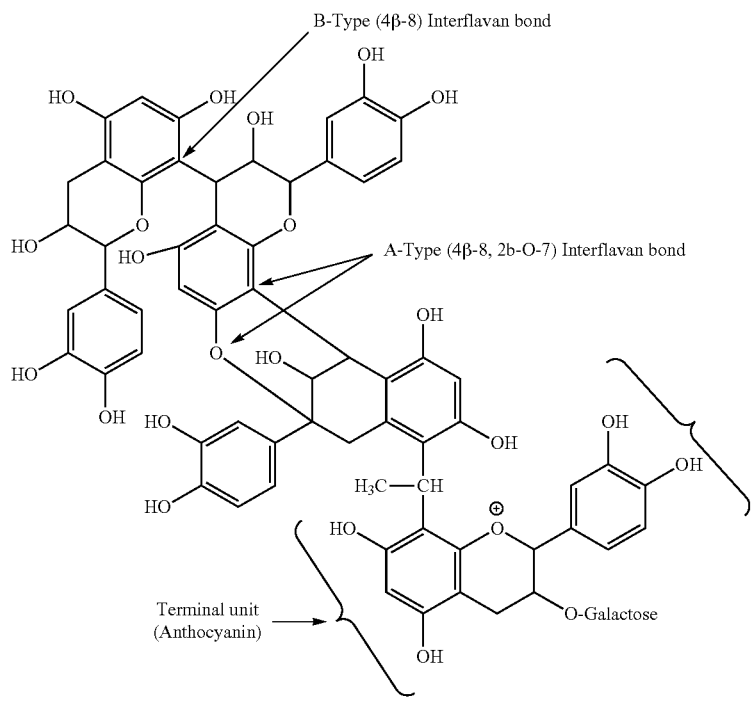

Scheme 2 illustrates two other types of condensed tannins (PAs): procyanidins and prodelphinidins (for the trimer x=1; for the tetramer, x=2; for the pentamer, x=3; for the hexamer, x=4; for the heptamer, x=5; for the octamer, x=6; for the nonamer, x=7; and for the decamer, x=8). Procyanidins (R=H) contain catechin and/or epicatechin (CE) subunits; prodelphinidins (R=OH) contain gallocatechin and/or epigallocatchin (GE) subunits.

Scheme 2. Representative structures of a proanthocyanidin (PA).

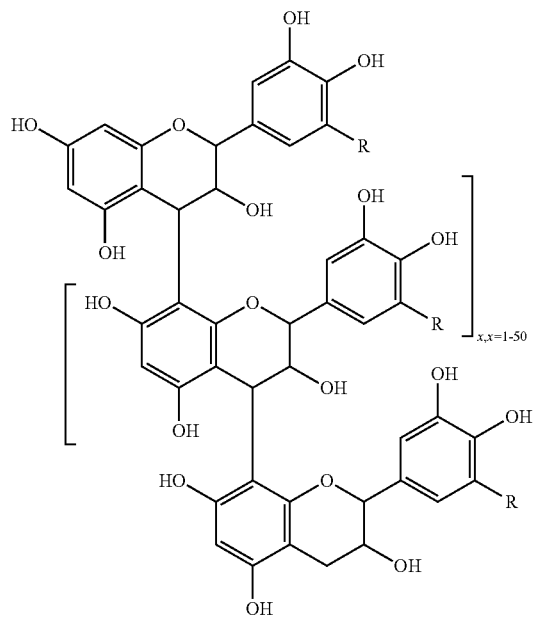

R = H and/or OH.

In various proanthocyanidins, the R groups of Scheme 2 can each independently be H or OH. In some embodiments, one or more hydroxyl groups may be glycosylated. In some embodiments, x is 1 to about 50, 1 to about 25, 1 to about 20, 1 to about 12, 1 to about 10, or a range of between any to integers from 1 to 50. The condensed tannins (PAs) can have various interflavanoid linkages (such as A-type 4→8 or 4→6 interflavan bonds, or B-type 4→8, 2→O-7 interflavan bonds, each α or β), cis- or trans-stereochemistry, and one or more hydroxyl groups can optionally be absent on the A-ring, B-ring, C-ring, or a combination thereof.

Other PA tannins include glycosylated heteropolyflavans, such as those illustrated in Scheme 3. Representative compounds shown in Scheme 3 include proluteolinidin (R'=OH); proapigininidin (R$^1$=H); eriodictyol (R$^2$=H); and eriodictyol 5-O-β glucoside (R$^2$=glucose). Krueger et al. have described a variety of known heteropolyflavans-3-ols and glycosylated heteropolyflavans (see J. Agric. Food Chem. 2003, 51, 538-543, which is incorporated herein by reference).

Scheme 3. Representative structures of a proanthocyanidin (PAs).

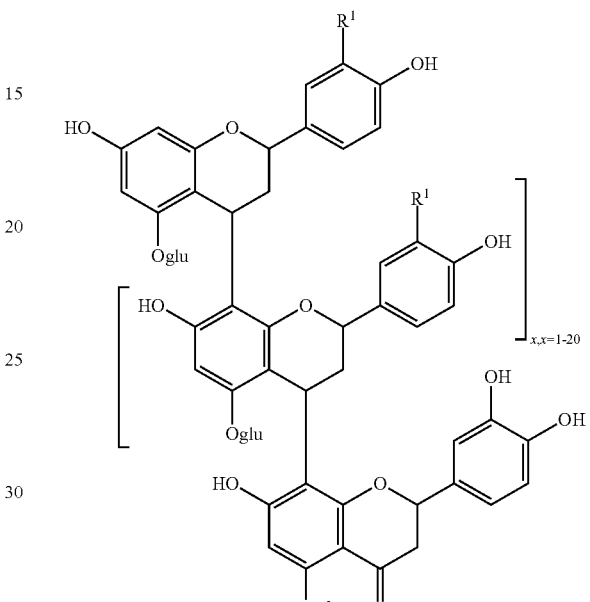

where $R^1$ is H or OH; $R^2$ is H or glucose; and glu is glucose (e.g., a β-glucoside).

In some embodiments, x of Scheme 3 is 1 to about 50, 1 to about 25, 1 to about 20, 1 to about 12, 1 to about 10, or a range of between any to integers from 1 to 50. Several examples of condensed tannins are described in U.S. Pat. No. 7,122,574 (Romanczyk et al.), which is incorporated herein by reference.

A review by Reed et al. (Phytochem. 66(18): 2248-2263 (2005)) describes the structural heterogeneity of tannin polyphenols from cranberries, grape seed extracts, sorghum, and pomegranates as characterized by MALDI-TOF MS. Examples of plants that produce proanthocyanidins include cranberries, blueberries, grapes, sorghum, and pine.

Hydrolysable tannins include gallic acid and ellagic acid esters of polyol core moieties, such as sugars. Scheme 4 illustrates a pomegranate ellagitannin showing structural variation in nature of esterification of the glucose core molecule.

Scheme 4. Representative structure of a hydrolysable tannin.

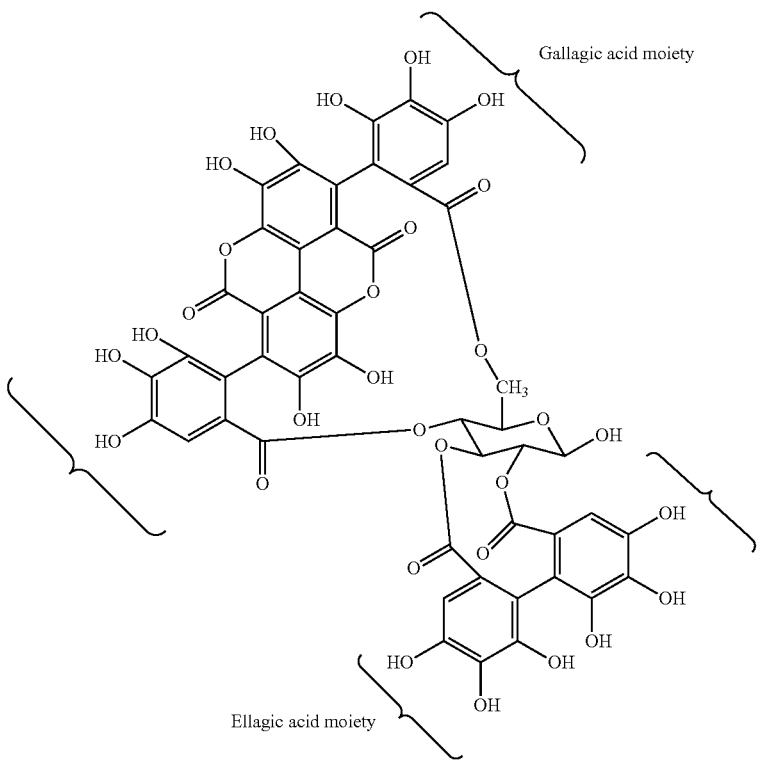

Hydrolysable tannins, such as the compound shown in Scheme 4, can be isolated in oligomeric forms that include 2 to about 12 hydrolysable tannin moieties, for example, linked by oxidative C—O coupling between galloyl and hexahydroxydiphenoyl moieties of the monomeric precursors. Common coupling also occurs between two ellagic acid moieties, or by addition of gallic acid moieties to the saccharide core of an oligomer. See Quideau and Feldman, *Chem. Rev.* 1996, 96, 475-503, which is incorporated herein in its entirety.

Accordingly, in some embodiments of compositions described herein, the hydrolysable tannins employed will be oligomeric hydrolysable tannins Thus in some embodiments, oligomeric hydrolysable tannins include at least two saccharide core moieties. Other embodiments can include monomeric proanthocyanidins or hydrolysable tannins, and yet other embodiments can exclude monomeric tannins. In some embodiments, a hydrolysable tannin will include one or more (e.g., 1, 2, 3, 4, 5, or more) ellagic acid moieties, and in some embodiments, a hydrolysable tannin will include one or more (e.g., 1, 2, 3, 4, 5, or more) gallagic acid moieties.

Examples of plants that produce hydrolysable tannins include pomegranates, strawberries, raspberries, blackberries, and sumac. Significant quantities of hydrolysable tannins can be isolated from, for example, pomegranate husks. Specific hydrolysable tannins include punicalin and punicalagin (the alpha or beta isomer of 2,3-(S)-hexahydroxydiphenoyl-4,6-(S,S)-gallagyl-D-glucose, with a molecular weight of 1084) and stereochemical isomers thereof, as well as the hydrolysable tannins described by Quideau and Feldman (*Chem. Rev.* 1996, 96, 475-503).

Consumption of foods, beverages and nutritional supplements that contain tannins is associated with decreased risk of diseases that have an oxidative and microbial adherence etiology. Numerous studies show that tannins have various types of pharmacological properties including anti-oxidative, anti-mutagenic, anti-carcinogenic, anti-angiogenic, apoptotic, anti-obesity, hypocholesterolemic, anti-arteriosclerotic, anti-diabetic, anti-bacterial, anti-viral, and anti-aging effects, as well as wound healing properties.

Chitosan.

Chitin is a biopolymer composed of poly N-acetyl glucosamine. Chitin is the second most abundant biopolymer on earth, after only cellulose. It is commonly found in the exoskeleton or cuticles of many invertebrates, such as the shells of marine arthropods, and in the cell wall of most fungi and some algae. Chitin is generally insoluble in water but can be deacetylated by treatment with a caustic, such as sodium hydroxide, to form the soluble cationic polysaccharide, chitosan. The chemical name of chitosan is poly($\beta$-(1→4)-2-amino-2-deoxy-D-glucopyranose). Chitosan has two types of reactive groups that can be grafted: the free amine groups on deacetylated units, and the hydroxyl groups on the C3 and C6 carbons on either acetylated or deacetylated units (Scheme 5).

Scheme 5. General Chitosan Structure.

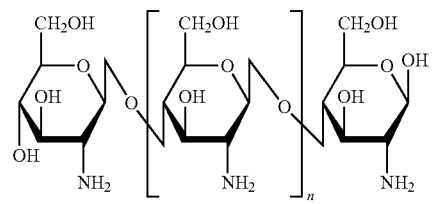

Chitosan is commonly used in water processing and in agriculture. Chitosan can also form a polycationic, biodegradable, and biocompatible matrix with blood clotting and antimicrobial properties. Kumar et al. (*Chemical Reviews* (2004) 104:6017-6084) and Rinaudo (*Progress in Polymer Science* (2006) 31:603-632) have reviewed the properties and applications of chitosan. Due to its unique polycationic nature, chitosan and its derivatives have been used for various applications in many different fields, including biomedicine, food, agriculture, biotechnology and pharmaceutics. Chitosan has been developed for a variety of biomedical applications including wound dressings and drug delivery systems. In the context of drug delivery, chitosan has been used as a stabilizing constituent of liposomes; as an excipient controlling drug release in oral formulations; as a nasal delivery system; to prepare microspheres for encapsulation of enzymes, proteins and cells, and also to deliver DNA.

Research has shown that the water solubility, antibacterial, and antioxidant properties of chitosan can be improved by primary derivation followed by graft modification. Grafting chitosan is also a common way to improve other properties such as increased chelating or complexation properties, bacteriostatic effects, or enhanced adsorption properties. Although the grafting of chitosan modifies its properties, useful characteristics such as mucoadhesivity, biocompatibility, and biodegradability can still be maintained.

Chitosan-based bandages and surgical dressings produced by HemCon Medical Technologies were recently approved by the U.S. FDA for use as hemostatic bandages with proven antibacterial properties against a wide range of harmful organism, including MRSA and *acinetobacter baumannii*. The bandages and dressings can be used to rapidly stop bleeding, including extensive arterial bleeding. Both the blood clotting and the antibacterial properties of the materials can be attributed to chitosan (see U.S. Pat. No. 7,482,503 (Gregory, et al.), which is incorporated herein by reference). The tannin-chitosan composite material can be used in place of the chitosan in the compositions described therein.

Chitosan is commercially available from many chemical suppliers, such as Sigma Aldrich Co., St. Louis, Mo. Chitosan is offered in various grades, average molecular weights, and degrees of deacetylation.

In some embodiments, the chitosan can be a "high molecular weight" chitosan. High molecular weight chitosan refers to chitosan that has a number average molecular weight of at least about 100 kDa, and typically about 170 kDa to about 400 kDa. In some embodiments, high molecular weight chitosan can have a molecular weight of at least about 100 kDa, at least about 110 kDa, at least about 150 kDa, or at least about 200 kDa. In other embodiments, high molecular weight chitosan can have a molecular weight of about 100 kDa to about 400 kDa, about 120 kDa to about 400 kDa, about 150 kDa to about 400 kDa, about 170 kDa to about 400 kDa, 100 kDa to about 300 kDa, about 120 kDa to about 300 kDa, about 150 kDa to about 300 kDa, about 170 kDa to about 300 kDa. The value of n in Scheme 5 can be any number or range that results in approximately the values for the molecular weights of chitosan described herein. As would be readily recognized by one of skill in the art, chitosan as illustrated in Scheme 5 may also be partially acetylated.

Other embodiments may include low molecular weight chitosan. Low molecular weight chitosan refers to chitosan molecules with less than 100 monomeric units (less than about 18 kDa or less than about 20 kDa). Molecular weights of chitosan can be determined, for example, by gel permeation chromatography.

The chitosan can have a degree of deacetylation that is typically at least about 70%, at least about 75%, at least about 80%, at least about 85%, at least about 90%, at least about 95%, at least about 99%, or the chitosan can be substantially fully deacetylated.

Tannin-Chitosan Composite Materials.

Chitosan binds to negatively charged tannins by electrostatic interactions, driven by its positively charged amino groups. This interaction allows for developing stable biomaterials, such as nanoparticles that can serve as therapeutic agents, as a targeted carrier compositions, and controlled release system. The tannin-chitosan composite biomaterial can also form biofilms, biofoams, and tissue scaffolds. Tannin-chitosan composite materials can be used to prepare dermal patches, for example, for wound healing applications. The tannin-chitosan composite materials can also be used as scaffolding for skin and cartilage tissue cultures, for matrices for tissue engineering, for coatings for biomedical devices, or as packaging materials, for example, to prevent oxidation of organic materials such as meats and/or lipids, and/or for drug delivery.

The tannin-chitosan composite materials provide higher biocompatibility and superior biodegradability relative to known synthetic composites. In addition to direct biological effects from the tannin-chitosan composites (antimicrobial and antioxidant properties), the biomaterials can be used for targeting or controlled release systems to encapsulate therapeutic agents for oral, dermal, or respiratory delivery.

With respect to oral delivery, some studies have shown that the antioxidant activity of catechin, a component of tannins, decreases dramatically when it is exposed to an alkaline pH, such as in the human intestine. Considering the function of tannins in metabolic processes, as well as the properties of tannins manifested in vitro, complexation to chitosan can protect tannins from interactions with the food matrix, and can also provide for delayed or controlled release in the gastrointestinal tract.

Nanoparticles and biofilms can be prepared from chitosan and tannins, as described herein. High molecular weight tannins are particularly useful for preparing nanoparticles. Low molecular weight tannins are well suited for preparing chitosan-tannin composite foams, whereas tannins of intermediate molecular weight provide superior biofilms compared to known chitosan biofilms. According to the specifications provided by Sigma-Aldrich, a chitosan with low molecular weight refers to chitosan polymer that has about 50 to about 250 monomeric units (5,000-10,000 Da), a medium molecular weight chitosan sample has a molecular weight in the approximate range of about 10,000 to about 100,000 Da. A high molecular weight chitosan typically refers to a chitosan with a molecular weight of about 100,000 to about 500,000 Da.

Two classes of tannin-chitosan composite nanoparticles are the proanthocyanidin-chitosan composites and the hydrolysable tannin-chitosan composites. The proanthocyanidin-chitosan composites can be prepared from, for example, cranberry tannins and chitosan. The proanthocyanidins can also be obtained from, for example, grapes (e.g., from fruit, wine, juice, or presscake), cinnamon, apples, or grain sorghum. The hydrolysable tannin-chitosan composites can be prepared from, for example, pomegranate tannins and chitosan. Other hydrolysable tannins can be obtained from, for example, strawberries, raspberries, or sumac.

The chitosan-tannin composite can be crosslinked during its preparation. Nanoparticles can be crosslinked, for example, with tripolyphosphate (TPP) anions. Biofilms can be crosslinked, for example, with glutaraldehyde. Swelling of a biopolymeric matrix can produce faster degradation/active compound release from the matrix. In both the nanoparticles and the biofilms, crosslinking reduces or prevents spontaneous swelling of the biopolymeric matrix. In nanoparticles, TPP strengthens the polymeric networks to maintain a spherical nanoparticle shape. In biofilms, crosslinking can reduce or prevent fast release/degradation of the biofilm. By controlling the concentration of the crosslinker added during preparation, it is possible to control the release rate of active compounds from the matrix. Additionally, increasing degree of polymerization of tannin component increases crosslinking efficiency, thereby reducing amount of TPP needed for a similarly stable particle, as well as influencing particle size. The DP can be controlled by choice of starting material and chromatographic separation, all of which can be monitored by MALDI MS.

In some embodiments, the chitosan-tannin composite material can include or exclude polymers other than chitosan or tannins For example, some embodiments include cellulose or collagen-derived materials such as gelatin; other embodiments exclude them. Some embodiments include synthetic polymers such as polyethylene or polyethylene oxide, while other embodiments exclude them.

Antimicrobial Applications and Drug Delivery.

Chitosan itself has valuable biopharmaceutical characteristics such as pH sensitivity, biocompatibility and low toxicity. Chitosan is also metabolized by certain human enzymes, especially lysozyme, and is therefore biodegradable. For drug delivery applications, it is important for the chitosan formulation to be hydro-soluble and positively charged. These properties enable it to interact with negatively charged polymers, macromolecules and polyanions in an aqueous environment.

The chitosan-tannin complexes described herein have higher protein and drug loading efficacy and capacity, as well as better release properties, than chitosan itself. The complexation of chitosan to tannins enhanced its stability at different pH environments compared to chitosan alone. The chitosan-tannin complexes also showed an increase in the rate of uptake and activation of macrophage cells. Cell culture experiments show the non-cytotoxicity and successful internalization of these chitosan-tannin nanoparticles. Accordingly, these novel composite nanoparticles can be used as targeted drug-delivery carriers. The composites can also be used for a wide range of applications that involve the efficient intracellular delivery of biological agents to modulate the behavior of cells.

Tannin-chitosan composite nanoparticles can also be used as therapeutic biomaterials, for example, to control pathogenic microbial colonization of human epithelial cells. Because the nanoparticles themselves display antimicrobial and antioxidant properties, contacting epithelial cells with tannin-chitosan composite nanoparticles can kill, inhibit, or prevent the spread of a pathogenic microbes and microbial infections. Administration of the nanoparticles to a mammal can therefore treat and/or prevent human disease states such as diarrhea, resulting from enterotoxigenic *Escherichia coli* (ETEC) and other pathogenic microbe colonization of the intestinal epithelial cells, and urinary tract infections (UTI) resulting from adhesion of P-fimbriated uropathogenic bacteria to uroepithelial cells.

Additionally, tannin-chitosan composite nanoparticles can be used in feed additives, for example, to reduce shedding of *E. coli* O157:H7 in cattle, and as a replacement for antibiotics in animal feeds. The nanoparticles can also be used to replace herbicides, fungicides, and/or pesticides to control in-the-field and post harvest damage cause by plant pathogens.

Tissue Engineering.

The present generation of tissue engineering (TE) research is based on the seeding of cells onto porous biodegradable polymer matrixes. A primary factor for successful seeding is the availability of good biomaterials to serve as the temporary matrix. Recently, chitosan and its derivatives have been reported as attractive candidates for scaffolding materials because they degrade as the new tissues are formed, eventually without inflammatory reactions or toxic degradation. In TE applications, the cationic nature of chitosan is primarily responsible for electrostatic interactions with anionic glycosylaminoglycans, proteoglycans, and other negatively charged molecules.

Tannin complexation to chitosan promotes a surface modification on chitosan films that increases the porosity of its 2D scaffolds, as shown by SEM micrographs. Tannins have also been found to improve the physical properties of chitosan biofilms, such as tensile strength, swelling degree, and thermal stability, as shown by mechanical analysis and DSC calorimetry. The chitosan-tannin composite polymer can be used to control the morphology and function of cells, and therefore can be used in tissue engineering, dermal drug delivery, and wound healing applications. The chitosan-tannin composites can also be chemically modified for TE applications. For example, the composites can be modified by grafting particular sugars to a tannin backbone. Certain cells can distinctively recognize the specific sugars, thus providing the specific recognition to antigen presenting cells such as B-cells, dendritic cells, and macrophages.

Wound Healing.

Chitosan-tannin complexes (composites) also have valuable properties for wound healing applications because they exhibit enhanced bacteriostatic activity with respect to pure chitosan. An increase in chitosan antimicrobial activity is observed in the chitosan-tannin complexes, which bind to the negatively charged bacterial surface to disturb the cell membrane. These properties can be applied to use of the complexes for dermal patches, such as biofilms, for example, to promote ulcer and burn healing. The chitosan-tannin composites can also be used as hemostatic agents in wound dressings.

The chitosan-tannin complexes can be used in a variety of other biomedical applications. As a result of the biocompatible properties, such as good blood compatibility and cell growth efficiency, chitosan-tannin composites can be used in cardio-vascular applications. The permeability of chitosan-tannin composite membranes can be controlled through plasma-treatment. Such composite membranes can therefore be used in dialysis.

The preparation of wound dressings is described in U.S. Pat. No. 7,482,503 (Gregory et al.). Wound dressings can be prepared according to such methods using the chitosan-tannin composite material described herein in place of the chitosan biomaterial described therein. Additionally, the chitosan-tannin composites can be used as coatings for medical devices, such as stents or catheters, to prevent detrimental biofilm formation or bacteremia in patients.

Liposomes.

The chitosan-tannin composite material can be used to coat other compositions, for example, using electrostatic deposition methods. Chitosan-tannin composite material can be electrostatic deposited onto liposomes to increase their stability and provide enhanced delivery to specific cells or tissues. Coated liposomes can be used as targeted release-on-demand carrier systems for both water- and oil-soluble functional compounds such as drugs, antimicrobials, flavors, antioxidants, and other bioactive ingredients. The deposition of chitosan-tannin composites improves the stability of liposomes, provides a more biodegradable and biocompatible coated liposome than current synthetic stabilization techniques, and adds antioxidant and antimicrobial functionality to the liposomes.

Liposomes coated with chitosan-tannin composite materials can provide contrast agents for use with diagnostic and therapeutic ultrasound procedures. Contrast agents such as Optison™ Perflutren Protein-Type A Microspheres Injectable Suspension and Definity® perflutren encapsulated lipid microspheres are currently injected into systemic blood flow. Tannin-chitosan composites can be incorporated into such liposomes to improve contrast features, assist in delivery of therapeutic agents such as drugs or genes, or they can act alone as therapeutic agents.

Nutraceutical or Supplement Formulations.

The invention also provides formulations that include a tannin-chitosan composite matrix described herein for use as a dietary supplement. Supplement compositions can be formulated as capsules, tablets, powders, solutions, gels, bar, suspensions, creams, and the like. These dietary supplements, for example, in powder or solution form, can be added to nutraceuticals, foods and/or beverages to form pharmaceutical, functional nutraceutical, food, and/or beverage products. The chitosan-tannin composite material can form a nanoparticle that encapsulates additives such as vitamins or nutrients, or the composite material can be combined with an additive in a capsule, tablet, powder, solution, gel, bar, suspension, cream, or the like.

Dietary supplements may be formulated as powders, for example, for mixing with consumable liquids such as milk, juice, water or consumable gels or syrups for mixing into other dietary liquids or foods. Dietary supplements can be formulated with other foods or liquids to provide pre-measured supplemental foods, such as single serving bars. Typical food products that can incorporate a tannin-chitosan composite matrix include dairy foods such as yogurt, cereals, breads, snack food products, fruit juices, sports drinks and soft drinks Flavorings, binders, protein, complex carbohydrates, vitamins, minerals and the like can be added as desired. Dietary supplements can be formulated by standard techniques known to those of skill in the art, such as the techniques described in U.S. Pat. No. 7,767,235 (Shrikhande et al.), which is incorporated herein by reference.

Examples of drugs, vitamins and nutrients that can be incorporated into formulations include lipids such as fatty acids, including omega-3 and omega-6 fatty acids, fat soluble vitamins (e.g., vitamin A, D, E, and/or K), water soluble vitamins (e.g., vitamin C, thiamine, riboflavin, niacin, pantothenic acid, vitamin B6, folate, vitamin B12,), antibiotics (e.g., amoxicillin, ampicillin, clindamycin, doxycycline, erythromycin, metronidazole, penicillin, tetracycline, vancomycin, and the like), probiotics (e.g., lactic acid bacteria, bifidobacteria, and the like), micronutrients such as β-carotene and/or ascorbic acid, proteins, and peptides. In some embodiments, monomeric tannins and/or other nutritional supplements can be incorporated into a chitosan-tannin composite matrix, or they can be included in a composition that includes a chitosan-tannin composite matrix.

Analysis of Tannins, Chitosan, and Combination Products.

A variety of methods can be used to analyze and evaluate tannins, chitosans, and their composite products. These techniques include Matrix Assisted Laser Desorption/Ionization Time-of-Flight Mass Spectrometry (MALDI-TOF MS), American Standards for Testing Materials (ASTM) measurements of tensile strength and swelling properties, scanning electron microscopy (SEM) to characterize surface morphology, differential scanning calorimetry (DSC) for thermal characterization of the composite biomaterial, and United States Pharmacopeia (USP) methods to study drug release.

MALDI-TOF MS is especially suited to analyze the tannin-chitosan composite materials because the technique can detect intact molecular ions with high molar masses (e.g., >100,000 Da). MALDI-TOF MS is also useful for characterizing polydispersed oligomers that exhibit large structural heterogeneity, including tannins, chitosans, and their composites. Tensile strength and swelling properties of the composite biomaterials were characterized ASTM measurements.

Analysis of the tannin-chitosan composites described herein indicates that the composite materials have improved stability, higher drug loading capacity, improved drug release properties, improved cell uptake, greater porosity, improved tensile strength and thermal stability compared to compositions that include only chitosan, and the materials are non-cytotoxic in vitro.

Pharmaceutical Formulations.

The chitosan-tannin composite materials can be formulated as pharmaceutical compositions and administered to a mammalian host, such as a human patient, in a variety of forms adapted to the chosen route of administration, e.g., orally or parenterally, by intravenous, intramuscular, topical or subcutaneous routes.

The chitosan-tannin composite materials may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the chitosan-tannin composite materials may be combined with one or more excipients and used in the form of ingestible tablets, troches, capsules, elixirs, suspensions, syrups, wafers, and the like. Such compositions and preparations typically contain at least 0.1% of the chitosan-tannin composite materials. The percentage of the compositions and preparations may, of course, be varied and may conveniently be between about 2% to about 60% of the weight of a given unit dosage form. The amount of chitosan-tannin composite materials in such therapeutically useful compositions is such that an effective dosage level will be obtained.

Tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the chitosan-tannin composite materials may be used as a sustained-release preparation for the administration of bioactive agents, such as drugs or other therapeutic agents.

The chitosan-tannin composite materials may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations may contain a preservative, for example, to prevent the growth of certain microorganisms.

The pharmaceutical dosage forms suitable for injection or infusion can include sterile aqueous solutions or dispersions or sterile powders comprising the chitosan-tannin composite materials which are adapted for the extemporaneous preparation of sterile injectable or infusible solutions or dispersions. The chitosan-tannin composite materials may also be coatings for liposomes that encapsulate bioactive agents. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the maintenance of the required particle size in the case of dispersions or by the use of surfactants. The prevention of the action of certain microorganisms can be brought about by various additional antibacterial and antifungal agents, for example, parabens, chlorobutanol, phenol, sorbic acid, thiomersal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation include vacuum drying and freeze drying techniques, which yield a powder of the chitosan-tannin composite materials plus any additional desired ingredient present in the previously sterile-filtered solutions.

For topical administration, the chitosan-tannin composite materials may be applied in pure form. However, it will generally be desirable to administer them to the skin as compositions or formulations, e.g., in combination with a dermatologically acceptable carrier, which may be a solid or a liquid.

Useful solid carriers include finely divided solids such as talc, clay, microcrystalline cellulose, silica, alumina and the like. Useful liquid carriers include water, dimethyl sulfoxide (DMSO), alcohols or glycols or water-alcohol/glycol blends, in which the chitosan-tannin composite materials can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the chitosan-tannin composite materials to the skin are known to the art; for example, see Jacquet et al. (U.S. Pat. No. 4,608,392), Geria (U.S. Pat. No. 4,992,478), Smith et al. (U.S. Pat. No. 4,559,157), and Wortzman (U.S. Pat. No. 4,820,508).

Useful dosages of the chitosan-tannin composite materials can be determined by comparing their in vitro activity, and in vivo activity in animal models. Methods for the extrapolation of effective dosages in mice, and other animals, to humans are known to the art; for example, see U.S. Pat. No. 4,938,949 (Borch, et al.). The amount of the chitosan-tannin composite materials required for use in treatment will vary not only with the particular composite form used but also with the route of administration, the nature of the condition being treated and the age and condition of the patient and will be ultimately at the discretion of the attendant physician or clinician. For example, the chitosan-tannin composite materials may be conveniently administered in unit dosage form; for example, containing 5 to 1000 $mg/m^2$, 10 to 750 $mg/m^2$, or 50 to 500 $mg/m^2$ of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The present invention provides therapeutic methods of treating various conditions in a mammal, which involve administering to a mammal having such a condition an effective amount of a chitosan-tannin composite of the invention. A mammal includes a primate, human, rodent, canine, feline, bovine, ovine, equine, swine, caprine, bovine and the like. In other embodiments, the chitosan-tannin composite materials can be used to treat various conditions in plants, such as bacterial or fungal infections.

The following Examples are intended to illustrate the above invention and should not be construed as to narrow its scope. One skilled in the art will readily recognize that the Examples suggest other ways in which the invention could be practiced. It should be understood that numerous variations and modifications may be made while remaining within the scope of the invention.

EXAMPLES

Example 1

Tannin-Chitosan Composites: Preparation, Data, and Applications

Pharmaceutical grade chitosan (deacetylation degree of 92% calculated by $^1H$ NMR; mean molecular weight of 185 kDa calculated by specific viscosimetry) derived from shrimp shells was provided by the Polymers Research Laboratory (POLIUNA) of Costa Rica. The degree of deacetylation and mean molecular weight distribution can be controlled in the production of tannin-chitosan composites to provide chitosan with higher or lower degrees of deacetylation, and/or higher or lower mean molecular weights. Chitosan-tannin composites that included hydrolyzable tannins (HT) and proanthocyanidins (PA) were separately prepared and analyzed.

Proanthocyanidins (PA).

Polyphenolics were isolated by liquid chromatography and subjected to MALDI-TOF MS using trans-3-indoleacrylic acid as the matrix. Spectral analysis provided the degree of polymerization, monomeric substitution, and the nature of intermolecular bonds (Reed et al. 2005).

The cranberry polyflavan-3-ols had variation in interflavan bonds (A-type and B-type) and contained polyflavan-3-ols linked to anthocyanins through a $CH_3$—CH bridge (see Scheme 1 above) (Krueger et al. 2004). Polygalloyl-polyflavan-3-ols in grape seed extract had large variation in the degree of galloyl substitution (Krueger et al. 2000). Sorghum polyflavans had structural heterogeneity in glycosylation and hydroxylation (Krueger et al. 2003).

Cranberry polyphenols were chosen as a representative for the class of 'proanthocyanidins' in formulations of Tannin (PA)-Chitosan bioconjugates. Spray dried cranberry juice powder was reconstituted in $H_2O$ and applied to a preparative LH-20 column equilibrated in water. Water, 50% aqueous ethanol (v/v), and ethanol were sequentially eluted through the column to remove non-phenolic cranberry constituents as well as monomeric phenolic constituents (hydroxycinnamic acids, anthocyanins and flavonols). Aqueous acetone (4:1; acetone: $H_2O$, v:v) was then passed through the column until it was white, to elute a mixture of cranberry PA. The aqueous acetone fraction was concentrated by vacuum to remove the acetone and the water was removed by freeze drying.

Other solid phase chromatographic resins (C18, C8, Waters Oasis resins, Amerlite resins, and the like) can also be used to enhance extraction of particular tannin fractions. Likewise, liquid/liquid (partition) chromatography can be used for extractions, as well as supercritical fluid extraction techniques. Additional techniques that can be used for the isolation and purification of various tannins are described in U.S. Pat. No. 7,122,574 (Romanczyk et al.), which is incorporated herein by reference.

The cranberry proanthocyanidin composition was characterized by MALDI-TOF MS, showing a degree of polymerization (DP) ranging from 4 to 7, with at least one A-type interflavan bond present at for each degree of polymerization. FIG. 1 illustrates a MALDI-TOF MS spectrum, in positive reflectron mode, of the cranberry PA fraction. The section between m/z 1000 and 2500 has been amplified to identify the degree of polymerization, the nature of interflavan linkage and structural composition of subunits of oligomeric PA. The degree of polymerization, monomeric substitution, and nature of intermolecular bonds are 'proanthocyanidin variables' that can be controlled by choice of raw starting material (plants, fruits, juices), extraction processes, and enrichments by liquid and solid phase chromatography.

Hydrolysable Tannins (HT).

Hydrolysable tannins were isolated from pomegranate peels. The hydrolysable tannins identified included gallic acid and ellagic acid esters of core polyol moieties, such as sugars (see Scheme 4 above). Pomegranate hydrolysable tannins that correspond to previously described structures, such as punicalagin, were identified. Others found were hydrolysable tannins that correspond to oligomeric ellgitannins in which two to five core glucose units are cross linked by dehydrodigalloyl and or valoneoyl units (Afaq et al. 2005 and Seeram et al. 2006). These results demonstrate the degree of polymerization, intermolecular bonds, pattern of hydroxylation, and substitution with monosaccharides and gallic acid, occur with an identifiable amount of heterogeneity.

HT Isolation.

Pomegranate polyphenols were chosen as t representative for the class of 'Hydrolyzable Tannins' for formulations of Tannin (HT)-Chitosan bioconjugates. Pomegranate peels (~5 g) were added to liquid nitrogen in a blender and ground to a powder. The powder was extracted with aqueous acetone 80% v/v, filtered, and concentrated by vacuum. Concentrated pomegranate extract was applied to a C18 preparative column equilibrated with water. Water was passed through the column to elute non-phenolic constituents. To elute a pomegranate HT fraction enriched in punicalagin, an aqueous methanol 50% (v/v) solution was then passed through the column until the resin became white.

Figure 2:
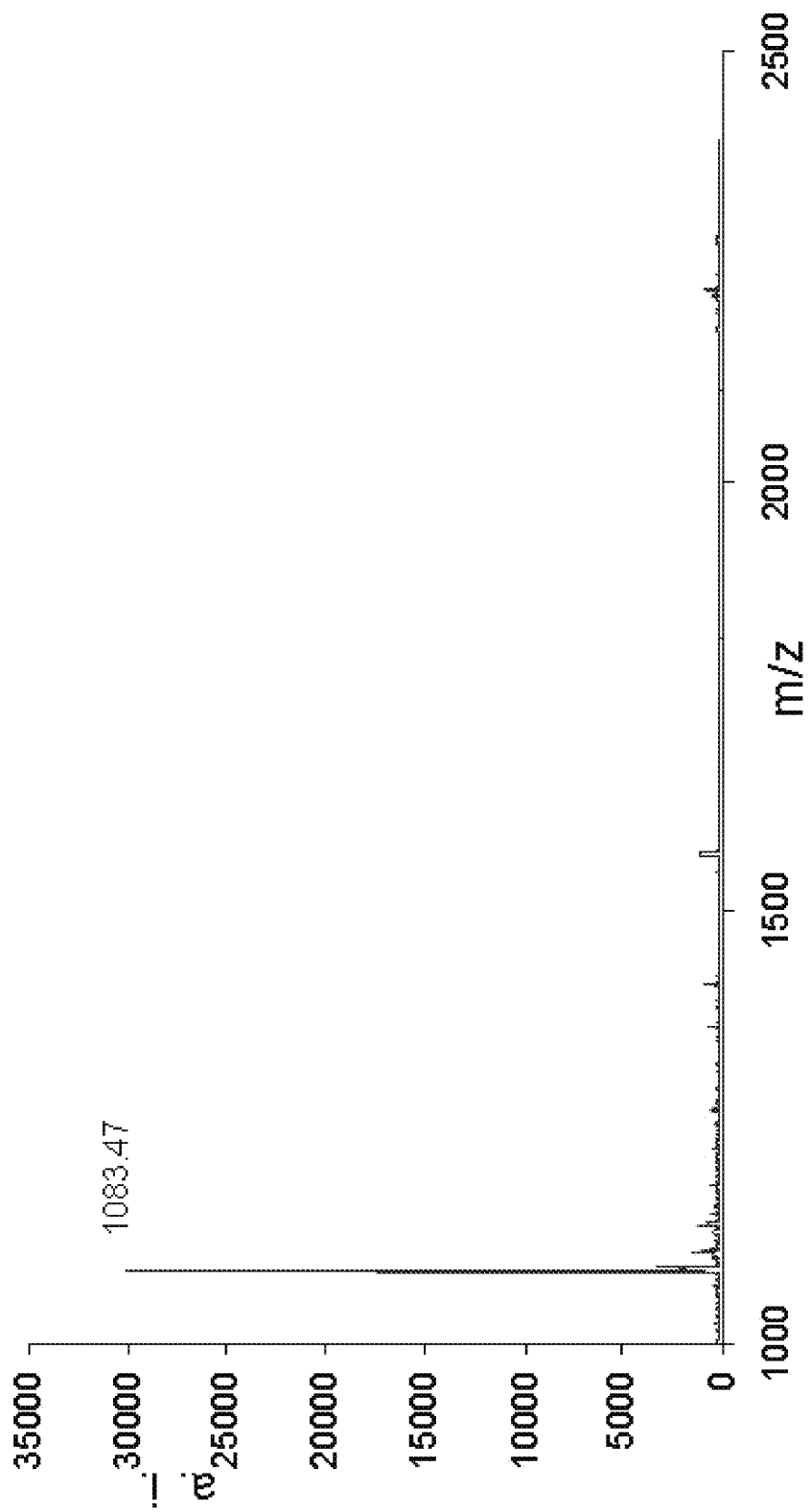
FIG. 2 illustrates a MALDI-TOF MS spectrum, in negative reflectron mode, of a pomegranate hydrolysable tannin.

MALDI-TOF MS and RP-HPLC analysis showed that the pomegranate HT fraction was composed mainly of punicalagin (~95%). FIG. 2 illustrates a MALDI-TOF MS spectrum, in negative reflectron mode, of the pomegranate hydrolyzable tannin. The degree of polymerization, monomeric substitution, and nature of intermolecular bonds are 'hydrolyzable tannin variables' that can be controlled by choice of raw starting material (plants, fruits, juices), extraction processes and enrichments by liquid and solid phase chromatography.

Preparation of Tannin-Chitosan Composites (Bioconjugates).

Figure 3:
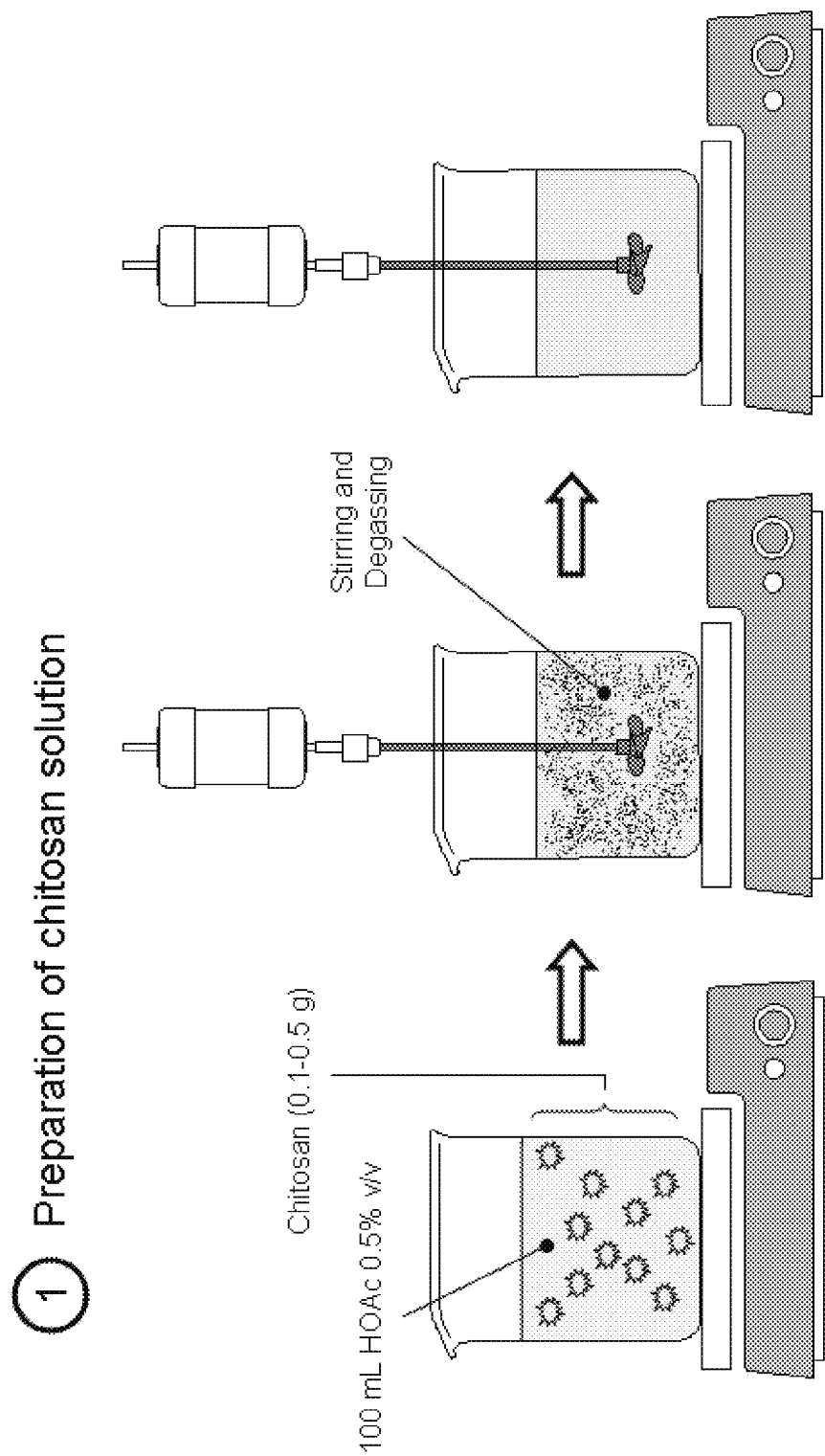
FIG. 3 illustrates dissolving and degassing a chitosan solution, according to an embodiment.
Figure 4:
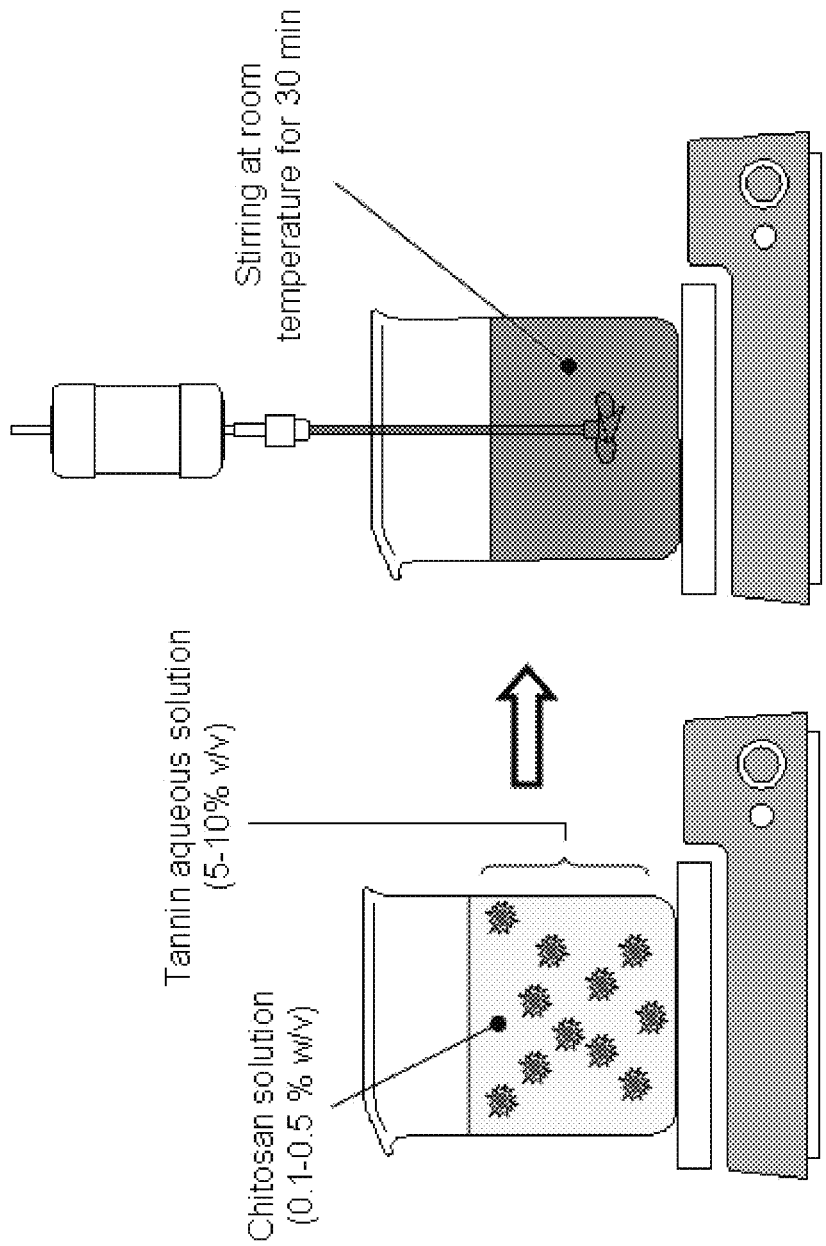
FIG. 4 illustrates the preparation of the chitosan-tannin bioconjugates, according to an embodiment.

A chitosan solution was prepared by dissolving chitosan powder in an acetic acid aqueous solution (0.5% v/v) at room temperature (~23° C.). After the chitosan powder was fully dissolved, the solution was filtered and degassed by vacuum filtration (Step 1). FIG. 3 schematically illustrates the dissolving and degassing the chitosan solution. The chitosan solution (0.5% w/v) was then mixed with either proanthocyanidins or hydrolyzable tannins (0.5-2.0% v/v), at different molar ratios. The solution was left to react, with stirring, for 1 hour at room temperature (Step 2). FIG. 4 further illustrates the preparation of the chitosan-tannin bioconjugates, according to an embodiment. The concentration of chitosan and tannins (PA and/or HT) were controlled in the process of forming composite materials by adding different ratios of the respective components to provide the desired composition.

Preparation of Tannin-Chitosan Composite 2D Hydrogels (Films).

Figure 5:
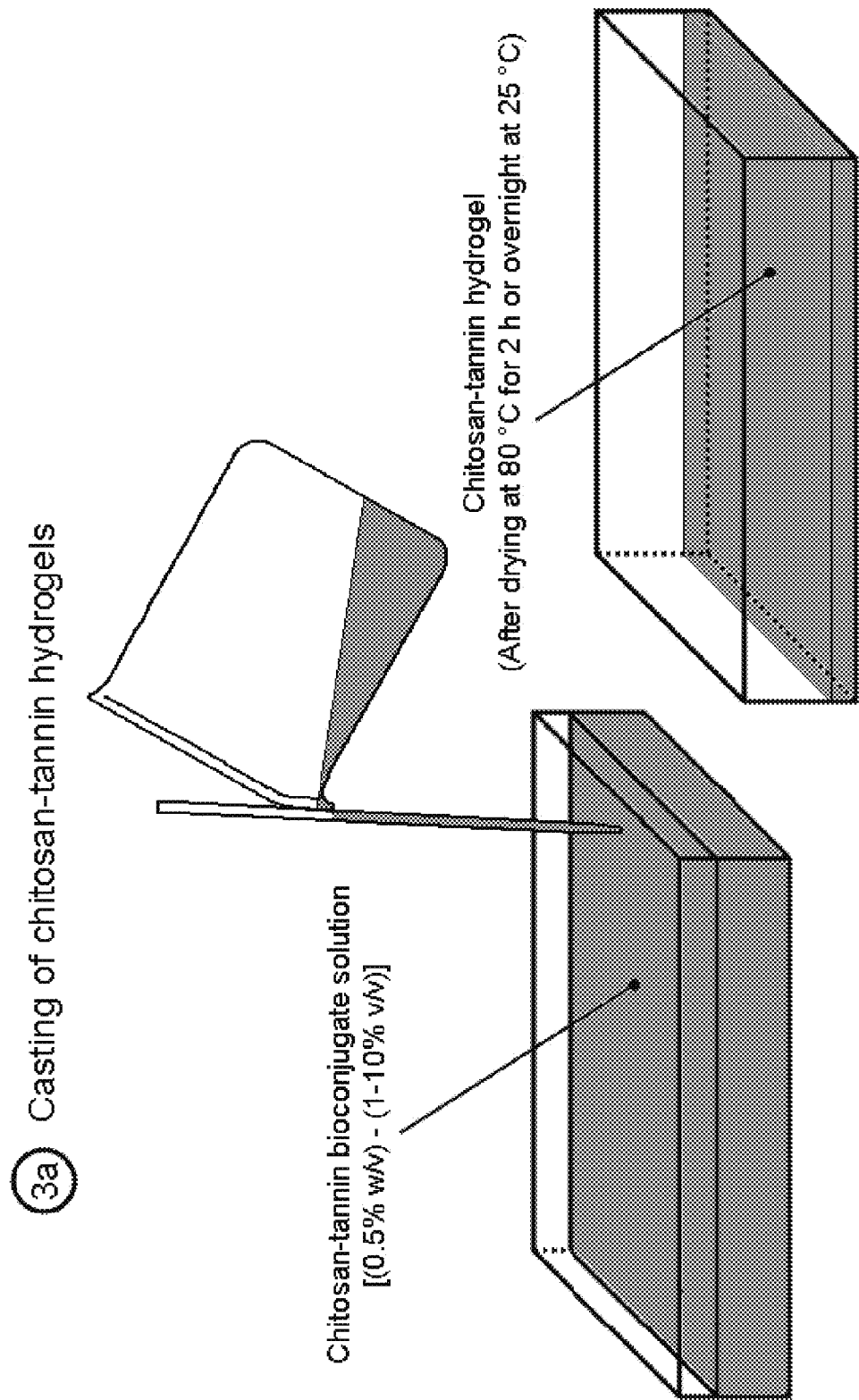
FIG. 5 illustrates the casting of the chitosan-tannin hydrogels, according to an embodiment.

The tannin-chitosan composite solutions were cast onto glass plates and slowly spread to form even liquid films. The liquid films were then evaporated at room temperature for 24 hours to form 2D biomembranes (hydrogels). The hydrogel films were subsequently washed repeatedly with deionized water and were dried at room temperature for 24 hours (Step 3a) to provide the composite films. FIG. 5 illustrates the casting of the chitosan-tannin hydrogels, according to an embodiment.

Preparation of Tannin-Chitosan Composite Nanoparticles.

Figure 6:
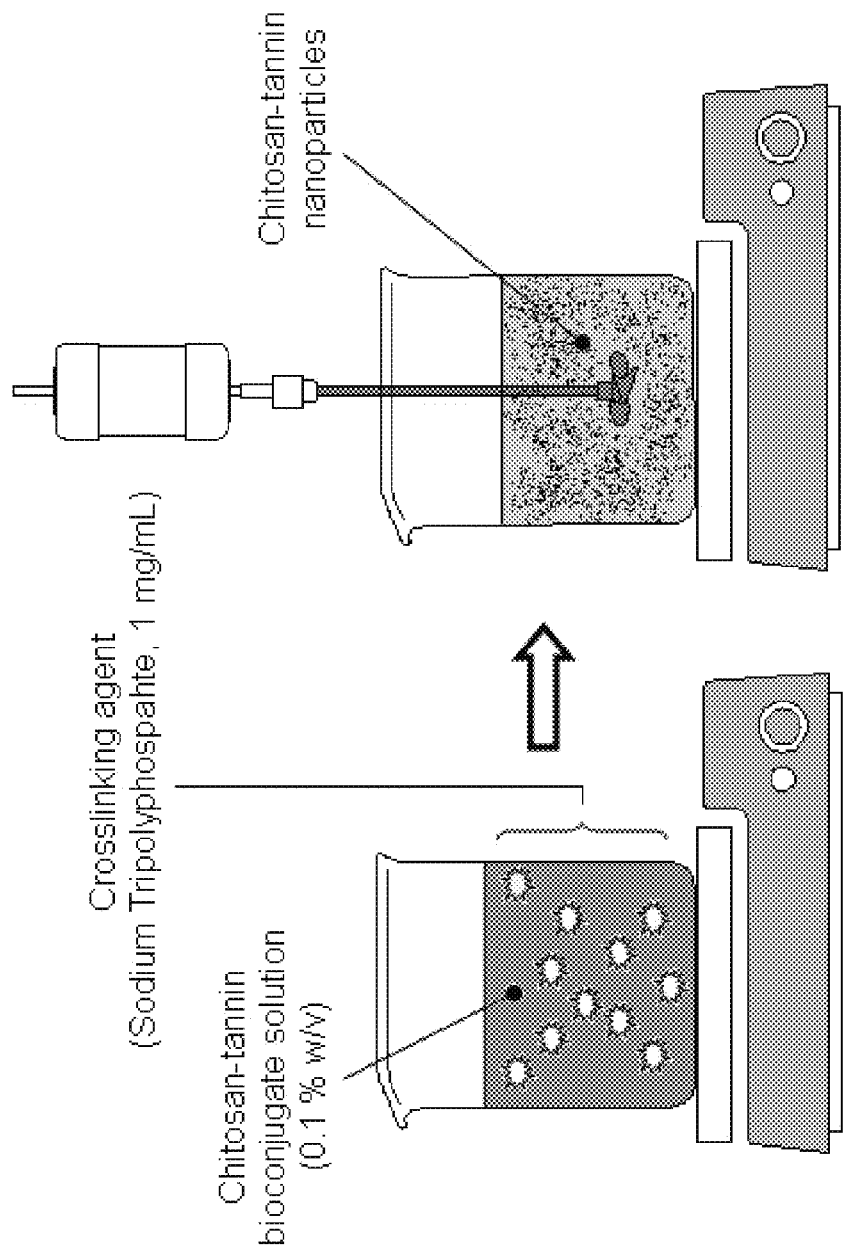
FIG. 6 illustrates the preparation of chitosan-tannin composite nanoparticles, according to an embodiment.

Chitosan-tannin nanoparticles were prepared by ionitropic gelation of chitosan with tripolyphosphate (TPP) anions. TPP was dissolved in water to a concentration of 1 mg/mL. Under magnetic stirring at room temperature, 2 mL of TPP solution were added to 5 mL of the tannin-chitosan composite solutions, as illustrated in FIG. 6. The mixture was stirred for 30 minutes followed by sonication (Step 3b). Composite nanoparticles were filtered and freeze-dried to provide free-flowing nanoparticles.

Preparation of Tannin-Chitosan Composite 3-D Biofoams.

Figure 7:
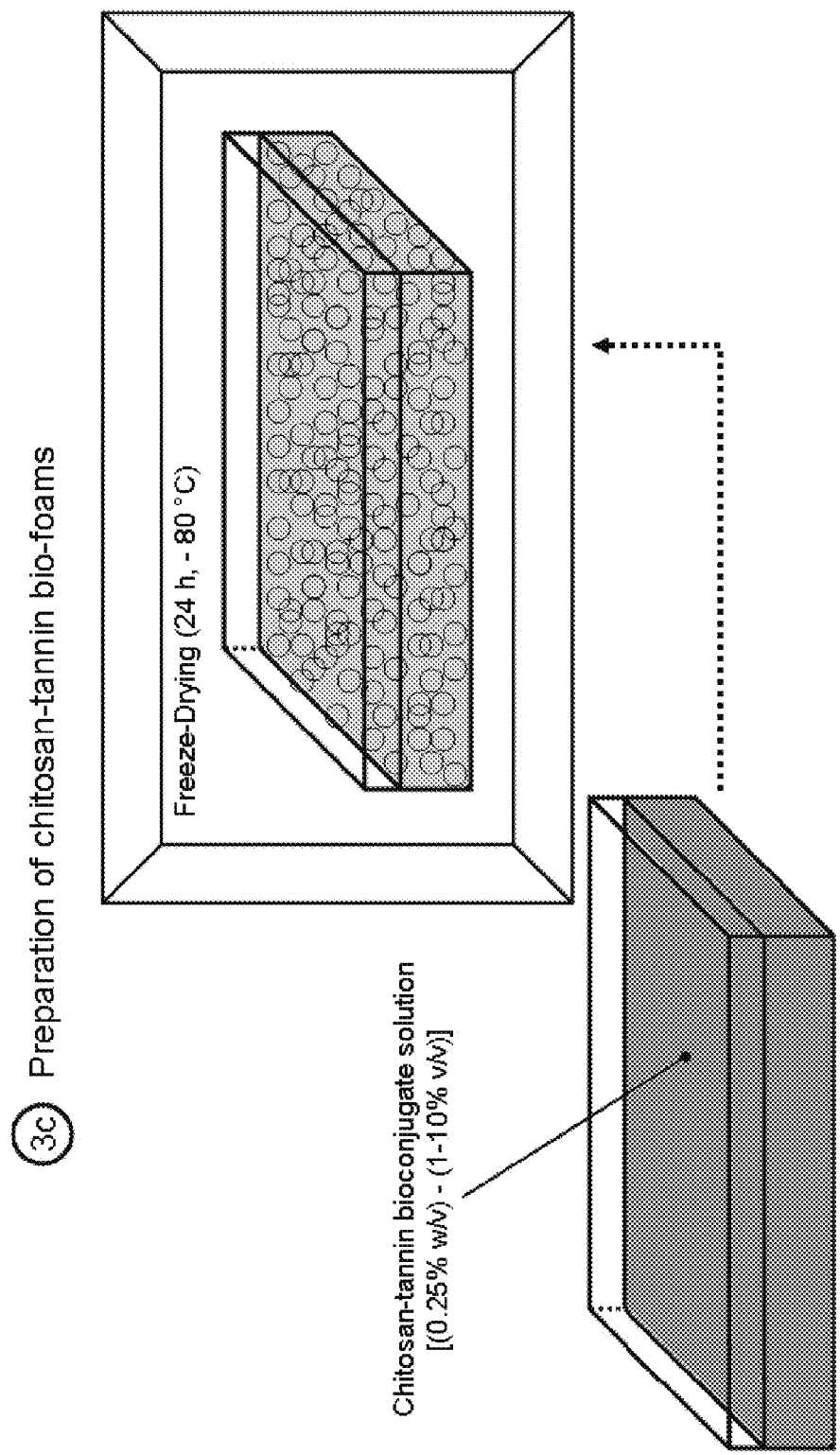
FIG. 7 illustrates the preparation of chitosan-tannin biofoams, according to an embodiment.

Composite foams (diameter=12 mm, thickness=6 mm) were prepared by casting/freeze-drying techniques (Step 3c). One gram of a 2% w/w chitosan solution in water or 0.5% v/v in acetic acid was mixed with tannins aqueous solutions (0.5-2.5% v/v), as illustrated in FIG. 7. The resulting mixture was poured into a cylindrical mold of adequate size, frozen at −20° C., and freeze-dried to eliminate the solvent, to provide the tannin-chitosan composite porous (3D) foam. The tannin-chitosan composite bio-foams are physically similar to known chitosan foams, however the composite bio-foams possess significant additional properties. The tannin-chitosan composite bio-foams can be used, for example, to provide improved wound and hemostatic (blood coagulation) dressings because the hemostatic effect of chitosan is increased by the immunostatic properties of tannin component.

Preparation of Tannin-Chitosan Composite Biogels.

Figure 8:
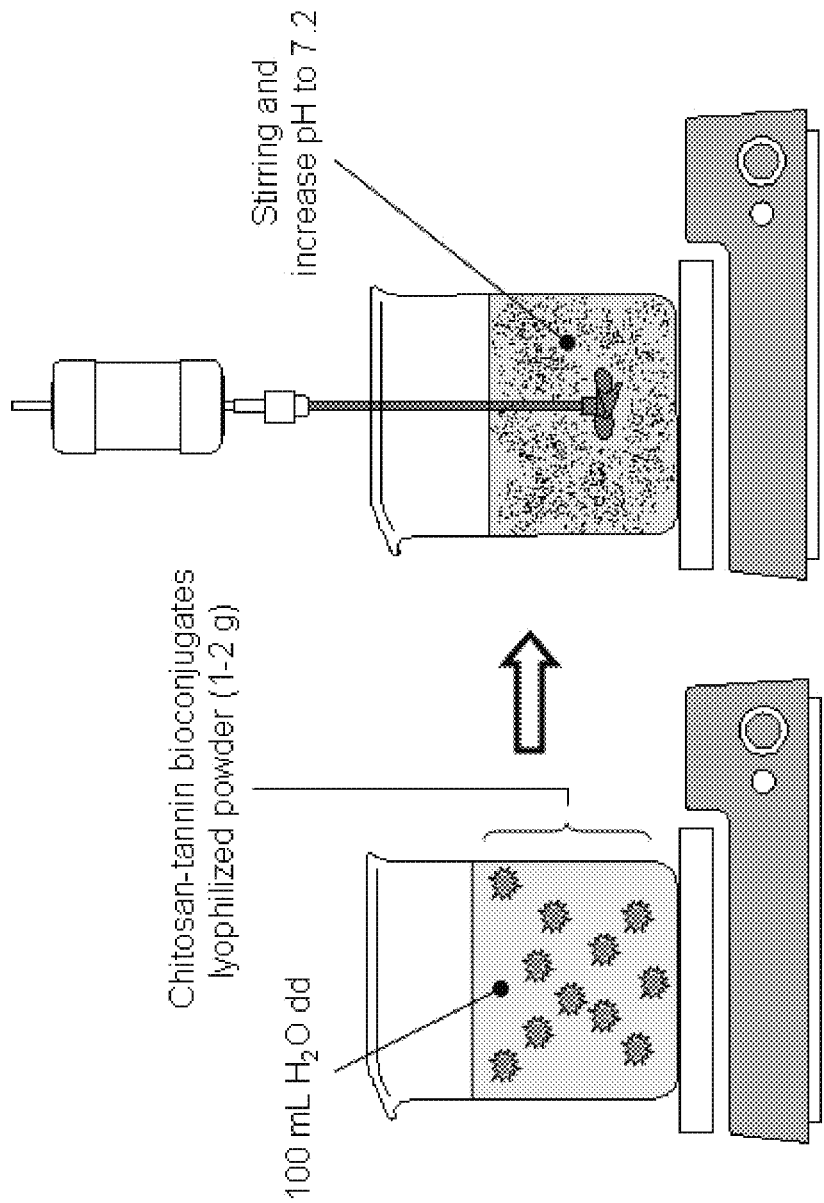
FIG. 8 illustrates the preparation of chitosan-tannin biogels, according to an embodiment.

A chitosan (1% w/v)-tannin (2% v/v) bioconjugate solution was frozen at −20° C. and freeze-dried to eliminate the solvent, leaving a pigmented powder material. One to two grams of the lyophilized chitosan-tannin bioconjugate was dissolved in 100 mL of distilled or deionized water and stirred vigorously while the pH was increased dropwise with a concentrated solution of NaOH 6N, as illustrated in FIG. 8. Once the solution reached an adequate pH value (~7.2), a bio-gel spontaneously formed and the viscosity of the dispersion significantly increased (Step 3*d*).

Physical and Chemical Characterization of Tannin-Chitosan Composites.

A Panasonic Hi-Star II X-ray diffractometer (XRD) was used to investigate the crystal structure of the synthesized tannin-chitosan composites. The X-ray source was Ni-filtered Cu—K$\alpha$ radiation (40 kV, 30 mA). A Perkin-Elmer DSC 7 differential scanning calorimeter (DSC) was used to evaluate the thermal properties of the chitosan and the chitosan-tannin bioconjugates (about 3 mg) under $N_2$ atmosphere at a heating rate of 20 K/minute from 50° C. to 400° C.

Figure 9:
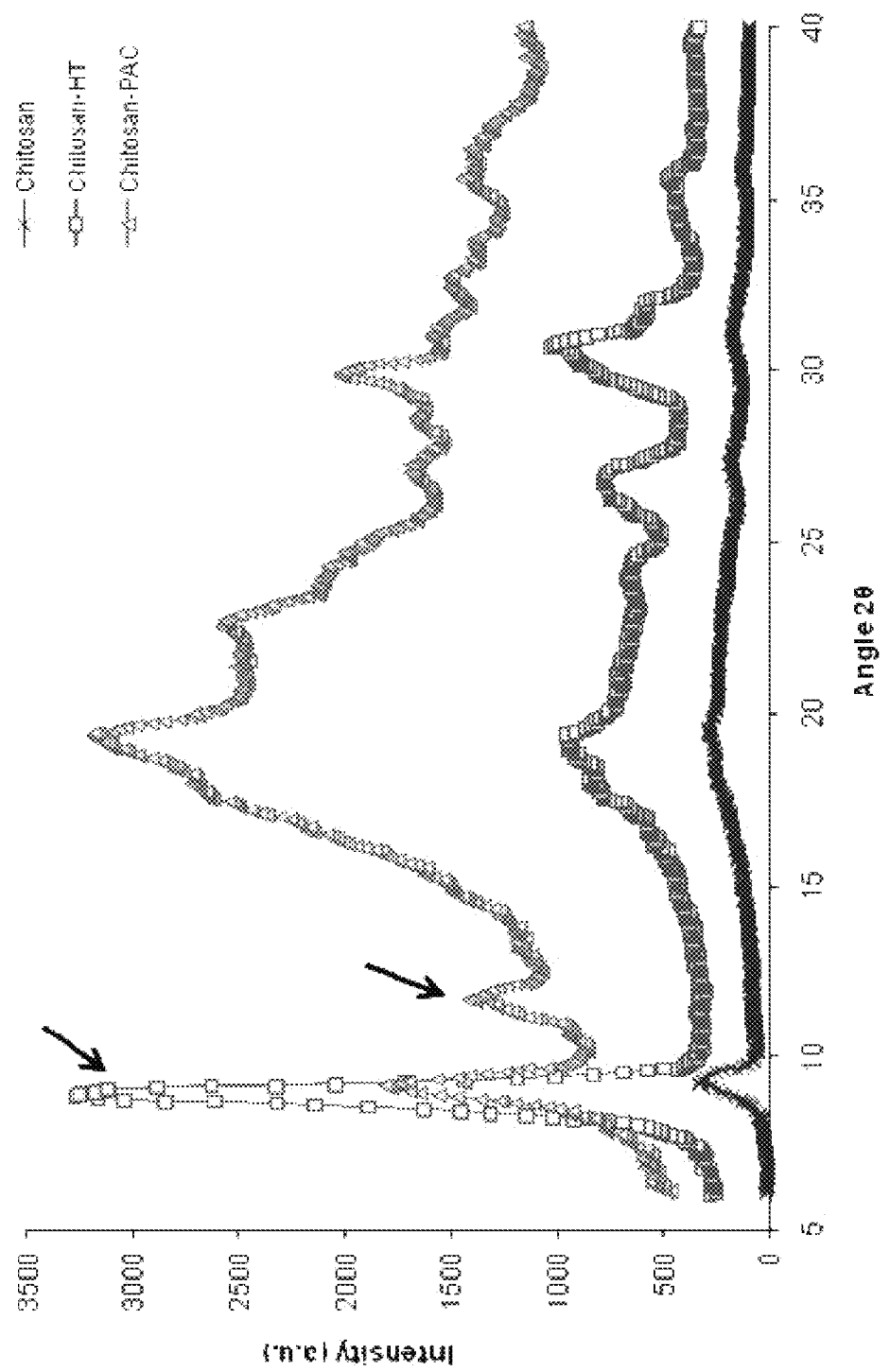
FIG. 9 illustrates X-ray diffraction patterns of chitosan and tannin-chitosan composites. Arrows indicate the most appreciable changes generated by the tannin component on the crystal arrangement of the biopolymer.

X-ray diffraction patterns of tannin-chitosan composites were compared with chitosan. FIG. 9 illustrates X-ray diffraction patterns of chitosan and tannin-chitosan composites. Arrows indicate significant changes generated by the tannin component on the crystal arrangement of the biopolymer. Results showed an increase on the crystalline structure of both HT and PA-chitosan composites, as indicated by the increase of the intensity of the crystalline segments at $2\theta=8°$ and $2\theta=12°$, respectively. Each peak represents a modification of the chemical structure of the main chitosan polymeric backbone that is related to either strong hydrogen bonding interaction or covalent bonding with the HT and PA Tannin.

Figure 10A:
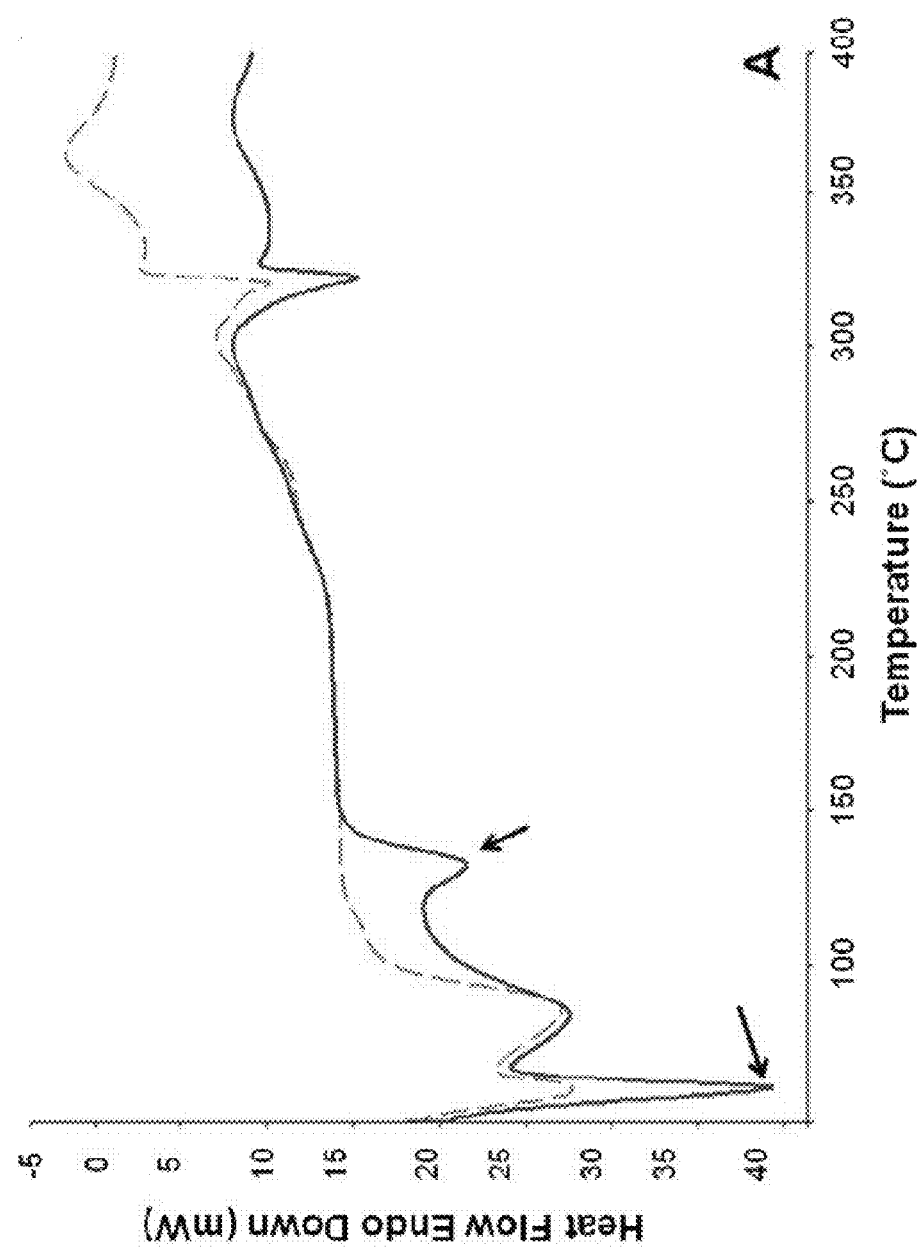
FIG. 10A illustrates HT-derived composites and FIG. 10B illustrates PA-derived composites. Arrows indicate significant changes on the thermal behavior of the composite material.
Figure 10B:
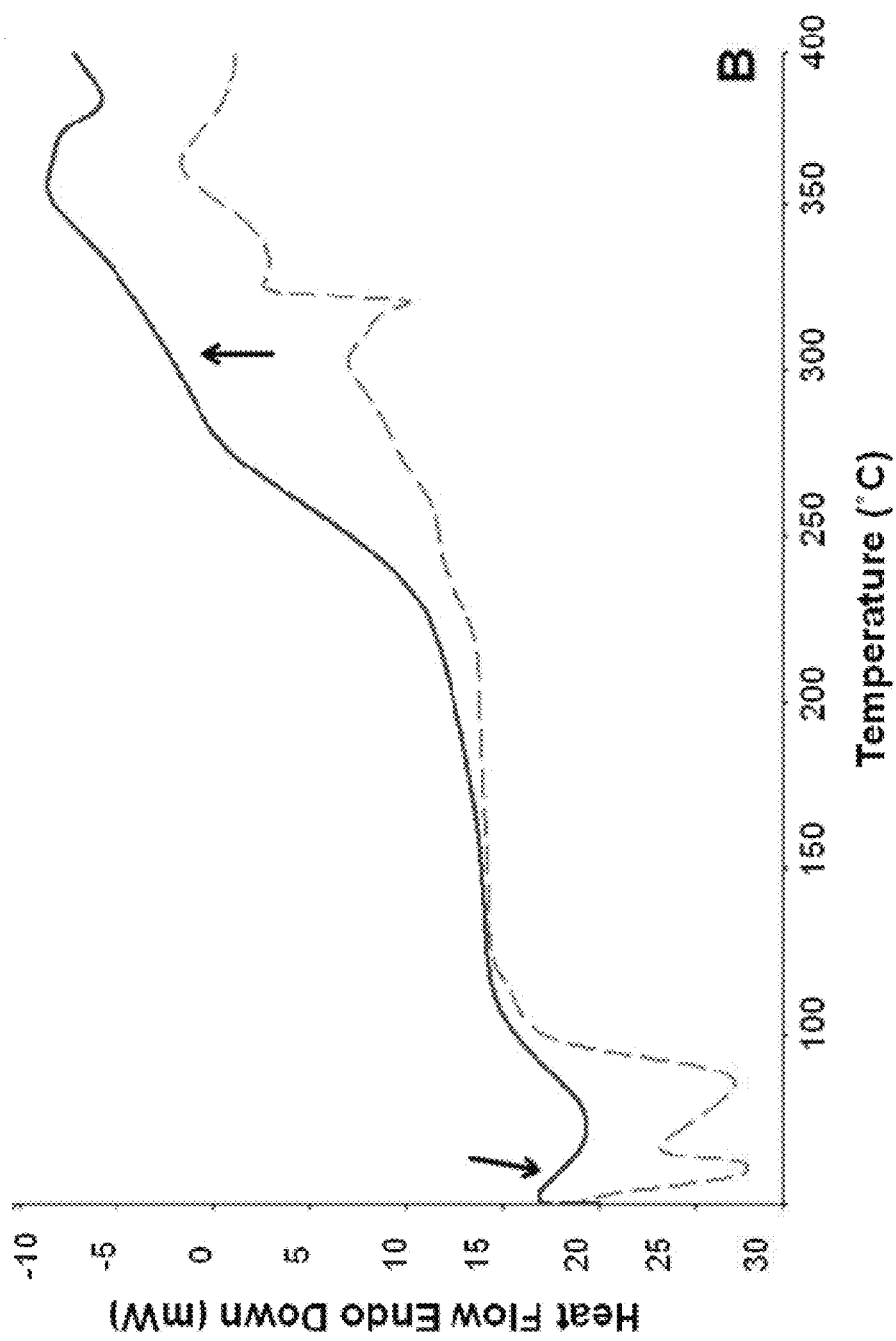

Thermal analysis of the tannin-chitosan composites by DSC showed new thermic transitions appearing for both PA tannin-chitosan and HT tannin-chitosan composites. FIG. 10 illustrates DSC thermograms of chitosan (top dashed line) and tannin-chitosan composites (bottom solid line). FIG. 10A illustrates HT-derived composites and FIG. 10B illustrates PAC-derived composites. Arrows indicate significant changes on the thermal behavior of the composite material. HT-chitosan composite showed an increase on the enthalpy associated with an endothermic transition at 50° C. and also a new endothermic transition appears at 130° C. Meanwhile, the PAC-chitosan composite showed a higher structural complexity that increases the rigidity of the biomolecule as shown by the disappearance of previously observed endothermic transitions of chitosan at 50° C. and 320° C. Both DSC thermograms for chitosan-tannin bioconjugates indicated a change in the main polymeric network due to the addition of the tannins, directly affecting the thermal stability of the macromolecule.

X-ray diffraction and DSC thermograms provided clear evidence of the formation of a new stable composite biomaterial. These analytic tools can be used to aid further optimization of processing and formulation of the new tannin-chitosan composites to meet desired physical chemical properties.

Characterization of Chitosan-Tannin Hydrogels (Films).

The mechanical properties of the tannin-chitosan composite hydrogels were evaluated by comparing tensile strength and swelling behavior. Swelling is the first step in the physical degradation of hydrogels. Rapid swelling promotes a rapid and uncontrolled release of active compounds (e.g., drugs and/or pesticides) from a hydrogel matrix. Glutaraldehyde is commonly added as a cross linking agent in the production of chitosan hydrogels to slow the rate of swelling. A disadvantage of using glutaraldehyde in a hydrogel formulation is a reduction in the tensile strength of the hydrogel.

Chitosan and PA- and HT-chitosan composite hydrogels were cast according to the previous described methodologies. In addition, 'crosslinked hydrogels' were formulated by first immersing pre-cast chitosan or tannin-chitosan composite hydrogels in a glutaraldehyde solution (0.10% v/v) for 30 minutes, followed by exhaustive washing with deionized water, followed by drying at 80° C. for 2 hours.

Mechanical Properties of Chitosan-Tannin Composite Hydrogels.

Tensile strength measurements were performed on a tensile testing machine (model TEST 108 from GT Test, France, equipped with Test Winner 920 software), with a crosshead speed of 10 mm/minute and a 2 kN static load cell. The hydrogels were cut into standard tensile samples from a dumbbell-shaped knife (H3 type) with a dimension 17 mm×4 mm×0.08 mm (length×width×thickness). At least five samples of each type of hydrogel were tested after a suitable storage period (3 and 20 weeks) at 50±3% RH and 23±2° C. in a humidity chamber (CIAT, France). The maximal tensile stress (TS) was calculated by dividing the maximum load for breaking film by cross-sectional area.

Figure 11:
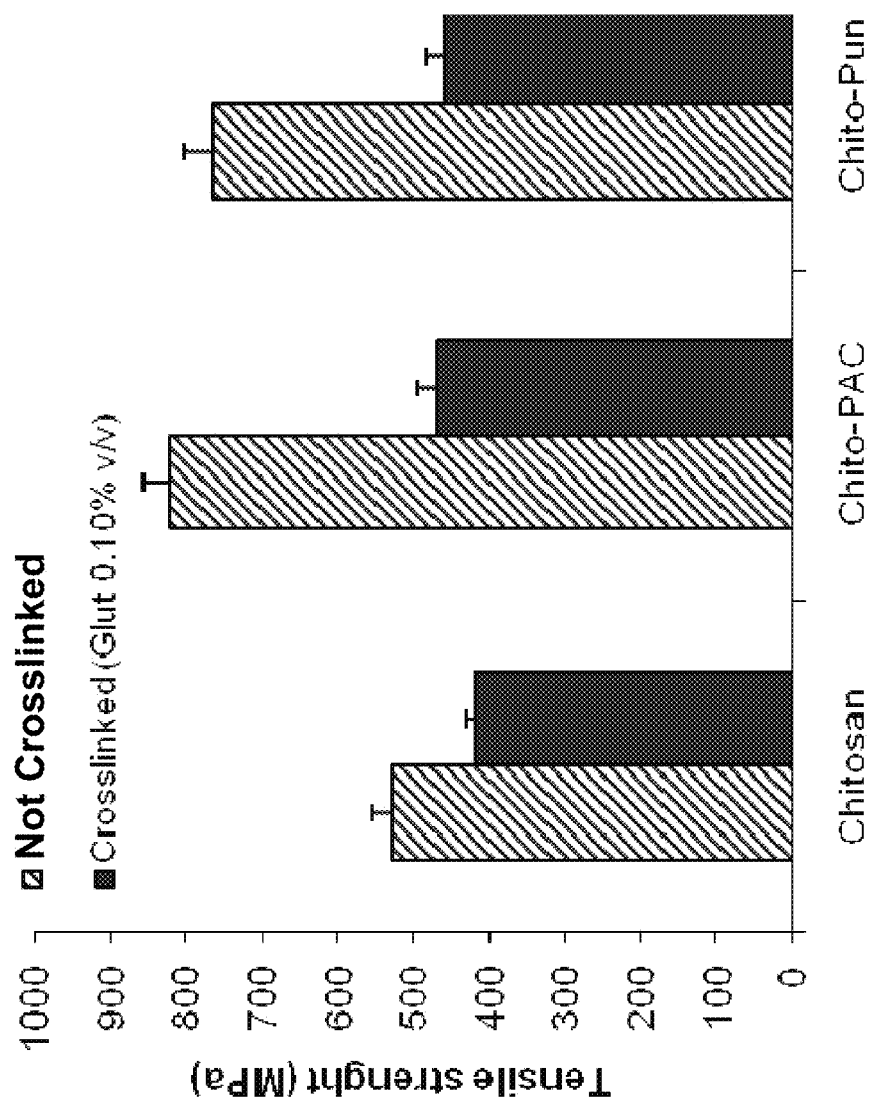
FIG. 11 illustrates the results of mechanical behavior tests of chitosan-tannin hydrogels compared to a chitosan hydrogel. Chito-PAC is a chitosan-proanthocyanidin composite; Chito-Pun is a chitosan-punicalagin composite. Data is shown as [mean±SD; n=5].

Both the PA-Chitosan composite hydrogel (no glutaraldehyde) and the HT-Chitosan composite hydrogel (no glutaraldehyde) showed higher tensile strength than the chitosan hydrogel alone (no glutaraldehyde). FIG. 11 illustrates the mechanical behavior of chitosan-tannin hydrogels compared to a chitosan hydrogel. Data is shown as [mean±SD; n=5]. The addition of a crosslinking agent (glutaraldehyde) reduced tensile strength of all hydrogels relative to the non-crosslinked hydrogels. There was no observed difference in tensile strength between crosslinked chitosan hydrogels and crosslinked tannin-chitosan composite hydrogels.

Evaluation of Swelling Behavior.

The degree of swelling of chitosan and tannin-chitosan hydrogels was evaluated by gravimetric methods. Each dry hydrogel was first weighed on an analytic balance (Wd). After weighing, hydrogels were submerged in distilled water for 60 minutes at room temperature. Hydrogels were then removed from the water and weighed (Ws) at 5, 10, 20, 30, 40, 50, and 60 minutes. Prior to being weighed on a high precision balance, each film sample was quickly taken out from the water bath and blotted with tissue paper to remove excess water. After weighing, the hydrogels were returned to the water. The degree of swelling (%) of each film sample was then calculated according to the following equation:

$$\text{Degree of swelling (\%)} = \frac{W_s - W_d}{W_d} \times 100. \qquad (2)$$

Figure 12:
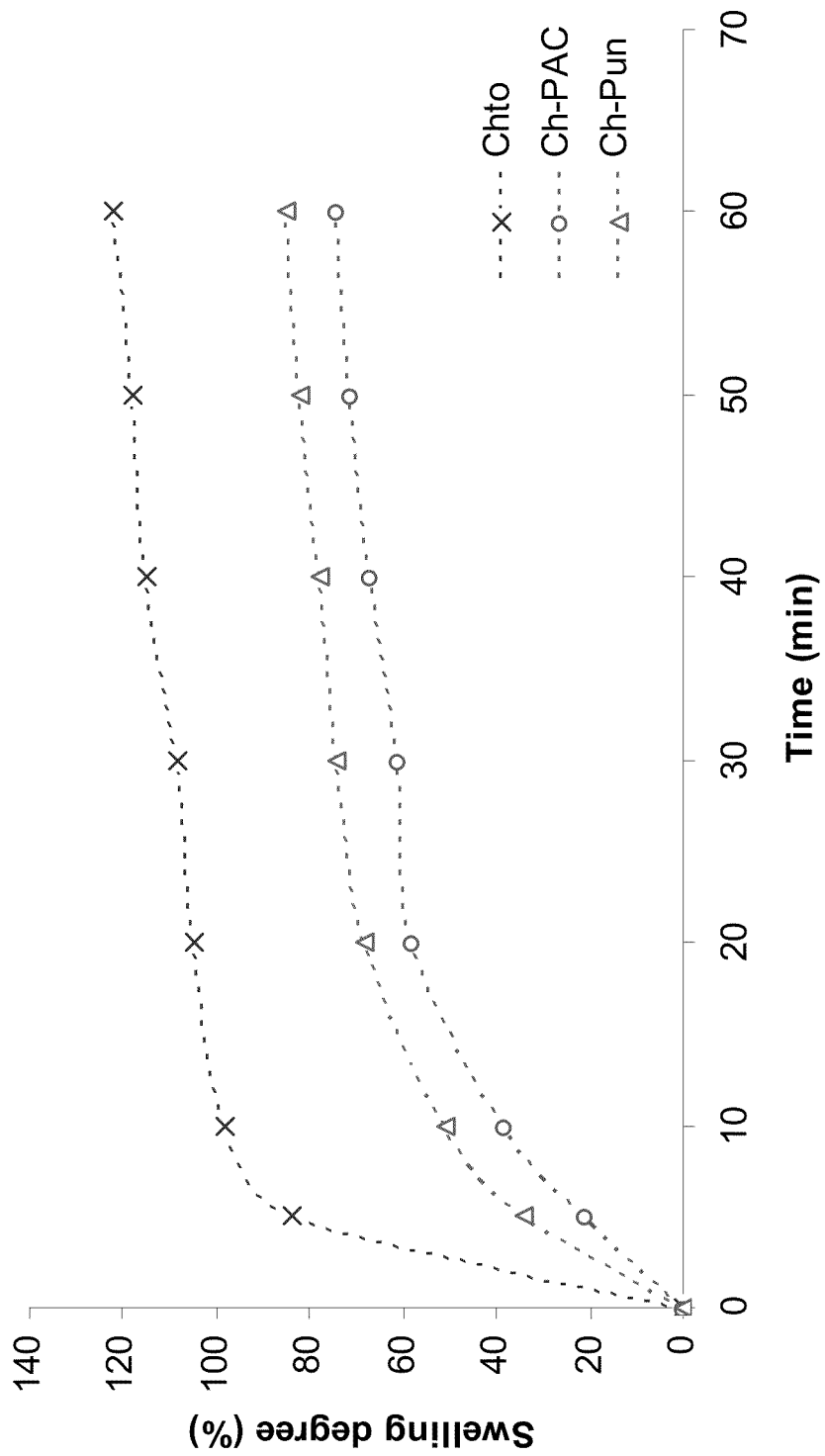
FIG. 12 illustrates the degree of swelling in water for a chitosan hydrogen (Chto) and chitosan-tannin hydrogels (Ch-PAC and Ch-Pun) as a function of time.

The results indicate that both PA and HT Tannin-Chitosan composite hydrogels, with no glutaraldehyde crosslinking agent, showed lower rates of swelling and lower total degrees of swelling compared to chitosan hydrogels with no crosslinking FIG. 12 illustrates the degree of swelling for the chitosan-tannin hydrogels as a function of time.

These results indicate that tannins act as a strong crosslinking agent or the equivalent thereof, reducing the swelling of the composite materials while improving the tensile strength of the hydrogel. The properties provided by tannins were superior to those of a glutaraldehyde crosslinking agent in chitosan hydrogels. Tannins are therefore suitable, reliable, and biocompatible 'green alternatives' to glutaraldehyde for formulating hydrogels for packaging, patching, and surgical biomaterials.

Characterization of Chitosan-Tannin Nanoparticles.

Size and Zeta Potential.

Size determinations and electrophoretic mobility measurements were carried out with a Z-Meter Zetasizer 2000 from Malvern Instruments and also with a Z-Meter System 3.0 from Z-Meter USA equipped with microscope model DR from Carl Zeiss and an electrophoresis cell GT2 type. For size and electrophoretic mobility measurements, the samples were obtained as stated above and afterwards diluted to 1:10 with deionized water. Five samples were prepared for each tannin-chitosan composite ratio. The error was the highest standard deviation for the five samples. For illustrative purposes, approximate ζ-potential values were calculated starting from the Smoluchowski's equation, and using the following values: $\epsilon_o = 8.9 \times 10^{-12}$ Fm$^{-1}$ and $\epsilon_r = 79$.

The results shown in Table 1-1 indicate that both particle size and ζ-potential of the chitosan nanoparticles (ChNp) increased as a function of the biopolymer concentration, showing a critical concentration around 0.15% w/v. After this value ChNp appears to suffer coalescence and aggregate, as indicated by the drastic increase on particle size after 0.10% w/v. According to this observation, chitosan-PA tannin nanoparticles (ChPANp) and chitosan-HT tannin nanoparticles (ChHTNp) where formulated holding the concentration of chitosan solutions (0.10% w/v) constant and varying the amount of tannin (5%, 10%, and 20%).

TABLE 1-1

Variation in size and ζ-potential for different chitosan and chitosan-tannin nanoparticle formulations. Results are shown as [mean ± SD, n = 5].

| Sample ID | Study | Size (nm) | ζ-Potential (mV) | Size (nm)* |
|---|---|---|---|---|
| ChNp 0.05% | Effect of chitosan | 130 ± 1 | 19.6 ± 0.9 | 152 ± 3 |
| ChNp 0.10% | concentration | 149 ± 1 | 20.9 ± 1.9 | |
| ChNp 0.20% | | 426 ± 28 | 32.2 ± 1.6 | |
| ChHTNp 5% | Effect of HT | 165 ± 4 | 24.4 ± 0.5 | 165 ± 2 |
| ChHTNp 10% | concentration | 167 ± 3 | 22.8 ± 1.5 | |
| ChHTNp 20% | (chitosan 0.1% w/v) | 165 ± 4 | 22.6 ± 2.5 | |
| ChPANp 5% | Effect of PA | 298 ± 7 | 23.2 ± 3.1 | 298 ± 3 |
| ChPANp 10% | concentration | 296 ± 2 | 21.5 ± 1.0 | |
| ChPANp 20% | (chitosan 0.1% w/v) | 292 ± 4 | 20.6 ± 0.9 | |

*Size of nanoparticles after being reconstituted in water following lyophilization.

ChPANp and ChHTNp size and ζ-potential were not affected by the tannin concentration. This observation indicates an intermolecular interaction between the components and not simply a physical adsorption on the surface structure of the biopolymer that increased the size and changed the ζ-potential of the nanoparticles. Nanoparticle size after lyophilization and reconstitution in water were not significantly different from original particle size, indicating that these biomaterials can be stored and marketed in powder form.

ζ-Potential is an important parameter for stability in aqueous nanosuspensions. For a physically stable nanosuspension, solely stabilized by electrostatic repulsion, a ζ-potential of ±30 mV is required as a minimum. All data indicated that tannin-chitosan composite nanoparticles are stable and can be dried by lyophilization without changing the average particle size.

Surface and Morphology Analysis.

The nanostructure of CNp, CPANp and CHTNp were examined on a JEOL JSM-5200 transmission electron microscope (TEM) with a tilt angle of 30° and by atomic force microscopy (AFM) on an Asylum Research AFM equipped with 3D imaging software.

Figure 13:
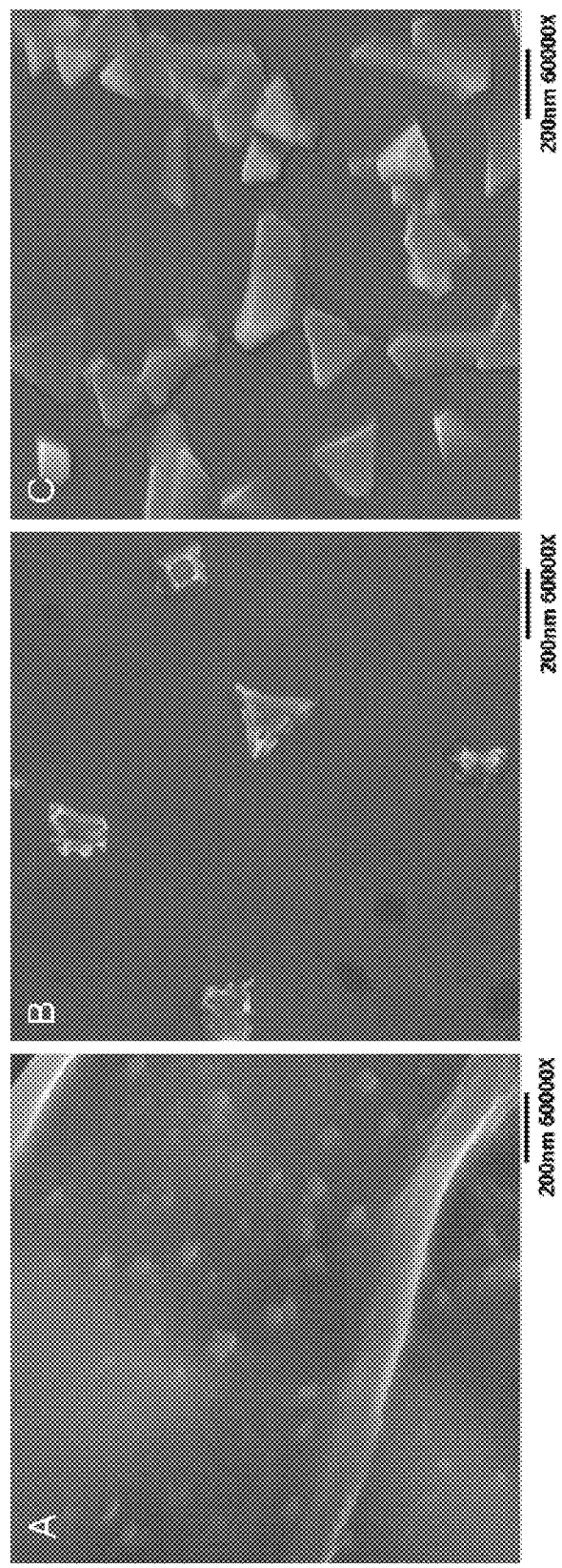
FIG. 13 illustrates scanning electron microscopy (SEM) micrographs for chitosan and chitosan-tannin nanoparticles: 13A: Chitosan Nanoparticles (ChNp); 13B: Chitosan Proanthocyanidin Nanoparticles (ChPANp); and 13C: Chitosan Hydrolysable Tannin Nanoparticles (ChHTNp). Scale bar indicates 200 nm.

Results of the surface and morphology analysis confirmed the presence of nanometric particles for both chitosan and tannin-chitosan composite systems. FIG. 13 illustrates scanning electron microscopy (SEM) micrographs for chitosan and chitosan-tannin nanoparticles: 13A: ChNp; 13B: ChPANp; and 13C: ChHTNp. The scale bar indicates 200 nm. These SEM micrographs clearly show the appreciable increase in the crystalline structure of the tannin-chitosan composites (FIGS. 13B and 13C) compared to the amorphous chitosan nanoparticles (FIG. 13A).

Chitosan nanoparticles are significantly smaller than the tannin-chitosan nanoparticles. Additionally, TEM micrographs show agglomeration of chitosan nanoparticles, indicated by white, cloudy areas on the TEM micrographs (data not shown), indicating instability of the chitosan nanoparticles. Tannin-chitosan nanoparticles showed consistent shapes and homogeneous size distributions that confirm their superior physical performance and stability.

Analysis of atomic force microscopy (AFM) micrographs confirmed that the particle size and surface characteristics of the tannin-chitosan composites are similar when compared with the standard chitosan nanoparticles. AFM micrographs show that when chitosan is complexed to tannins, there is a change in both shape and surface/distribution behavior compared to chitosan nanoparticles. Chitosan-TPP nanoparticles are typically spherical and lack agglomeration (due to surface charge repulsions), whereas chitosan-tannin-TPP nanoparticles showed crystalline forms that trend to agglomerate via hydrogen bonding, indicating an increase in surface polarity due to the presence of the tannins The increase in crystalline structure of the tannin-chitosan composites provides several advantages, including improved performance of the tannin-chitosan composites as carriers for therapeutic agent or pesticide applications.

Bacteriostatic and Fungistatic Action of Tannin-Chitosan Composite Nanoparticles.

*Botrytis cinerea*, also referred to as grey mold or *botrytis* bunch rot, has an economic impact on soft fruits such as strawberries and grapes. *Fusarium oxysporum* causes *Fusarium* wilt disease in more than a hundred species of plants, resulting in leaf wilting, yellowing, and eventually plant death. *Erwinia carotovora* is a bacteria that infects a variety of vegetables, such as carrots, potatoes, cucumbers, onions, tomatoes, and lettuce, in fields or in storage, causing plant tissues to become soft and watery, which eventually deteriorate and become foul-smelling. *Xanthomonas* is a bacteria that affects many types of commercial plants, such as citrus, beans, grapes, cotton, and rice, causing lesions on the leaves, fruit, and stems, as well as twig dieback.

Figure 14:
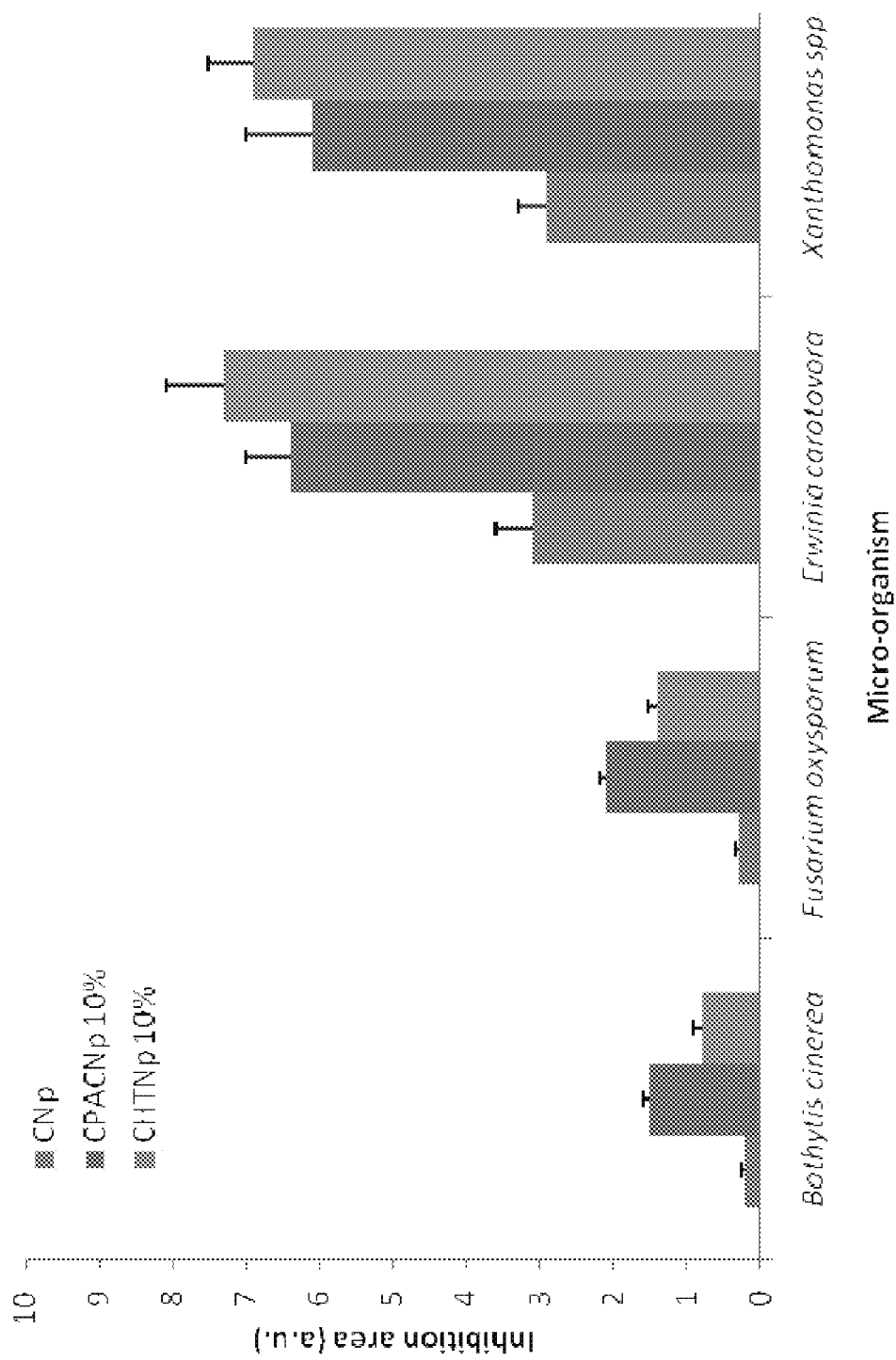
FIG. 14 illustrates the antimicrobial susceptibility test of tannin-chitosan composites against common Costa Rican agricultural pathogens, according to certain embodiments. Data is shown as mean±SD; n=3. CNp (left bar for each bar group) refers to chitosan nanoparticles; CPACNp 10% (middle bar) refers to chitosan-proanthocyanidin nanoparticles (90 wt. % chitosan, 10 wt. % cranberry tannin; and CHTNp 10% (right bar) refers to chitosan-hydrolysable tannin nanoparticles (90 wt. % chitosan, 10 wt. % hydrolysable tannin.

Chitosan-tannin composite nanoparticles were tested for their ability to prevent growth of agricultural pathogenic stains of fungi (*Bothytis cines* and *Fusarium oxysporum*) and bacteria (*Erwinia carotovora* and *Xanthomonas* spp.). Results indicate that both proanthocyanidin-chitosan nanoparticles (CPACNp) and hydrolysable tannin-chitosan nanoparticles (CHTNp) increase inhibition of all pathogens 2-3 fold compared to chitosan nanoparticles (CNp) alone. FIG. 14 illustrates the antimicrobial susceptibility test of these tannin-chitosan conjugate against common Costa Rican agricultural pathogens. Data is shown as [mean±SD; n=3].

Characterization of Chitosan-Tannin Composite 3-D Bio-Foams: Surface and Morphology Analysis.

Scanning electron microscopy (SEM) micrographs at 7 Kv showed excellent 3-D structures of the tannin-chitosan composites 3-D biofoams, confirming stability of composite material.

Advantages of Tannin-Chitosan Composite Biomaterials Compared to Chitosan Biomaterials.

The tannin-chitosan composite biomaterials provide significantly improved properties for a variety of applications, compared to chitosan biomaterials. The tannin-chitosan composite biomaterials can be prepared as nanoparticles, hydrogels such as bio-films, 3D-biofoams, or biogels. Each of these forms of biomaterials can be used for various target applications, and each the composite biomaterial has significant advantages over chitosan biomaterials, as summarized in Table 1-2 below.

TABLE 1-2

Improvements of Tannin-Chitosan Composite Biomaterials Compared to Chitosan Biomaterials.

| Biomaterial | Target application | Improvement using chitosan-tannin composites |
|---|---|---|
| Nanoparticles | Controlled drug release<br>Antimicrobial properties<br>Biodegradability | Tannin's crosslinking effect increases controlled released<br>Tannins impart bacteriostatic and fungistatic activity to nanoparticles<br>Tannins decrease the rate of biodegradation of the nanoparticles, an important property to promote sustained delivery |
| Hydrogels (bio-films) | Controlled drug release<br>Mechanical properties<br>Antimicrobial properties<br>Biodegradability<br>Wound healing | Tannin's crosslinking effect increases controlled released; can be a replacement for glutaraldehyde<br>Chitosan-tannin hydrogels showed an increase in tensile strength compared to chitosan; the composites are therefore suitable for dressing, patch, and packaging biomaterial applications<br>Tannin's increase the nanoparticles' interaction with bacteria and fungi<br>Tannins decrease the rate of biodegradation of the biofilms, an important property to promote sustained delivery<br>Tannin's immunostatic properties can increase a biofilm's performance as wound healing promoters |
| 3D-Biofoams | Antimicrobial properties<br>Biocompatibility<br>Wound healing and coagulation agent<br>Cell growth and tissue engineering | Tannins can increase bio-foam interaction with bacteria and fungi, thereby becoming more active and suitable as dermal patches or bandages<br>Tannin's immunostatic properties can increase biofoam performance as wound healing and coagulation promoters<br>Chitosan-tannin bioconjugate biocompatibility, antimicrobial properties, and porosity made them an advantageous scaffolding material for tissue engineering |
| Biogels | Biocompatibility<br>Additive biomaterial | Tannins are non-immunogenic and are suitable dietary supplements<br>Chitosan-tannin biogels can be readily used as additive biomaterials in various formulations (e.g., food, adhesives, pharmaceuticals, biomedical applications) due to their improved mucoadhesion and viscosity, as well as their antimicrobial and immunostatic properties |

Supporting information can be found in the following documents, which are incorporated herein by reference.

Afaq F., Saleem M., Krueger C. G., Reed J. D., Mukhtar H. 2005. Anthocyanin- and hydrolyzable tannin-rich pomegranate fruit extract modulates MAPK and NF-kappaB pathways and inhibits skin tumorigenesis in CD-1 mice. *Int. J. Cancer* 113 (3): 423-433.

Howell A. B., Reed J. D., Krueger C. G., Winterbottom R., Cunningham D. G., Leahy M. 2005. A-type cranberry proanthocyanidins and uropathogenic bacterial anti-adhesion activity. *Phytochem.* 66(18):2281-2291.

Krueger, C. G., M. M. Vestling and J. D. Reed. Matrix-assisted laser desorption/Ionization time-of-flight mass spectrometry of anthocyanin-polyflavan-3-ol polymers in cranberry fruit [*Vaccinium macrocarpon*, Ait.] and spray dried cranberry juice. ACS Symposium, Uncovering the Mysteries of Red Wine Pigments. Vol. 886: pp. 232-246. 2004.

Krueger, C. G.; Vestling, M. M.; Reed, J. D. Matrix-assisted laser desorption/ionization time-of-flight mass spectrometry of heteropolyflavan-3-ols and glucosylated heteropolyflavans in sorghum [*Sorghum bicolor* (L.) Moench)]. *J. Agric. Food Chem.* 2003. 53, 538-543.

Krueger, C. G., N. C. Dopke, P. M. Treichel, J. Folts, and J. D. Reed. 2000. Matrix-assisted laser desorption/ionization time-of-flight mass spectrometry of polygalloyl polyflavan-3-ols in grape seed extract. *J Agric. Food Chem.* 47: 3693-3701.

Ravi Kumar, M. N. V, Muzzarelli, R. A. A., Muzzarelli, C., Sashiwa, H. and Domb, A. J. 2004. Chitosan chemistry and pharmaceutical perspectives. *Chemical Reviews.* 104: 6017-6084.

Reed J. D., Krueger C. G., Vestling M. M. 2005. MALDI-TOF Mass spectrometry of oligomeric food polyphenols. *Phytochem.* 66(18): 2248-2263.

Rinaudo, M. 2006. Chitin and chitosan: Properties and applications. *Progress in Polymer Science.* 31:603-632.

Seeram, N. P., Zhang Y., Reed J. D., Krueger C. G., Yaya J. 2006. Pomegranate Phytochemicals. In Pomegranates (Medicinal and Aromatic Plants—Industrial Profiles). Editors: Seeram, N. P., Schulman, R. N. and Heber, D.

Example 2

Tannin-Chitosan Composites: Secondary Liposomes Stabilized by Electrostatic Deposition of Tannin-Chitosan Composites Liposomes are spherical bilayer vesicles formed by dispersions of certain polar lipids in aqueous solvents. Liposomes have attracted attention in the food and agricultural industries because of their ability to act as targeted release-on-demand carrier systems for both water- and oil-soluble functional compounds, such as antimicrobials, flavors, antioxidants, and bioactive ingredients (Benech et al. 2002; Were et al. 2003). Encapsulation of functional components in liposomes has been shown to increase their stability and maintain their activity in environments that typically lead to rapid degradation.

One major limitations of liposomes is that they have a tendency to leak and lose encapsulated components over time (Taylor et al. 2005). Gradual coalescence of liposomes may also occur. Coalescence becomes more pronounced in low pH environments where surface charges are reduced (Gregoriadis 1973; Gregoriadis 1993). Adsorption of a second layer onto the liposome, such as a tannin chitosan composite material as described herein, can improve the stability of liposomes and provide an inexpensive means to tailor the surface properties of liposomes. Additional layers (e.g., a third, fourth, and/or fifth layer) can be added to modify controlled release properties. These layers may alter between chitosan and tannin (PAC or HT) or they may be tannin-chitosan composites themselves, to provide different composition properties.

The electrostatic deposition of tannin-chitosan composites onto liposomes is an improvement over current compositions because tannin-chitosan composites are more biodegradable and biocompatible than currently used synthetic agents, such as polyethylene glycol and other polymers, in stabilization of liposomes. Tannin-chitosan composites also provide improved compositions because they impart valuable properties, such as anti-microbial and antioxidant properties, to the liposome in addition to improving the liposome stability. Tannin-chitosan composite coated liposomes can be used, for example, as diagnostic or therapeutic agents in contrast enhanced ultrasound.

Preparation of Secondary Liposomes Coated by Tannin-Chitosan Composites.

Secondary liposomes were prepared from concentrated soy lecithin dispersions according to procedures previously described (Madrigal-Carballo et al. 2007). Briefly, soy lecithin dispersions (250 g/L) were prepared by the slow-swelling-under-shear method in an aqueous medium ($10^{-5}$ M NaCl). Chitosan-tannin solutions ranging 0 to 10% v/v were produced from an aqueous solution of chitosan (0.10% w/v in acetic acid 0.5% v/v) complexed with cranberry proanthocyanidins (PAC) or pomegranate hydrolysable tannins (HT). Liposome/chitosan-tannin dispersions were prepared by diluting the previously prepared concentrated soy lecithin dispersions with the chitosan-tannin complexes solutions until a final concentration of 3 g/L was reached.

Size determinations and electrophoretic mobility measurements were carried out with a Z-Meter Zetasizer 2000 from Malvern Instruments and also with a Z-Meter System 3.0 from Z-Meter USA equipped with microscope model DR from Carl Zeiss and an electrophoresis cell GT2 type. All the ζ-potential values were approximated by the Smoluchowski's equation.

Influence of Chitosan-Tannin Concentration on Properties of Coated Liposomes.

Figure 15:
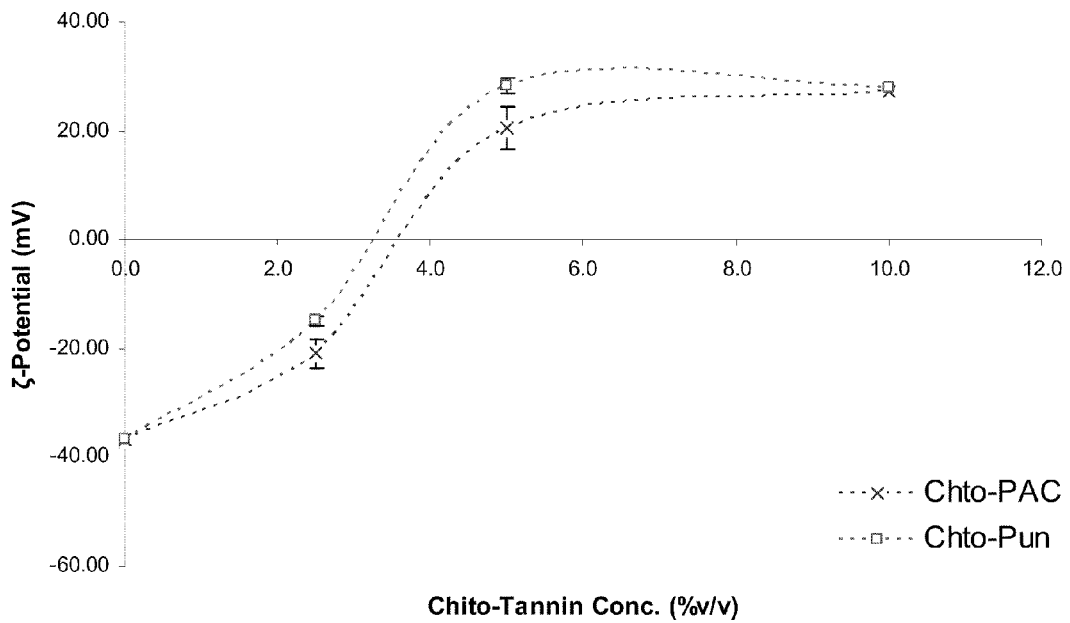
FIG. 15 illustrates the influence of addition of chitosan-tannin (0 to 0.5, w/v %) to liposomes (lecithin 0.4% w/v, 200 nm) on the ζ-Potential values of the vesicles.
Figure 16:
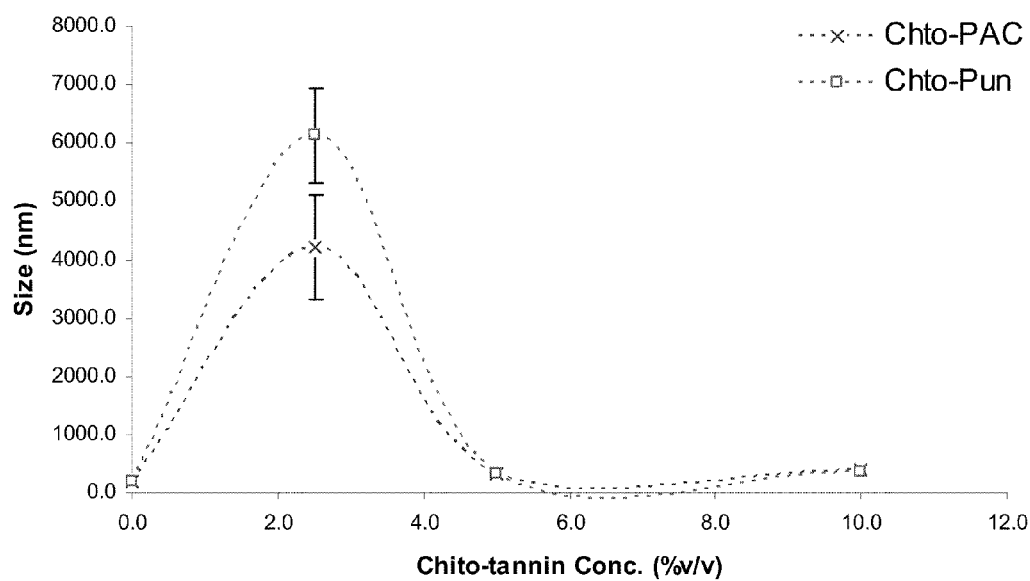
FIG. 16 illustrates the influence of the addition of chitosan-tannin (0 to 0.5, w/v %) to liposomes (lecithin 0.4% w/v, 200 nm) on the mean particle diameter of the vesicles.

The interaction between chitosan-tannin complexes and liposomes (d approximately 200 nm) was monitored by measuring the electrical charge and mean diameter of the particles in mixed liposome suspensions at pH 6 (FIGS. 15 and 16). FIG. 15 illustrates the influence of addition of chitosan-tannin (0 to 0.5, w/v %) to liposomes (lecithin 0.4% w/v, 200 nm) on the ζ-potential values of the vesicles. ζ-Potential measurements indicated that the uncoated liposomes were highly anionic (−38 mV), whereas the chitosan-tannin molecules were highly cationic (+82 mV). The surface charge of the particles in liposome suspensions (lecithin 0.4% w/v) increased from −38 mV to +30 mV with addition of chitosan-tannins (0% to 10% v/v).

The net charge on the particles was zero after addition of approximately 3% v/v chitosan-tannin complexes, indicating that charge neutralization occurred at this liposome-to-complex composition. The observed changes in surface charge suggest that chitosan-tannin complexes adsorbed to the surfaces of liposomes until the liposomal membrane was fully covered with the complex molecules thereby preventing further adsorption.

The mean diameter of the particles in the suspensions was highly dependent on the concentration of chitosan-tannin added to the system (FIG. 16). The particle diameter increased from around 200 nm in the absence of the complex to well above 4000 nm in the presence of low amounts of added chitosan-tannin complex (3% v/v), indicating the formation of large aggregated structures. These aggregates eventually phase separated and formed a precipitate at the bottom of the test tube. The range of chitosan-tannin concentrations where large aggregates was formed corresponded to the surface charge of the particles changing from approximately −20 mV to +20 mV, which suggested that this type of aggregation was caused by charge neutralization or possibly bridging (FIG. 15). At chitosan-tannin concentrations above 3% v/v, the particle diameter decreased to below about 500 nm to reach a minimum value at a chitosan-tannin concentration of 5% v/v. Further addition of chitosan led to steady increases in particle diameter. For example, the particle diameter was approximately 700 nm after addition of complex at 10% v/v.

Adsorption of Chitosan-Tannin onto Liposome Surfaces.

Electrostatic interactions between charged particles and charged biopolymers have been extensively studied, but there are few detailed investigations of the interaction of shell-structured liposomes with oppositely charged biopolymers. To this purpose, chitosan-tannins were added to liposomes under controlled conditions (rate of stirring, solution composition, temperature). The limitation of using charged biopolymers with too low or too high a molecular weight to form a stable biopolymer coating around liquid or solid particles has been previously explained in terms of the charge-mosaic theory, and a detailed explanation of the theory is described by Henriksen et al. 1997.

The results of the studies described herein indicate that liposomes interacted strongly with chitosan-tannins via electrostatic interactions to form a range of structures, depending on the ratio of chitosan-tannin to liposomes. Addition of a charged biopolymer to a dispersion of oppositely charged particles causes the electrical charge on the particles to change from either positive to negative, if particles are cationic and an anionic biopolymer is added, or vice versa if particles are anionic and a cationic biopolymer is added (Guzey and McClements 2007; Hong and McClements 2007; Pallandre et al. 2007). Stable chitosan-tannin coated liposomes were formed within only a narrow concentration range ($c_{min} < c < c_{max}$). Below and above this optimal range liposomes aggregated and eventually phase separated from solution (FIG. 16). The minimal concentration required to form stable secondary liposomes can be estimated from the change in ζ-potential with addition of chitosan-tannin complexes.

Stability of Liposomes Upon Addition of Chitosan.

Addition of chitosan-tannins to liposomes below and above the saturation concentration led to destabilization of the liposomal dispersions (FIGS. 15 and 16). The different structures that are observed when the concentration of chitosan-tannin was either too low or too high suggest that two different mechanisms can occur. At insufficient complex concentrations, liposomes completely broke down to rapidly (within minutes) form sediment at the bottom of the test tube. This could be because the anionic phospholipid molecules may have bound to the cationic chitosan-tannin molecules to form coacervates as opposed to the cationic chitosan-tannin molecules wrapping themselves around the surfaces of the liposome particles.

Figure 17:
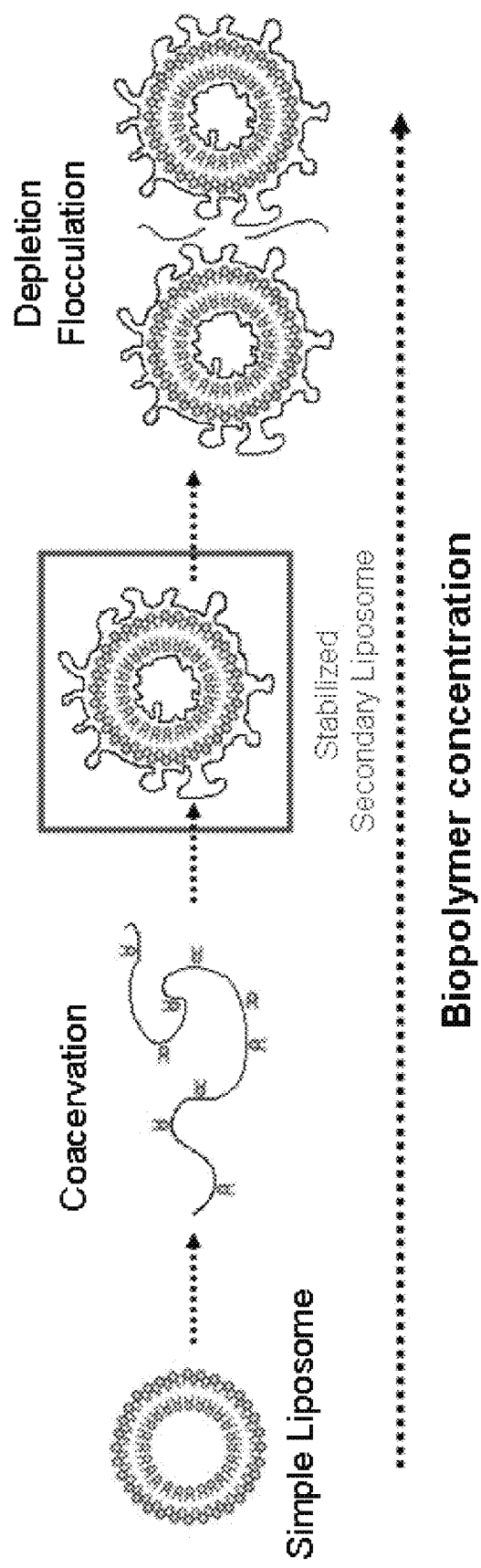
FIG. 17 illustrates the proposed mechanism of action for the addition of chitosan-tannin complexes to liposomes leading to coacervation, stable secondary liposomal dispersions, and bridging flocculation.

In the presence of excess concentration of complex, the mechanism may be similar to that found in emulsions where depletion flocculation may occur (Guzey and McClements 2006). The excess concentration of polymer may create an osmotic pressure gradient due to the exclusion of polymer molecules from the immediate vicinity of the particle surfaces, which generates at attractive force that increases with increasing complex concentration. At sufficiently high concentrations of non-adsorbed complex, this depletion attraction is sufficient to promote particle aggregation (McClements 2005). The model described herein for the observed instability phenomena upon addition of chitosan-tannin complexes to liposomes is shown in FIG. 17.

Supporting information can be found in the following documents, which are incorporated herein by reference.
1. Benech et al. 2002. Inhibition of *Listeria innocua* in Cheddar cheese by addition of nisin Z in liposomes or by in situ production in mixed culture. *Appl. Environ. Microbiol.* 68:3683-90.
2. Gregoriadis G. 1973. Drug entrapment in liposomes. *FEBS Lett.* 36:292-6.
3. Gregoriadis G. 1993. Liposome technology. 2nd ed. Boca Raton, Fla.: CRC Press.
4. Were et al. 2003. Size, stability, and entrapment efficiency of phospholipid nanocapsules containing polypeptide antimicrobials. *J. Agric. Food Chem.* 51:8073-9.
5. Taylor et al. 2005. Liposomal nanocapsules in food science and agriculture. *Crit. Rev. Food Sci. Nutr.* 45:1-19.
6. Guzey D, McClements D J. 2006. Formation, stability and properties of multilayer emulsions for application in the food industry. *Adv. Colloid Interface Sci.* 130:227-48.
7. Guzey D, McClements D J. 2007. Impact of electrostatic interactions on formation and stability of emulsions containing oil droplets coated by beta-lactoglobulin-pectin complexes. *J. Agric. Food Chem.* 55(2):475-85.
8. Henriksen et al. 1997. Interactions between liposomes and chitosan II: effect of selected parameters on aggregation and leakage. *Int. J. Pharm.* 146:193-204.
9. Hong and McClements. 2007. Modulation of pH sensitivity of surface charge and aggregation stability of protein-coated lipid droplets by chitosan addition. *Food Biophys.* 2(1):46-55.
10. Pallandre et al. November/December 2007. Improvement of stability of oil-in-water emulsions containing caseinate-coated droplets by addition of sodium alginate. *J. Food Sci.* 72(9):E518-E524.
11. McClements. 2005. Theoretical analysis of factors affecting the formation and stability of multilayered colloidal dispersions. *Langmuir* 21(21):9777-85.
12. Madrigal-Carballo et al. 2008. An approach to rheological and electrokinetic behaviour of lipidic vesicles covered with chitosan biopolymer. *Colloids Surf.*, A 323:149-154.
13. Madrigal-Carballo et al. 2009. Chitosomes loaded with cranberry proanthocyanidins attenuate the bacterial lipopolysaccharide-induced expression of iNOS and COX-2 in raw 264.7 macrophages. *J. Liposome Res.* 19(3): 189-196.

Example 3

In Vitro Uptake Study of Protein-Loaded Chitosan-Tannin Nanoparticles as Adjuvants for Oral Vaccination Novel vaccine adjuvants and particle-based delivery vehicles are being evaluated in a variety of vaccines, including those against diseases such as cancer, malaria, AIDS, and hepatitis, among others [1], in which a cellular and/or mucosal immune response is desired. The development of safe, novel adjuvants is necessary to maximize the efficacy of new and/or available vaccines. According to Gupta and Siber, an "ideal" adjuvant would elicit a persistent, high quality immune response to an antigen while being non-toxic, biodegradable, non-immunogenic, and chemically defined for reproducible manufacture [2].

Chitosan.

Chitosan is an abundant, natural linear polysaccharide derived by the deacetylation of chitin from crustaceans, insects, and fungi [16, 17]. Chitosan is non-toxic ($LD_{50} > 16$ g/kg [18]), biodegradable [19], non-immunogenic [16], and can be manufactured reproducibly in accordance with GMP guidelines. Chitosan's biodegradability, immunological activity, and bioadhesion, make it an excellent candidate as a depot/adjuvant for vaccination.

Over 20 years ago, chitin derivatives, including chitosan, were found to be potent activators of macrophages and NK cells [20, 21]. This immunostimulating activity along with the structural similarities between chitin derivatives and glucans, an immunoadjuvant class of natural polysaccharides, led several scientists to study the adjuvant capabilities of chitosan. Seferian and Martinez found that chitosan particles, formulated in an emulsion with antigen, squalene and Pluronic® L121, gave a prolonged, high antigen-specific antibody titer and sensitized animals for antigen-specific DTH responses following an IP injection.

Chitosan particles alone offered no enhancement of an adaptive immune response [22]. However, because of its mucoadhesive properties, chitosan has also been explored as an adjuvant for mucosal and subcutaneous vaccination [23]. Intranasal administrations of chitosan solutions have enhanced adaptive immune responses to several antigens [24, 25]. The mechanisms of vaccine enhancement by chitosan are believed to be due to both retention of vaccine in the nasal passages via mucoadhesion and opening of endothelial cell junctions for paracellular transport of vaccine [25]. Recent clinical studies have confirmed that chitosan is a promising adjuvant platform for intranasal vaccination [26-28].

Due to the high protein binding properties of some types of chitosan microparticles, they are also potential candidates for oral delivery of proteins and antigens [23]. Mild preparation can protect the proteins when they are incorporated during preparation of the microparticles [29, 30]. In order to circumvent protein denaturation conditions, chitosan microparticles can be loaded passively [31].

Tannin.

Tannins are oligomeric polyphenolic plant compounds that complex proteins and polysaccharides. Consumption of foods, beverages and nutritional supplements that contain tannins is associated with decreased risk of diseases which have an oxidative and microbial adherence etiology. However, the absorption of tannins from the gut is low. Greater than 95% of tannins are excreted in feces in complexes with proteins and polysaccharides from food or endogenous origins.

There are two groups of tannins: proanthocyanidins (PAC) and hydrolyzable tannins (HT). Examples of their chemical structures are shown in Schemes 1-4 above. Proanthocyanidins (PAC) are polymers of flavan-3-ols and flavans linked through an interflavan carbon bond, for example between carbon 4 of the C ring and carbon 8 of the A ring. Hydrolyzable tannins are gallic acid and ellagic acid esters of core molecules that consist of polyols such as sugars.

Chitosan-Tannin Nanoparticles.

By combining chitosan and tannin characteristics, specific, prolonged, and controlled release may be achieved [32]. Analysis of chitosan-tannin nanoparticles show that tannins increase rate of uptake of model proteins and modulate subsequent T-cell responses, indicating that tannin-chitosan nanoparticles can affect antigen presentation in GALT dendritic cells and macrophages. This Example describes a system that includes of a unique combination of two carriers. The system has been found to achieve both stability and slow release of entrapped antigens and its effect on macrophage uptake and antigen presentation is described.

Gut macrophages are maintained in a state of "inflammatory anergy" by cytokines, transforming growth factor β (TGF-β) and interleukin 10 (IL-10), secreted by epithelial and stromal cells of the lamina propria [43, 44]. However, activated macrophages in GALT are associated with inflammatory bowl disease and colon cancer, and activated macrophages in the oral cavity are associated with periodontal disease [39-42].

Tannins were isolated from cranberries (proanthocyanidins) and pomegranates (ellagitannins). The tannins were complexed to chitosan biopolymers to prepare chitosan-tannin nanoparticles (CTNp) via ionotropic gelation with tripolyphosphate (TPP). The CTNp were loaded with a model protein, such as bovine serum albumin (BSA), to determine the effects of these CTNp on macrophage endocytosis. Cell culture methods allowed for the determination of the effects of CTNp loaded with BSA, on macrophage uptake through microscopy of either fluorescently labeled biopolymer nor protein. Quenched BODIPY dye-labeled protein substrates were used to study post endocytosis proteolysis of BSA-loaded CTNp by direct fluorescence measurement [35].

Materials and Reagents.

All reagents were at least analytical grade. Chitosan (deacetylation degree of 92% calculated by $^1$H NMR; mean molecular weight of 185 kDa calculated by specific viscosimetry) was provided by the Polymers Research Laboratory (POLIUNA), National University, Costa Rica. Bovine serum albumin (BSA) [98% protein, Mw 66.3 kDa] and sodium triphosphate pentabasic (TPP) practical grade, 90-95%) were obtained from Sigma-Aldrich (St. Louis, Mo.) and were used without further purification.

Cranberry PAC Fraction.

Spray dried cranberry juice powder was reconstituted in $H_2O$ and applied to a preparative LH-20 column equilibrated in water. Water was passed through the column to elute non-phenolic cranberry constituents. Aqueous acetone (4:1, acetone: $H_2O$, v:v) was then passed through the column until it was white, to elute a crude cranberry PA fraction. The aqueous acetone fraction was concentrated by vacuum to remove the acetone. Its gallic acid equivalent (GAE) was calculated by Folin-Ciocalteau assay (GAE=33.4 mg GAE/mL). The Cranberry PAC fraction was identified by MALDI-TOF MS as having a degree of polymerization (DP) ranging from 4 to 7 with at least one A-type interflavan bond.

Pomegranate HT Fraction.

Nitrogen blended pomegranate peels (~5 g) were extracted with aqueous acetone 80% v/v, filtered, and concentrated by vacuum. The concentrated pomegranate extract was applied to a C18 preparative column equilibrated with water. Water was passed through the column to elute non-phenolic cranberry constituents. Aqueous methanol 50% v/v was then passed through the column until it was white, to elute a pomegranate HT fraction (GAE=4.13 mg GA/mL). MALDI-TOF MS and RP-HPLC analysis indicated that the pomegranate fraction was composed mainly of punicalagin (~95%).

Preparation of Chitosan-Tannin Nanoparticles (CTNp).

Chitosan nanoparticles were prepared based on the ionotropic gelation of chitosan with tripolyphosphate (TPP) anions. Chitosan was dissolved in acetic acid 1.00% v/v to obtain concentrations ranging 0.05-0.25% w/v. TPP was dissolved in water to a concentration of 1.00 mg/mL. Under magnetic stirring at room temperature, 2 mL of TPP solution were added dropwise to 5 mL of chitosan solution. The mixture was stirred for 60 minutes followed by sonication.

Chitosan-tannin nanoparticles (CTNp) where obtained by mixing chitosan nanoparticles (chitosan 0.10% w/v) with each tannin fraction in different volumetric ratios for 60 minutes at 25° C., as shown in Table 3-1. After mixing, the resulting suspension was subsequently centrifuged at 12000×g for 15 minutes. The precipitate was suspended in water, centrifuged again, and then freeze-dried. The freeze-dried CTNp were then resuspended in deionized water for further characterization and cell culture experiments.

TABLE 3-1

Composition of chitosan nanoparticles (CNp) and chitosan-tannin nanoparticles (CTNp) for delivery of antigenic hen-egg white lysozyme (HEL).

| Sample ID | Chitosan-TPP NP (μL) | PAC fraction (μL) | HT Fraction (μL) |
|---|---|---|---|
| CNp 0.05% | 5000 | 0 | 0 |
| CNp 0.10% | 5000 | 0 | 0 |
| CNp 0.25% | 5000 | 0 | 0 |
| CPACNp 5% | 4750 | 250 | 0 |
| CPACNp 10% | 4500 | 500 | 0 |
| CPACNp 20% | 4000 | 1000 | 0 |
| CHTNp 5% | 4750 | 0 | 250 |

TABLE 3-1-continued

Composition of chitosan nanoparticles (CNp) and chitosan-tannin nanoparticles (CTNp) for delivery of antigenic hen-egg white lysozyme (HEL).

| Sample ID | Chitosan-TPP NP (μL) | PAC fraction (μL) | HT Fraction (μL) |
|---|---|---|---|
| CHTNp 10% | 4500 | 0 | 500 |
| CHTNp 20% | 4000 | 0 | 1000 |

Size and Zeta Potential.

Size determinations and electrophoretic mobility measurements were carried out with a Z-Meter Zetasizer 2000 from Malvern Instruments, and with a Z-Meter System 3.0 from Z-Meter USA equipped with microscope model DR from Carl Zeiss and an electrophoresis cell GT2 type. For size and electrophoretic mobility measurements, the samples were obtained as stated above and were afterwards diluted to 1:10 with deionized water. Five samples were prepared for each chitosan-tannin ratio. The error was the highest standard deviation for the five samples. For illustrative purposes, approximate ζ-potential values were calculated starting from the Smoluchowski's equation, and using the following values: $\epsilon_o = 8.9 \times 10^{-12}$ Fm$^{-1}$ and $\epsilon_r = 79$.

Thermal Analysis and Transmission Electron Microscopy.

A Perkin-Elmer DSC 7 differential scanning calorimeter (DSC) was used to evaluate the thermal properties of the chitosan and the chitosan-tannin nanoparticles, under $N_2$ atmosphere at a heating rate of 20 K/min from 50° C. to 400° C. The nanostructure of CNp and CTNp was examined on a JEOL JSM-5200 transmission electron microscope (TEM) with a tilt angle of 30°.

Protein Loading and Release.

Bovine serum albumin (BSA) was used as a model protein. BSA loading of CNp and CTNp was performed by incubating Np 10% v/v and BSA 0.5-2.5% w/v in phosphate buffered saline (PBS; pH 7.3) under shaking at 25° C. After incubation for 180 minutes, the suspension was centrifuged (1400 rpm for 30 minutes) to remove the unloaded BSA. The loading degree was determined by quantifying the non-bound BSA in the supernatant with the Bradford protein assay. Both loading capacity (LC) and encapsulation efficacy (EE) were calculated as follows: LC=[(Total amount BSA−Free BSA)/Nanoparticles weight] and EE=[(Total amount BSA−Free BSA)/Total BSA].

BSA release from Np was determined in PBS (pH 7.3). To load the systems, 5.0 mL of Np 10% v/v containing 0.5% (w/v) BSA was incubated for 3 hours. After centrifuging (1400 rpm for 30 minutes) the loaded NP were resuspended in PBS (pH 7.3) to make a 1.0% w/v suspension. Samples were incubated at 37° C. under mild shaking After 15, 30, 45, 60, 90, 120, 180, and 240 minutes, the tubes were given a spin-off and samples of 500 μL of the supernatant were taken and replaced by 500 μL of PBS (pH 7.3). The non-bound HEL in PBS was determined with the Bradford protein assay.

Microscopy of Macrophage Endocytosis of BSA-Loaded CTNp.

RAW 264.7 macrophage-like cells were culture in 35 mm glass bottom culture plates (P35G-1.0-14-C, MatTek Corp., Ashland, Mass. 01721) and treated with BSA and the BSA-loaded CNp and CTNp. Endocytosis of the nanosystems was studied by fluorescent microscopy of labeled BSA (Alexa Fluor 488 Labeling Kit, Invitrogen/Molecular Probes, Eugene, Oreg.). Protein was labeled according to kit instructions and subsequently loaded into the Np according to the methodology described above. Macrophages were incubated with the labeled BSA and the BSA-loaded CNp and CTNp for 0.25-8 hours and imaged with a Zeiss fluorescent microscope (Carl Zeiss Microimaging, Thornwood, N.Y. 10594, with 450-490 nm excitation and 510-565 nm emission filters).

Results and Discussion.

Characterization of Chitosan-Tannin Nanoparticles (CTNp).

Particle size is one of the most significant factors associated with mucosal and epithelial tissue uptake of nanoparticles and in the intracellular trafficking of the particles. Smaller size nanoparticles (~100 nm) demonstrated more than 3-fold greater arterial uptake compared to larger nanoparticles, as the smaller nanoparticles were able to penetrate throughout the sub-mucosal layers while the larger size micron-particles were predominantly localized in the epithelial lining [43]. The size and ζ-potential variations among the chitosan and chitosan-tannin nanoparticles, formulated at different chitosan concentrations and chitosan to tannin volumetric ratios are shown in Table 3-2.

TABLE 3-2

Variation in size and ζ-potential for chitosan and chitosan-tannin nanoparticle formulations. Results are shown as mean ± standard error, n = 5.

| Sample ID | Size (nm) | ζ-Potential (mV) |
|---|---|---|
| CNp 0.05% | 130 ± 1 | 19.6 ± 0.9 |
| CNp 0.10% | 149 ± 1 | 20.9 ± 1.9 |
| CNp 0.25% | 426 ± 28 | 32.2 ± 1.6 |
| CHTNp 5% | 165 ± 4 | 24.4 ± 0.5 |
| CHTNp 10% | 167 ± 3 | 22.8 ± 1.5 |
| CHTNp 20% | 165 ± 4 | 22.6 ± 2.5 |
| CPACNp 5% | 298 ± 7 | 23.2 ± 3.1 |
| CPACNp 10% | 296 ± 2 | 21.5 ± 1.0 |
| CPACNp 20% | 292 ± 4 | 20.6 ± 0.9 |

Results show that both particle size and ζ-potential of the CNp increase as a function of the biopolymer concentration, with a high increase of about 35% fold in size and 65% fold in ζ-potential, between the 0.10 and the 0.25% w/v chitosan solutions. Meanwhile, CTNp prepared with pomegranate HT and cranberry PAC at a constant chitosan concentration of 0.10% w/v show relatively constant values for the CHTNp prepared at increasing volumetric ratios of HT (5-20% v/v). Each formulation increased with the increasing concentration of polymer solution, indicating the formation of a coating layer on the surface of the liposome. The mean size of chitosan (0.5%)-coated liposomes was double that of the free liposomes.

Results showed an increase in the particle size as a function of the increase in the chitosan concentration when preparing CNp. The mean size of the CNp formulated with chitosan 0.25 w/v was around 4 times larger than those formulated with chitosan solutions below 0.10% w/v. CTNp showed higher stability than CNp, indicating an effect of electrostatic stabilization driven by the chitosan-tannin interactions on the surface of the nanoparticles. The ζ-potential of the CNp was positive and was directly proportional to the concentration of biopolymer. A ζ-potential below ±30 mV is substantially necessary as a minimum for a physical stable nanosuspension solely stabilized by electrostatic repulsion [44]. The ζ-potential of the CNp showed values ranging 19 to 32 mV, whereas the CTNp showed stable ζ-potential values of around +25 mV for both CPACNp and CHTNp, confirming the effect of surface electrostatic stabilization.

The surface morphology of the CNp and CTNp was analyzed by ocular inspection of transmission electron microscopy (TEM) micrographs. The nanoparticles were spherical in shape with a relatively homogeneous size distribution.

Figure 18:
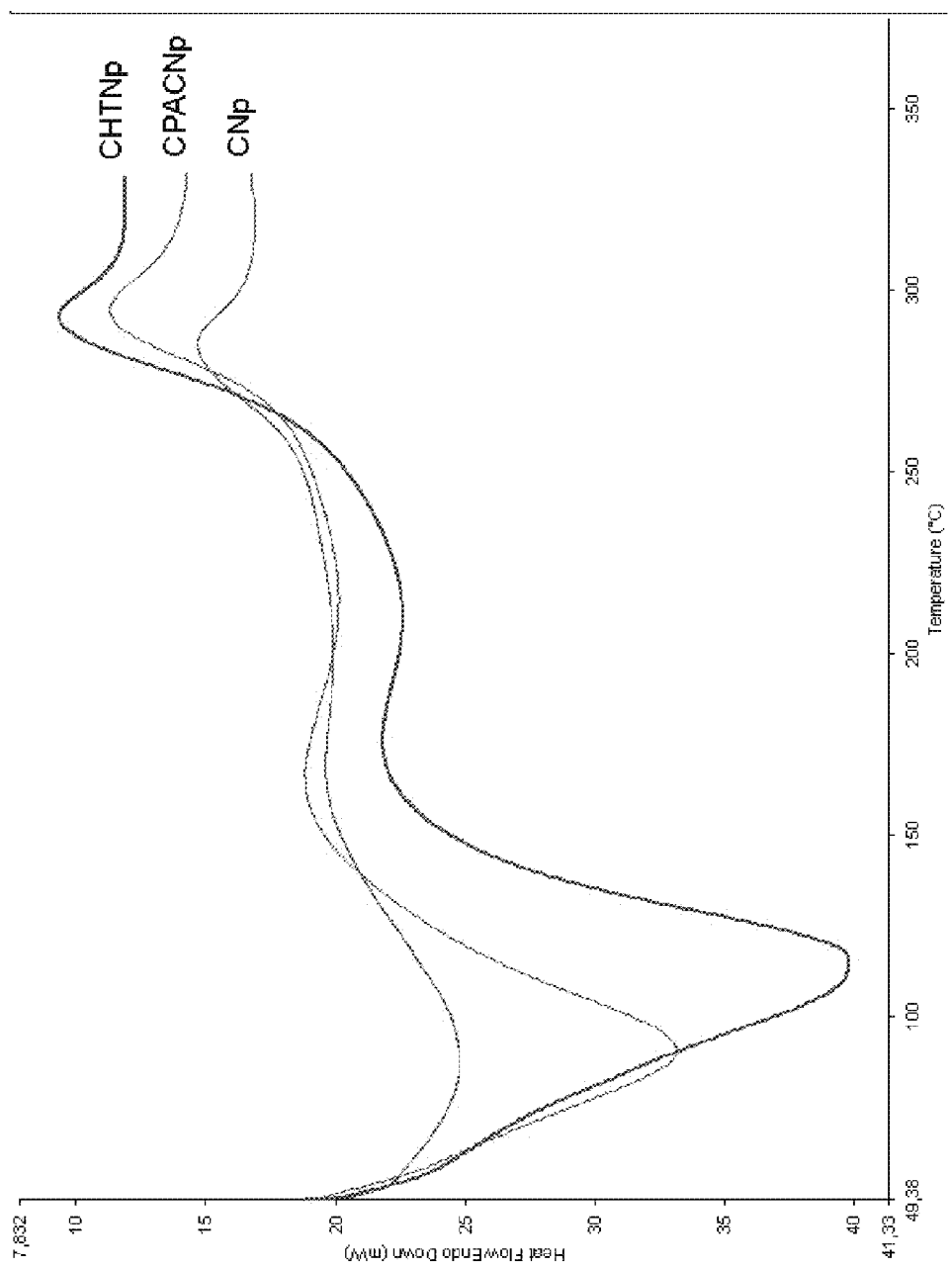
FIG. 18 illustrates differential scanning calorimetry thermograms for CNp and CTNp.

The DSC thermograms of CNp and CTNp (FIG. 18) presented an endothermic peak at around 100° C., attributed to the evaporation of water absorbed through hydrogen bonding. This endothermic peak depends on the nanoparticle composition, showing, for instance, a shift to high temperatures for the chitosan-tannin complexes, indicating an increase in hydrogen bonding driven by the increase in hydroxyl groups associated with the tannin moiety. An exothermic peak can be also observed for the CNp and CTNp at around 280° C., associated with chitosan degradation. This peak shows a shift to high temperatures when chitosan is complexed to tannins, indicating an increase in thermal stability due to chitosan-tannin interactions.

Protein Loading and Release.

The CNp were loaded with different amounts of bovine serum albumin (BSA) by incubation of CNp (chitosan 0.10% w/v) and CTNp (tannins 10% w/v) suspensions with 0.5-2.0% (w/v) BSA. Both encapsulation efficacy (LE) and loading capacity (LC) were determined. The data is illustrated in Table 3-3.

TABLE 3-3

Loading capacities and encapsulation efficiencies for loaded CNp and CTNp.

| | Loading Capacity | | | Encapsulation Efficacy | | |
|---|---|---|---|---|---|---|
| BSA Conc. (% w/v) | CNp | CHTNp | CPACNp | CNp | CHTNp | CPACNp |
| 0.50 | 61.2 ± 2.3 | 56.3 ± 1.7 | 52.2 ± 3.1 | 85.4 ± 3.6 | 86.9 ± 2.2 | 88.5 ± 2.4 |
| 1.00 | 58.7 ± 1.8 | 55.1 ± 1.3 | 51.5 ± 2.3 | 71.6 ± 2.7 | 79.8 ± 3.2 | 76.1 ± 2.7 |
| 1.50 | 60.3 ± 2.1 | 55.6 ± 1.9 | 52.7 ± 1.8 | 50.8 ± 2.4 | 60.1 ± 2.6 | 67.9 ± 3.1 |
| 2.00 | 56.2 ± 3.5 | 54.8 ± 2.0 | 51.9 ± 2.6 | 37.6 ± 3.1 | 44.5 ± 2.1 | 51.3 ± 2.9 |

The CNp and CTNp particles were loaded with bovine serum albumin. Results are shown as mean±standard error, n=3.

Results indicated that the LC is not substantially influenced by the amount of BSA available in the loading solution, but CTNp appear to have lower loading capacities than CNp. The encapsulation efficacies of CNp seems to be increased when chitosan is complexed with tannins This property may be associated with the increase in hydrogen bonding potential, as evidence by the DSC data. Therefore, BSA 1.0% w/v in the loading solution was selected as the optimal concentration. When CNp (0.10% w/v), CHTNp (10% w/v) and CPACNp (10% w/v) were incubated with 1.0% of BSA, loading percentages of 58.7, 55.1 and 51.5 for independently made batches were obtained, respectively. Under these conditions, a very high EE of 71.6, 79.8 and 76.1 was obtained, indicating that only a small amount of BSA was lost during the loading process.

Figure 19:
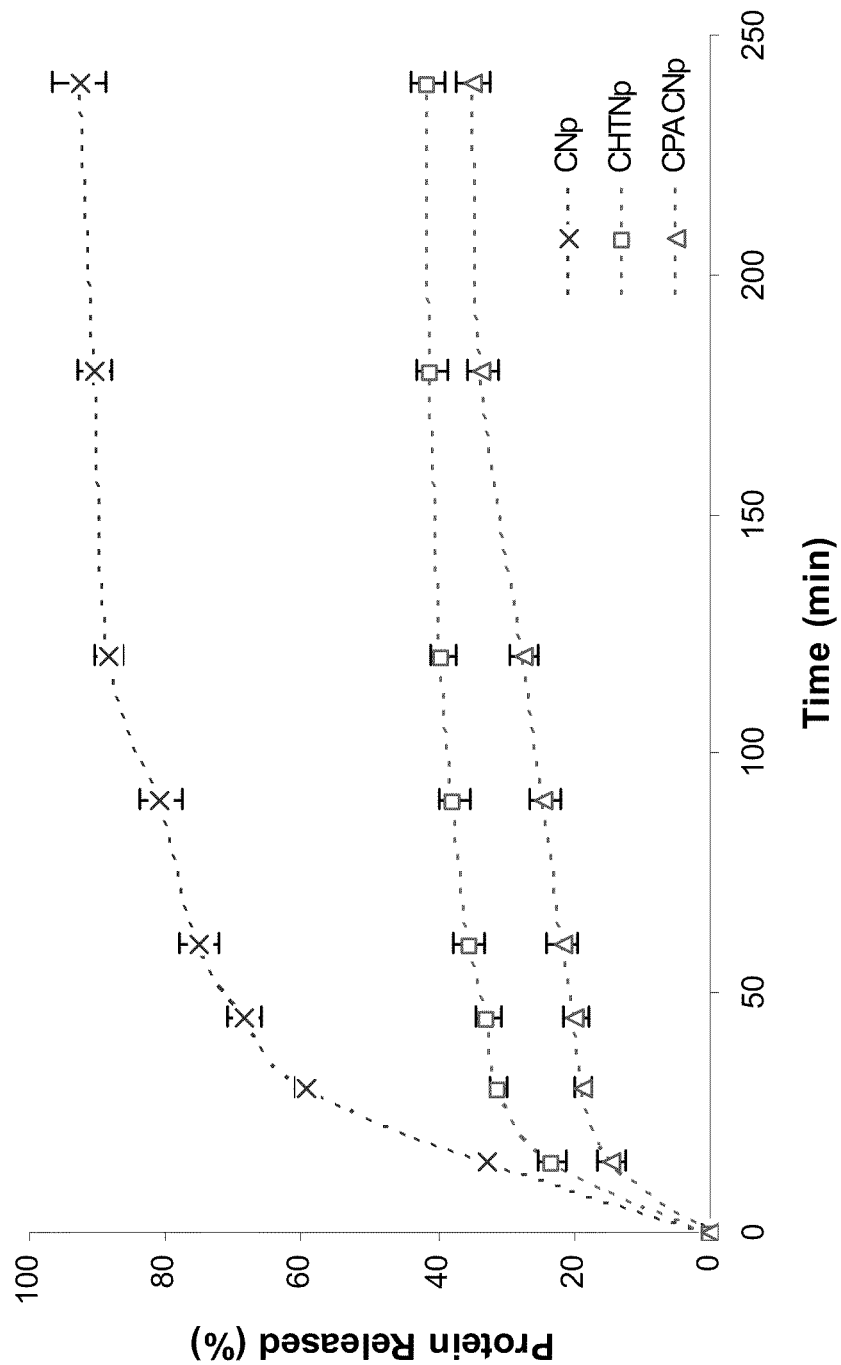
FIG. 19 illustrates bovine serum albumin release profiles from CNp and CTNp. Results are shown as mean±standard error, n=3.

Protein release studies showed that BSA total release at isothermal conditions, decreased significantly when the protein is delivered via CTNp. FIG. 19 illustrates bovine serum albumin release profiles from CNp and CTNp. Addition of tannins provided a greater crosslinking density within the biopolymer, causing increased packing and rigidity, as well as increased inter-chain bonding, thereby reducing BSA release over time from the nanoparticulate system.

BSA labeled with fluorescein was loaded into chitosan nanoparticles with and without complexation to tannins The nanoparticles were incubated with Raw 264.7 macrophages. Uptake of the nanoparticulate systems was followed by fluorescent microscopy. After 30 minutes, macrophages treated with CTNp clearly contained more fluorescent endosomes than the macrophages treated with the CNp alone.

In vitro studies showed that CTNp increases macrophage uptake of proteins, for example, BSA. Attenuation of gut macrophage activation by proteins loaded into CTNp is beneficial in treatment and prevention of gut related infectious diseases. These new biomaterials can therefore be used as adjuvants, for example, for oral vaccination. Because uptake by macrophage cells is the first step in vaccination, the results herein indicate that chitosan-tannin nanoparticles can be used as efficient adjuvants for a vaccine delivery systems. While vaccines in general provoke stronger immune responses than proteins such as BSA, the CTNp system can be loaded with a variety of vaccines against different pathologies.

In summary, chitosan binds to negatively charged tannins by an electrostatic interaction driven by its positively charged amino groups. This interaction allows for the preparation of stable nanoparticles via ionotropic gelation with tripolyphosphate (TPP), suitable as a targeted carrier and controlled release system for proteins, drugs and vaccines. The effect of chitosan-tannin nanoparticles (CTNp) on the uptake and release of bovine serum albumin (BSA) in Raw 264.7 macrophages was studied and described herein. CTNp were characterized according to size, zeta potential, and protein-loading and release properties. Results showed an increase in the positive net charge and size of the nanoparticles as the concentration of chitosan was increased, indicating an electrostatic interaction and a reliable covering, as determined by fluorescence microscopy. About 82% of the protein loaded remained in the CTNp after release studies for 4 hour in PBS. Confocal microscopy studies showed that CTNp had a higher uptake rate of the fluorescently labeled protein than chitosan nanoparticles without tannins (CNp) after 30 minutes of incubation with the macrophages. Because uptake by macrophage cells is the first step in oral vaccination, the CTNp system can be used as an oral vaccine delivery system.

Supporting information can be found in the following documents, which are incorporated herein by reference.

1. L. J. Peek, C. R. Middaugh, C. Berkland. *Adv. Drug Deliv. Rev.* 60 (2008) 915.
2. R. K. Gupta, G. R. Siber. *Vaccine* 13 (1995) 1263.
3. D. Mishra, P. K. Mishra, V. Dubey, S. Dabadghao, N. K. Jain. *Vaccine* 25 (2007) 6939.
4. G. Gregoriadis, R. Saffie, J. B. de Souza. *FEBS Lett.* 402 (1997) 107.
5. Bu et al., *Comp. Immunol. Microbiol. Infect. Dis.* 26(2003) 175.
6. Yoshikawa et al., *Biochem. Biophys. Res. Commun.* 325 (2004) 500.
7. Khatri et al., *Vaccine.* 26 (2008) 2225.
8. A. Saupe, W. McBurney, T. Rades, S. Hook. *Expert Opin. Drug Deliv.* 3 (2006) 345.
9. Alving et al. *Prog. Clin. Biol. Res.* 47 (1980) 339.
10. C. R. Alving. *J. Immunol. Methods* 140 (1991) 1.
11. Van der Lubben et al., *Biomaterials* 22 (2001) 687.
12. Nakanishi et al., *Control. Release.* 61 (1999) 233.

13. Y. Kato, T. Hosokawa, E. Hayakawa, K. Ito. *Biol. Pharm. Bull.* 16 (1993) 457.
14. Iwanaga et al., *J. Pharm. Sci.* 88 (1999) 248.
15. K. A. Janes, P. Calvo, M. J. Alonso. *Adv. Drug. Deliv. Rev.* 47 (2001) 83.
16. L. Illum. *Pharm. Res.* 15 (1998) 1326.
17. A. K. Singla, M. Chawla. *J. Pharm. Pharmacol.* 53 (2001) 1047.
18. K. Arai, T. Kinumaki, T. Fujita. *Bull. Tokai Reg. Fish Lab.* 43 (1968) 89.
19. H. Onishi, Y. Machida. *Biomaterials.* 20 (1999) 175.
20. Nishimura et al., *Vaccine.* 2 (1984) 93.
21. K. Nishimura, C. Ishihara, S. Ukei, S. Tokura, I. Azuma. *Vaccine.* 4 (1986) 151.
22. P. G. Seferian, M. L. Martinez. *Vaccine.* 19 (2001) 661.
23. Zaharoff et al., *Vaccine* 25 (2007) 2085.
24. Ilium et al., *Adv. Drug Deliv. Rev.* 51 (2001) 81.
25. Van der Lubben et al., *Adv. Drug Deliv. Rev.* 52 (2001) 139.
26. Read et al., *Vaccine.* 23 (2005) 4367.
27. Mills et al., *Infect. Immun.* 71(2003) 726.
28. McNeela et al., *Vaccine.* 22 (2004) 909.
29. Calvo et al., *J. Appl. Polym. Sci.* 16 (1997) 125.
30. A. Berthold, K. Cremer, J. Kreuter. *J. Control Release* 39 (1996) 17.
31. S. R. Jameela, T. V. Kumary, A. V. Lal, A. Jayakrishnan. *J. Control. Release* 52 (1998) 17.
32. J. Guo, Q. Ping, G. Jiang, L. Huang, Y. Tong. *Int. J. Pharm.* 260 (2003) 167.
33. Takeuchi et al., *Pharm. Res.* 13 (1996) 896.
34. Madrigal-Carballo et al., *Colloids and Surfaces A: Physicochem. Eng. Aspects.* 323 (2008) 149.
35. Jones et al., *Anal. Biochem.* 251 (1997) 144.
36. Alvarez et al., *J. Colloid Interface Sci.* 309 (2007) 279-282.
37. Manconi et al., *Coll. and Surfaces A: Physicochem. Eng. Aspects.* 270-271 (2005) 102.
38. O. Lowry, N. Rosebrough, A. Farr, R. Randall. *J. Biol. Chem.* 193 (1951) 265.
39. Czochanska et al., (1979): *Phytochemistry* 18:1819-1822.
40. Shanahan, F. (1994): The Intestinal Immune System. In Johnson, L. R., ed. *Physiology of the Gastrointestinal Tract.* New York: Raven Press, pp 643-684.
41. Stagg et al., (2003): *Gut* 52:1522-1529.
42. Tezuka et al., (2007): *Nature* 448:929-933.
43. Gan et al. *Colloids Surf B.* 2005; 44:65-73.
44. Muller et al., *Adv. Drug Deliv. Rev.* 2001; 47:3-19.

Example 4

Extraction of Cranberry Fruit Presscake to Obtain High Degree of Polymerization Proanthocyanidins The degree of polymerization, monomeric substitution, and nature of intermolecular bonds are 'proanthocyanidin variables' that can be controlled by choice of initial raw material (plants, fruits, juices), and extraction processes and enrichments by liquid and solid phase chromatography, including liquid/liquid (partition) chromatography and supercritical fluid extraction. Research indicates that high degree of polymerization proanthocyanidins are more bioactive in in vitro models of: 1) inhibition of copper induced oxidation of low density lipoprotein, 2) inhibition of *E. coli* invasion of mouse prostate epithelial cells, 3) inhibition of *E. coli* invasion of CaCo-2 cells, and 4) inhibition of COX-2 and iNOS production by macrophages in response to lipopolysaccharide stimulus. This research indicates the value of formulations of tannin (PAC)-chitosan composites containing PAC of higher degree of polymerization.

Described herein is a method for extracting PAC of higher degree of polymerization from cranberry fruit presscake. Presscake is the material that remains after fruit has been subjected to the juicing process. While the process described here was applied to cranberries, the methods developed can be applied to any fruit or presscake to obtain PAC of with unique monomeric substitutions, interflavan bonds, and/or degrees of polymerization. The processes can therefore be used to recycle material from juice processing waste streams by using them as source materials for tannin (PAC)-chitosan composites.

Methods.

Extraction of Cranberry Presscake.

Ten grams of cranberry presscake was homogenized in liquid nitrogen. The powdered material was extracted with 40 mL of aqueous acetone (70% v/v) in an ultrasonic bath for 15 minutes and then centrifuged at 2000 G for 15 minutes. Supernatant was decanted and the extraction procedure was repeated two additional times on the remaining residue. Supernatants were combined, acetone was removed by evaporation (<30° C.), and the extract was reconstituted in water (5 mL).

Proanthocyanidin Separation by Sephadex™ LH-20.

The extract of presscake was applied to a chromatography column (Kontes, 2.5 cm ID×10 cm length) packed with Sephadex LH-20 (GE Healthcare, Uppsala, Sweden) equilibrated with water. Five fractions were obtained by sequential elution with 100 mL of the following solvents: water (fraction 1) contained hydroxy-cinnamic acids and other non-phenolic components; water:ethanol (1:1; fraction 2) contained primarily anthocyanins; ethanol (fraction 3) contained primarily flavonols; ethanol:methanol (1:1; fraction 4) contained flavonol aglycones; and water:acetone (1:4; fraction 5) contained PAC used in formulation of tannin-chitosan composites. Acetone was removed from Fraction 5 by evaporation (<30° C.), the extract was reconstituted with methanol to 5 mL and used to produce tannin (PAC)-chitosan composites.

Matrix-Assisted Laser Desorption/Ionization Time-of-Flight Mass Spectrometry.

Mass spectra of proanthocyanidins were collected on a Bruker Reflex II-MALDI-TOF mass spectrometer (Billerica, Mass.) equipped with delayed extraction and a N2 laser (337 nm). In the positive reflectron mode an accelerating voltage of 25.0 kV and a reflectron voltage of 26.5 kV were used. In the positive linear mode and reflectron mode, an accelerating voltage of 25.0 kV was used. Spectra are the sum of 300 shots. Spectra are calibrated with bradykinin (1060.6 MW) and glucagon (3483.8 MW) as external standards. In accordance with previously published results [Krueger, 2000] trans-3-indoleacrylic acid (t-IAA; 5 mg/100 μl 80% aq. acetone) was used as a matrix. Dowex 50X8-400 cation exchange resin (Supelco), equilibrated in 80% aq. acetone (v/v) was used to deionize the analyte:matrix solution.

Results.

Figure 20:
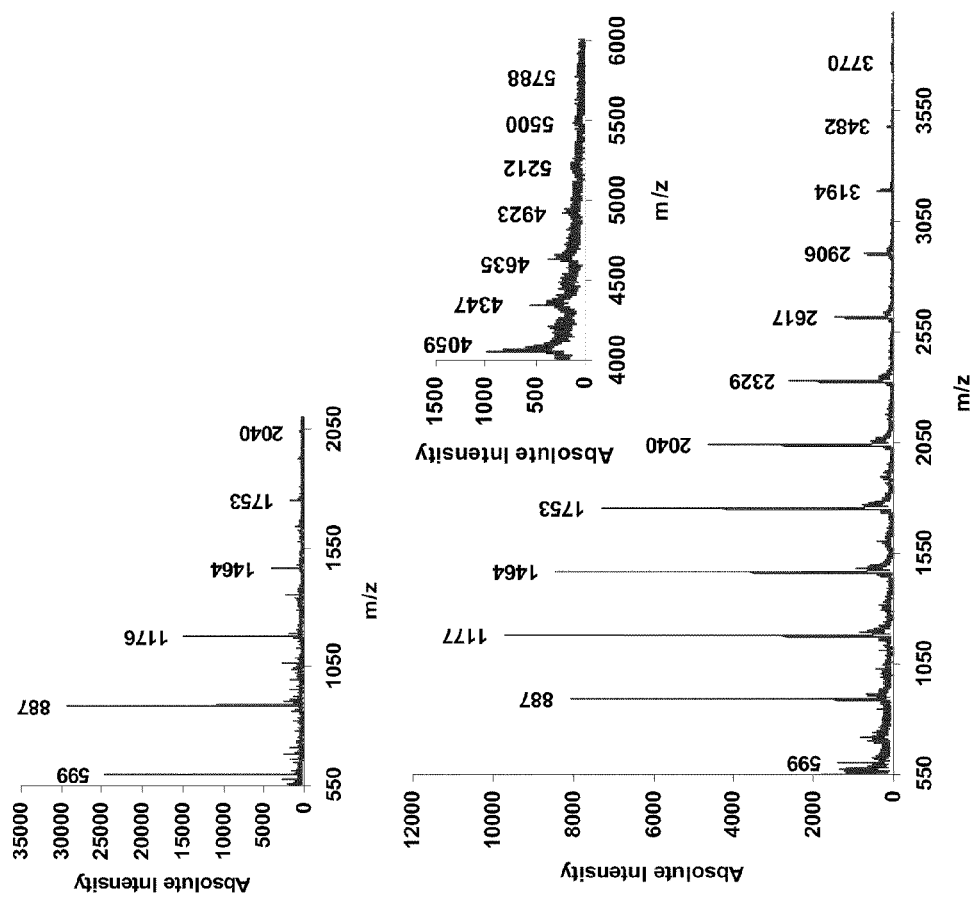
FIG. 20 illustrates positive mode MALDI-TOF MS [M+Na]$^+$ of cranberry proanthocyanidins (PAC) from juice (top spectrum) and presscake (bottom spectrum). The juice PAC are oligomers from 2 to 7 degrees of polymerization (DP), whereas the presscake PAC are oligomers from 2 to 13 DP in the main spectra and from 14 to 20 DP (m/z=5788) in the insert.

MALDI-TOF mass spectral analysis of PAC obtained from cranberry juice indicates that the degree of polymerization ranges from 2-7 (catechin/epicatechin) units. MADLI-TOF mass spectral analysis of PAC obtained from cranberry presscake indicates that the degree of polymerization ranges from 2-20 (catechin/epicatechin) units. FIG. 20 illustrates positive mode MALDI-TOF MS [M+Na]$^+$ of cranberry proanthocyanidins (PAC) from juice (top spectrum) and presscake (bottom spectrum). The juice PAC are oligomers from 2 to 7 degrees of polymerization (DP), whereas the presscake PAC are oligomers from 2 to 13 DP in the main spectra and from 14 to 20 DP (m/z=5788) in the insert.

Therefore, the analysis herein shows that PAC of higher degree of polymerization are not effectively removed from the fruit during the juicing process. A more aggressive extraction procedure (homogenization of presscake and extraction in aqueous organic solvents) is required to obtain PAC of with high degrees of polymerization (i.e., greater than a DP of 7). Furthermore, subjecting the extract to chromatographic separation on Sephadex LH20 resin affords a PAC fraction that was free from monomeric polyphenols (hydroxy cinnamic acids, anthocyanins, and flavonols).

Example 5

Non-Depectinized Cranberry Presscake Tannin (PAC)-Chitosan (Ch) Composites and Hydrogel: Agricultural Pathogenic Fungi (*Colletotrichum acutatum*)

*Colletotrichum acutatum* is a fruit rot pathogen that can affect most plant parts (roots, leaves, blossoms, twigs and fruit). Most significant agricultural losses are due to infection of fruit causing disease in fields (pre-harvest) and of the mature fruit (post-harvest) during storage (Wharton and Dieguez-Uribeonodo 2004).

This Examples shows that cranberry presscake tannin extract-chitosan composites can inhibit germination of *Colletotrichum acutatum* conidia, and can inhibit the growth of *Colletotrichum acutatum* after conidia germination.

Tannin-Chitosan Composite Formulations.

One gram of chitosan was dissolved in 1 L of 1% acetic acid (v/v) to produce a 0.1% (w/v) stock solution. Five grams of cranberry presscake, obtained from the Ocean Spray Inc. Wisconsin Rapids Plant (non-depectinized line process #1), was homogenized in liquid nitrogen. The homogenized presscake was extracted with 20 mL of 70% aqueous acetone (v/v) in an ultrasonic bath for 10 minutes. The extract was centrifuged at 2000 G for 10 minutes, and the supernatant was collected. The residual material was re-extracted two additional times as described above, and the supernatants were combined. Acetone was removed from the presscake under reduced pressure (<30° C.). The extract was then applied to a Sephadex LH-20 column (2.5×10 cm) that had been previously equilibrated in water. The column was sequentially eluted with water (100 mL), 50% aqueous ethanol (v/v; 100 mL) ethanol (100 mL), 50% ethanol:methanol (v/v; 100 mL) and 80% aqueous acetone (v/v; 300 mL). The 80% aq. Acetone fraction was concentrated by roto-vacuum evaporation to a concentration of 29.15 mg Gallic acid equivalents/mL, as determined by the Folin-Ciocalteau assay. MALDI-TOF mass spectrometry characterized the cranberry presscake PAC extract as having 2-20 degree of polymerization (see FIG. 20).

A cranberry presscake tannin extract (Pac)-Chitosan (Ch) composite was prepared by mixing 5 mL of a 0.1% chitosan solution with 3.43 mL of the 29.15 mg GAE/mL presscake extract. The final composite was 20% Pac and 80% Ch by weight. The composite solution was lyophilized and reconstituted in water the same day as the experiments described below.

*Colletotrichum* Conidial Germination and Growth Assay. Culture Plates:
1) Minimal Media (MM); defined media—10 mL in 60 mm plate; Gel-rite.
2) Potato Dextrose Agar (PDA); undefined media—10 mL in 60 mm plate.
3) Blueberry Agar (BB); undefined media—10 mL in 60 mm plate.

*Colletotrichum* is a significant pathogen of blueberry fruit. Accordingly, an undefined blueberry media as a nutrient source was developed. Blueberry fruits were homogenized, autoclaved, and mixed with agar.

After the culture plates cooled, 1 mL of PacCh (20:80, w/w) composite solution was added at 0, 40, 200 and 1000 GAE (gallic acid equivalents). The plates were swirled to allow for equal distribution of the composite solution on the surface. The plates were allowed to dry under a laminar flow hood. A thin hydrogel (film) was generally formed with minimal composite solution being absorbed into the media. After the plates dried (and films formed), 5 μL of a *Colletotrichum acutatum* conidial suspension was pipetted into the center of each plate. Plates were then monitored for conidial germination, fungi growth, and morphology changes.

Minimal Media Results.

After 4 days of incubation, there was no significant difference in culture diameter, however differences in culture morphology were apparent. Higher GAE plates showed less coloring and appeared less mature.

Potato Dextrose Agar Results.

After 4 days of incubation, significant difference in both culture diameter and culture morphology were apparent. Higher GAE plates showed less coloring and appeared less mature. In one experiment, at Day 4, the culture diameter of the 0 GAE plate was 21 mm, while the culture diameter of the 1000 GAE plate was only 16 mm. The culture of the 1000 GAE plate also had less coloring and appeared significantly less mature.

Blueberry Agar Results.

After 4 days of incubation, significant differences in both culture diameter and culture morphology were apparent. The area of the cultures of higher GAE plates were significantly smaller. The area of the culture of the 1000 GAE plate appeared to be less then 10% of the area of the 0 GAE plate, as determined by ocular inspection. Additionally, germination in the 1000 GAE plate sample was delayed until Day 3 of incubation.

Example 6

Tannin-Chitosan Composites Inhibit *E. Coli* Invasion of Caco-2 Cells

Colonization of intestinal epithelial cells by pathogenic bacteria, such as *E. coli*, cause intestinal diseases, including diarrhea and urinary tract infections (UTIs). The three specific pathogenic strains of *E. coli* that are significant causes of diarrhea in infants and travelers to areas with poor sanitation are the enterotoxigenic (ETEC), enteropathogenic (EPEC), and enteroinvasive (EIEC) strains.

Infant mortality from an outbreak of *E. coli* induced diarrhea can have fatality rates as high as 40%. The Centers for Disease Control and Prevention have classified *E. coli* 0157:H7 as one of the more virulent strains, reporting that 20,000 cases of infection may occur annually. *E. coli* 0157:H7 is found in the intestinal tract of cattle. Improper handling and preparation (e.g., undercooking) of ground beef is a leading cause of human infection.

Urinary tract infections are a major medical concern for women and can recur frequently. The vast majority of UTIs are caused by *E. coli* bacteria ascending through the urethra, attaching to the walls of the bladder, multiplying, and causing infection. Antibiotics are prescribed for mild cases, while severe cases often require hospitalization. There is growing concern about uropathogenic bacterial resistance to antibiotics used for UTI treatment. Cranberry proanthocyanidins can act by inhibiting P-fimbriated uropathogenic strains of E. coli from adhering to uroepithelial cells, which is the initial step in development of infection. The new compositions and methods described herein can be used for treating diarrhea and UTIs.

Tannin-Chitosan Composite Formulations.

The tannin-chitosan composite formulations were prepared as described above in Example 5. The composite solutions were either prepared fresh or lyophilized and reconstituted in water the day of the experiments described below.

Tannin-Chitosan Composites Inhibit E. coli Adhesion to Caco-2 Cells.

Caco-2 cells are a human cell line derived from a carcinoma of the colon that exhibits structural and functional differentiation patterns characteristic of mature enterocytes in post-confluent cultures. Caco-2 cells were grown in DMEM+10% FBS+1% dipeptide glutamine+1% Penn/Strep+1% Non-essential Amino Acids and were plated in 24-well cell culture plates. One week after confluency, the cells are differentiated and were subsequently used for the anti-invasion study. After numerous cell counting, the Caco-2 cells averaged 800,000 cells per well on the day of the experiment.

Six replications for each treatment were performed. E. coli strain 5011 was thawed and grown in tryptose broth for 72 hours prior to the start of the experiment, including one passage after 48 hours. The concentration of bacteria was determined by reading a dilution at 420 nm, which was repeatedly $9 \times 10^9$ bacteria per mL. A ratio of 100 bacteria per Caco-2 cell was used for the study.

The bacteria and each of the three treatment compositions: cranberry presscake tannin (5 µg gallic acid equivalent), chitosan (25 µg) and tannin-chitosan (5 µg gallic acid equivalent: 25 µg chitosan), were allowed to react for 10 minutes at room temperature prior to the addition of the experimental cell culture medium (RPMI-1640 plus HEPES with 5% FBS). Caco-2 cells were washed twice with 1×PBS. The bacteria and treatments were further incubated in the medium for 10 minutes prior to being added to the Caco-2 cells. Cells were incubated for 1 hour at 37 degrees C. Cells were washed once in PBS, then incubated at 37 degrees C. for 1 hour with a 100 ug/mL Gentamicin solution (made in RPMI/HEPES plus 5% FBS) to kill any extracellular bacteria. Cells were washed twice with PBS, then incubated for 30 minutes at room temperature with a 1× Triton solution (made in PBS) to lyse the Caco-2 cells. This cellular extract was plated onto Eosin Methylene Blue Agar plates as whole extract, 1:10, and 1:100 dilutions. Plates were inverted and incubated overnight at 37 degrees C. Colony forming units were counted the next day. Colony forming units represent the number of E. coli that invaded the Caco-2 cells.

Results.

Figure 21:
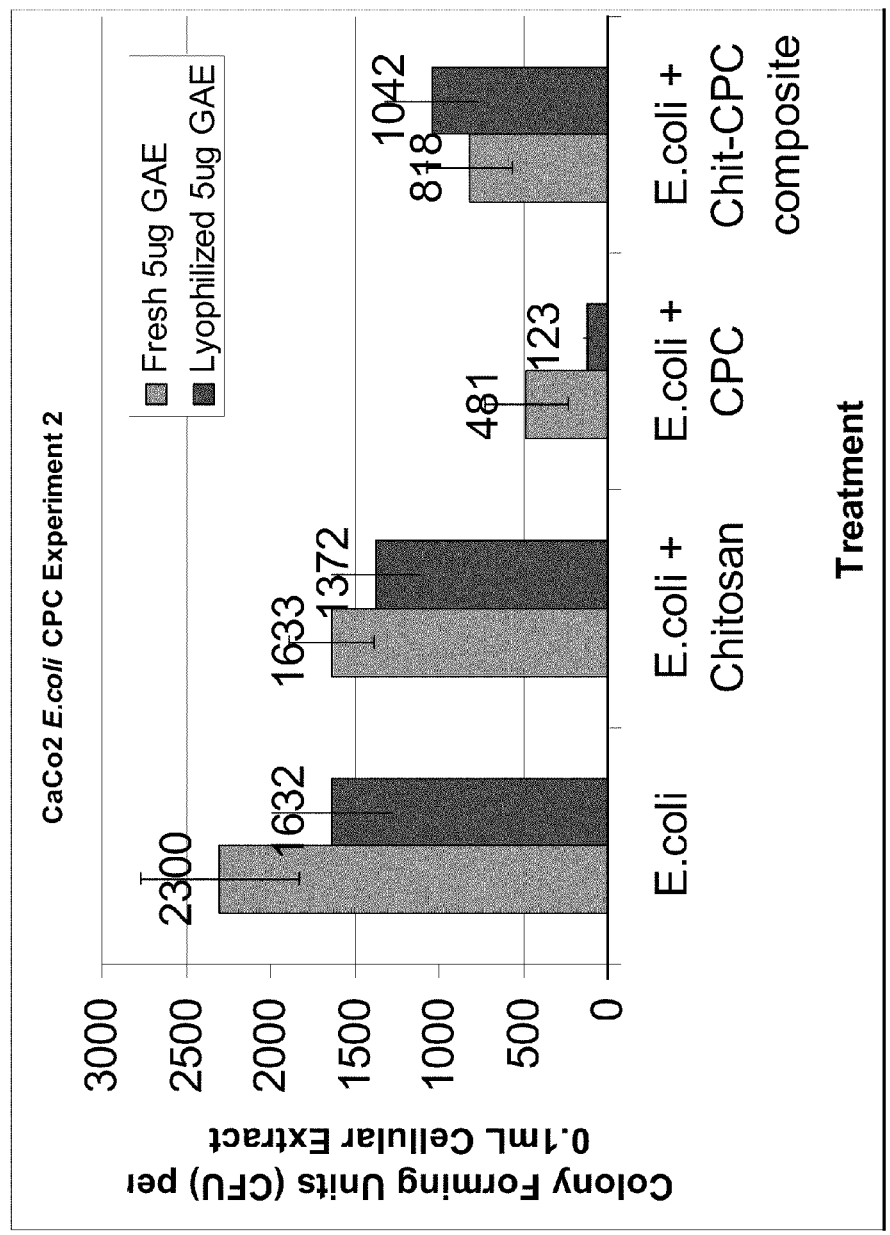
FIG. 21 illustrates the reduction in Colony Forming Units (CFU) of Caco-2 *E. coli* after treatments with chitosan, cranberry presscake (CPC) tannins, and a chitosan-CPC composite, compared to a control experiment.

Test results indicated that cranberry presscake tannin (5 µg gallic acid equivalent), chitosan (25 µg) and tannin-chitosan (5 µg gallic acid equivalent: 25 µg chitosan) composite treatments all inhibited invasion of Caco-2 cells by E. coli strain 5011. Cranberry presscake tannins alone were the most bioactive, followed by the composite material. Chitosan alone was the least effective. The variability between freshly prepared composite material and lyophilized composites was within the variability of replication. FIG. 21 illustrates the results of the experiments.

Example 7

Tannin-Chitosan Composite and Nano-Particle Synthesis

This example describes how the amount of tannin (cranberry presscake PAC) and amount of 3-polyphosphate affect particle size. The following procedures were used.

1.) A 5 mg/mL Chitosan Stock Solution was prepared by dissolving 5 grams of chitosan into 1000 mL with 1% acetic acid solution.

2.) A 1 mg/mL Chitosan Solution was prepared. DI water was used to dilute 20 mL of the 5 mg/mL Chitosan solution into 100 mL.

3.) The Stock Cranberry Presscake was diluted to create a PAC Working Stock. Five grams of cranberry presscake was then processed and chromatographed as described above in Example 5. A cranberry presscake tannin extract (Pac)-Chitosan (Ch) composite was made by mixing 5 mL of a 0.1% chitosan solution with 3.43 mL of the 29.15 mg GAE/mL presscake extract. The final composite was 20% Pac and 80% Ch by weight. The composite solutions were either prepared fresh or lyophilized and reconstituted in water the day of the experiment. 0.5 mL of stock cranberry presscake (29.15 mg Gallic Acid/mL) was diluted into 5.0 mL with DI water to yield a 2.915 mg GA/mL PAC Working Stock.

4.) Composite Solutions were prepared. Five 5 mL of 1 mg/mL Chitosan solution was pipetted into fifteen 10 mL beakers each (solutions 1-15). All solutions were then stirred vigorously. Constant stir rates were maintained; 0.343 mL (1.0 mg) of PAC Working Stock was pipetted into solutions 1-5, 0.257 mL (0.75 mg) into solutions 6-10, and 0.1715 mL (0.5 mg) into solutions 11-15. Stirring was continued for 15 additional minutes.

5.) Nanoparticles were then prepared. Varying volumes of TPP solution (1 mg/mL) were quickly (not dropwise) pipetted into each solution. TPP volumes of 0.25 mL, 0.50 mL, 0.75 mL, 1.00 mL, and 1.25 mL were used for solutions 1-5, 6-10, and 11-15, respectively. An appropriate volume of DI water was added to each solution in order for all the solutions to have a total volume of 7 mL. Stirring was continued for 15 additional minutes.

6.) Nanoparticle size was then measured. The parameters of the particle size instrument were set to 5 runs at 30 seconds each and a Real Refractive Index of 1.420.

7.) The Nanoparticle Samples were then Lyophilized, re-suspend, and measured. The nanoparticle solutions were placed into a freezer until frozen and then placed into a freeze-dryer for 48 hours. The dry samples were re-suspended with DI water to 7.0 mL. Samples were mixed until suspension was complete. The re-suspended nanoparticles were measured at five 30 second runs and a Real Refractive Index of 1.420.

TABLE 7-1

PAC-Ch Composite Nanoparticle Preparation and Composition Data.

| Sample | Sample Composition | | PAC Working | | | |
|---|---|---|---|---|---|---|
| | PAC/Chitosan Ratio | TPP/Chitosan Ratio | Chitosan (1 mg/mL) | Stock (2.915 mg/mL) | TPP (1 mg/mL) | DI Water |
| 1 | 1:5 | 1:20 | 5.0 mL (5.0 mg) | 0.343 mL (1.00 mg) | 0.25 mL (0.25 mg) | 1.407 mL |
| 2 | 1:5 | 1:10 | 5.0 mL (5.0 mg) | 0.343 mL (1.00 mg) | 0.50 mL (0.50 mg) | 1.157 mL |
| 3 | 1:5 | 1:6.67 | 5.0 mL (5.0 mg) | 0.343 mL (1.00 mg) | 0.75 mL (0.75 mg) | 0.907 mL |
| 4 | 1:5 | 1:5 | 5.0 mL (5.0 mg) | 0.343 mL (1.00 mg) | 1.00 mL (1.00 mg) | 0.657 mL |
| 5 | 1:5 | 1:4 | 5.0 mL (5.0 mg) | 0.343 mL (1.00 mg) | 1.25 mL (1.25 mg) | 0.407 mL |
| 6 | 1:6.67 | 1:20 | 5.0 mL (5.0 mg) | 0.257 mL (0.75 mg) | 0.25 mL (0.25 mg) | 1.493 mL |
| 7 | 1:6.67 | 1:10 | 5.0 mL (5.0 mg) | 0.257 mL (0.75 mg) | 0.50 mL (0.50 mg) | 1.243 mL |
| 8 | 1:6.67 | 1:6.67 | 5.0 mL (5.0 mg) | 0.257 mL (0.75 mg) | 0.75 mL (0.75 mg) | 0.993 mL |
| 9 | 1:6.67 | 1:5 | 5.0 mL (5.0 mg) | 0.257 mL (0.75 mg) | 1.00 mL (1.00 mg) | 0.743 mL |
| 10 | 1:6.67 | 1:4 | 5.0 mL (5.0 mg) | 0.257 mL (0.75 mg) | 1.25 mL (1.25 mg) | 0.493 mL |
| 11 | 1:10 | 1:20 | 5.0 mL (5.0 mg) | 0.1715 mL (0.50 mg) | 0.25 mL (0.25 mg) | 1.579 mL |
| 12 | 1:10 | 1:10 | 5.0 mL (5.0 mg) | 0.1715 mL (0.50 mg) | 0.50 mL (0.50 mg) | 1.329 mL |
| 13 | 1:10 | 1:6.67 | 5.0 mL (5.0 mg) | 0.1715 mL (0.50 mg) | 0.75 mL (0.75 mg) | 1.079 mL |
| 14 | 1:10 | 1:5 | 5.0 mL (5.0 mg) | 0.1715 mL (0.50 mg) | 1.00 mL (1.00 mg) | 0.829 mL |
| 15 | 1:10 | 1:4 | 5.0 mL (5.0 mg) | 0.1715 mL (0.50 mg) | 1.25 mL (1.25 mg) | 0.579 mL |

Results.

TABLE 7-2

Figure 22:
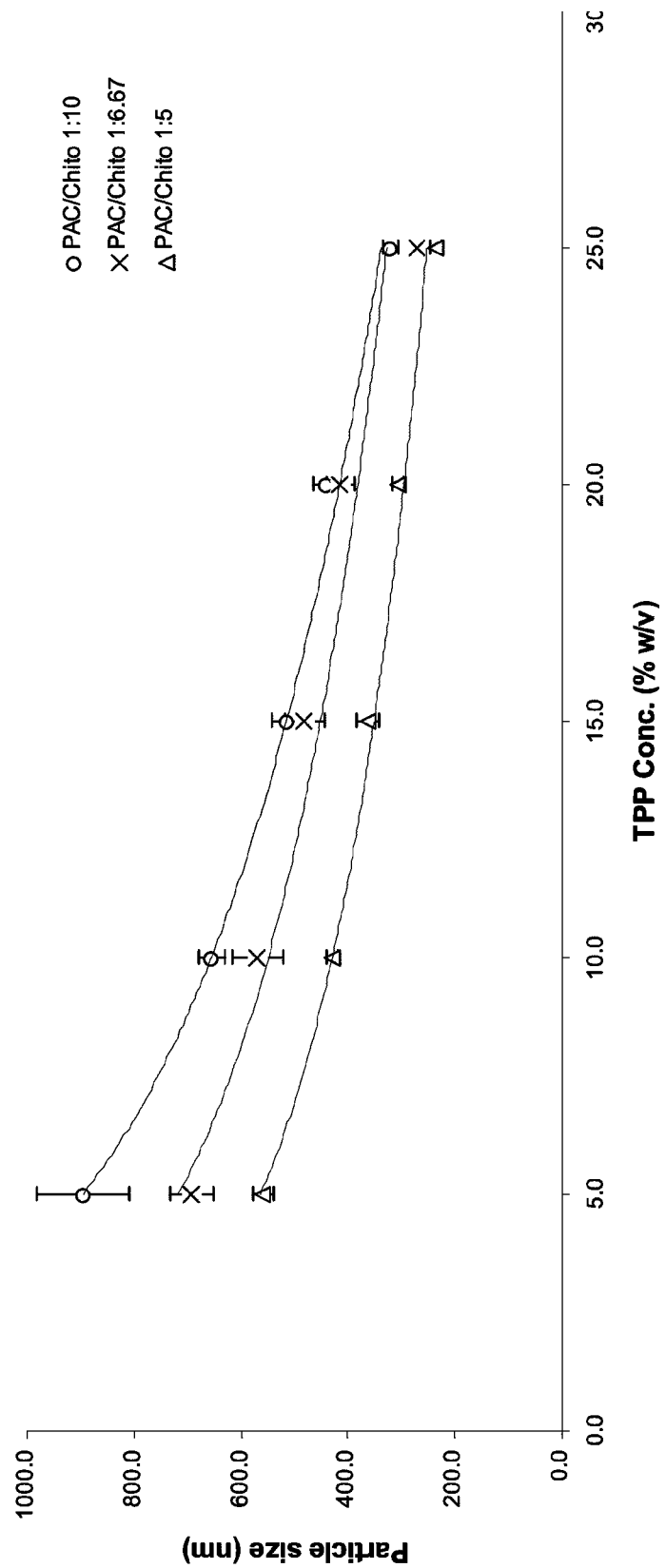
FIG. 22 illustrates the change in nanoparticle particle size as a function of tripolyphosphate (TPP) concentration, for certain ratios of specific tannin-chitosan composites (see Table 7-2).

Data used to prepare FIG. 22.
BATCH 1 Jun. 3, 2009

| Sample ID | Size (nm) | SE (±) |
|---|---|---|
| PAC/Chito 1:10; TPP 1:20 | 895.0 | 85.8 |
| PAC/Chito 1:10; TPP 1:10 | 653.4 | 24.7 |
| PAC/Chito 1:10; TPP 1:6.67 | 512.7 | 28.7 |
| PAC/Chito 1:10; TPP 1:5 | 439.6 | 25.4 |
| PAC/Chito 1:10; TPP 1:4 | 321.1 | 13.7 |
| PAC/Chito 1:6.67; TPP 1:20 | 692.6 | 39.8 |
| PAC/Chito 1:6.67; TPP 1:10 | 568.9 | 48.6 |
| PAC/Chito 1:6.67; TPP 1:6.67 | 481.2 | 36.3 |
| PAC/Chito 1:6.67; TPP 1:5 | 414.3 | 27.6 |
| PAC/Chito 1:6.67; TPP 1:4 | 272.0 | 7.5 |
| PAC/Chito 1:5; TPP 1:20 | 559.1 | 20.1 |
| PAC/Chito 1:5; TPP 1:10 | 429.5 | 12.0 |
| PAC/Chito 1:5; TPP 1:6.67 | 362.1 | 21.3 |
| PAC/Chito 1:5; TPP 1:5 | 306.8 | 10.4 |
| PAC/Chito 1:5; TPP 1:4 | 235.3 | 10.0 |

TABLE 7-3

Figure 23:
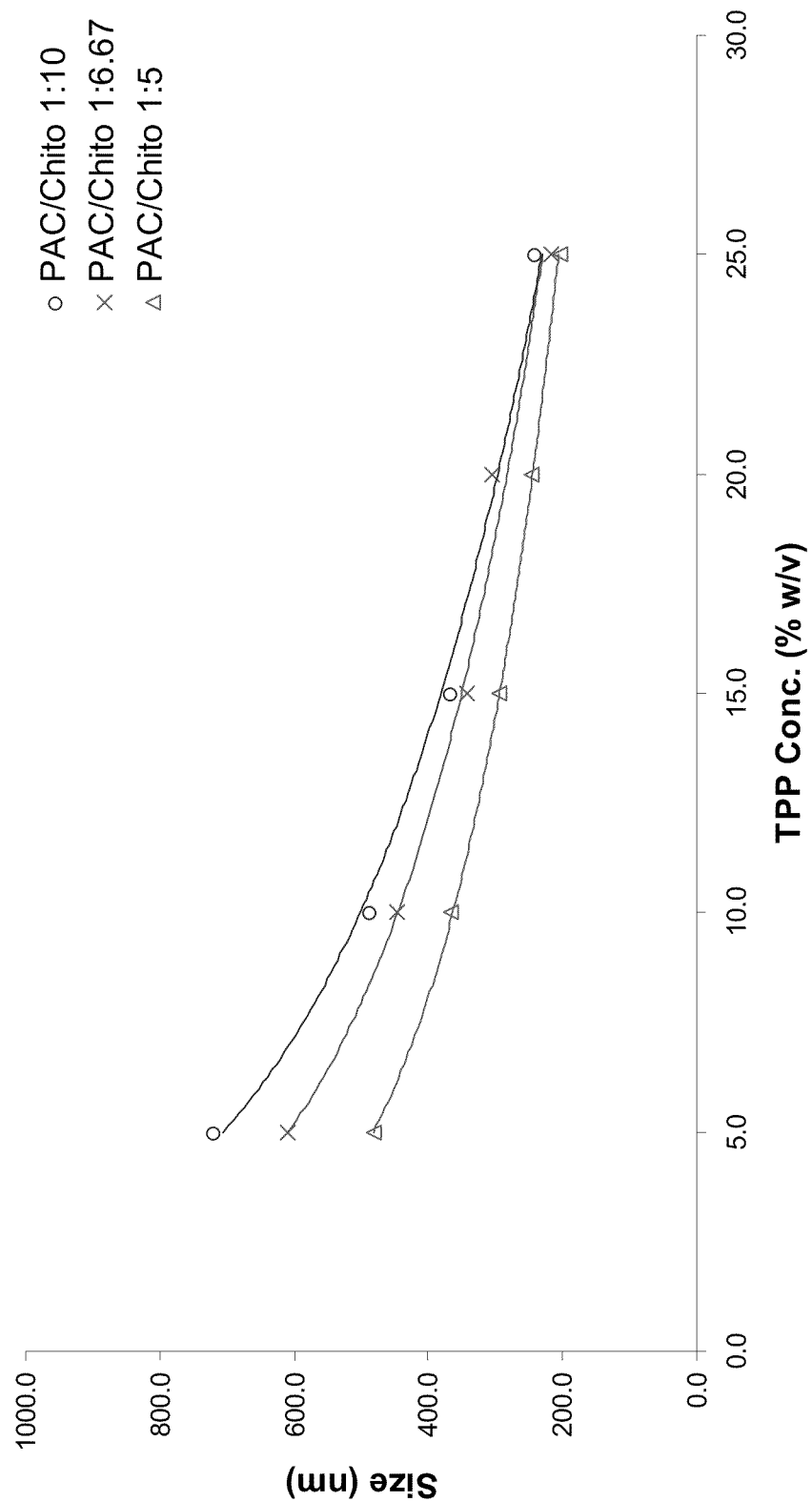
FIG. 23 illustrates the change in nanoparticle particle size as a function of TPP concentration, for certain ratios of specific tannin-chitosan composites (see Table 7-3).

Data used to prepare FIG. 23.
BATCH 2 Jun. 4, 2009

| Sample ID | Size (nm) | SE (±) |
|---|---|---|
| PAC/Chito 1:10; TPP 1:20 | 718.1 | 64.1 |
| PAC/Chito 1:10; TPP 1:10 | 486.5 | 13.1 |
| PAC/Chito 1:10; TPP 1:6.67 | 367.3 | 7.5 |
| PAC/Chito 1:10; TPP 1:5 | 305.5 | 15.8 |
| PAC/Chito 1:10; TPP 1:4 | 239.4 | 4.4 |
| PAC/Chito 1:6.67; TPP 1:20 | 608.7 | 21.1 |
| PAC/Chito 1:6.67; TPP 1:10 | 446.1 | 9.1 |
| PAC/Chito 1:6.67; TPP 1:6.67 | 341.6 | 11.1 |
| PAC/Chito 1:6.67; TPP 1:5 | 303.7 | 9.3 |
| PAC/Chito 1:6.67; TPP 1:4 | 217.5 | 4 |
| PAC/Chito 1:5; TPP 1:20 | 481.1 | 17 |
| PAC/Chito 1:5; TPP 1:10 | 365.6 | 13.3 |
| PAC/Chito 1:5; TPP 1:6.67 | 293.2 | 6.9 |
| PAC/Chito 1:5; TPP 1:5 | 246.5 | 2.2 |
| PAC/Chito 1:5; TPP 1:4 | 203.8 | 4.4 |

TABLE 7-4

Figure 24:
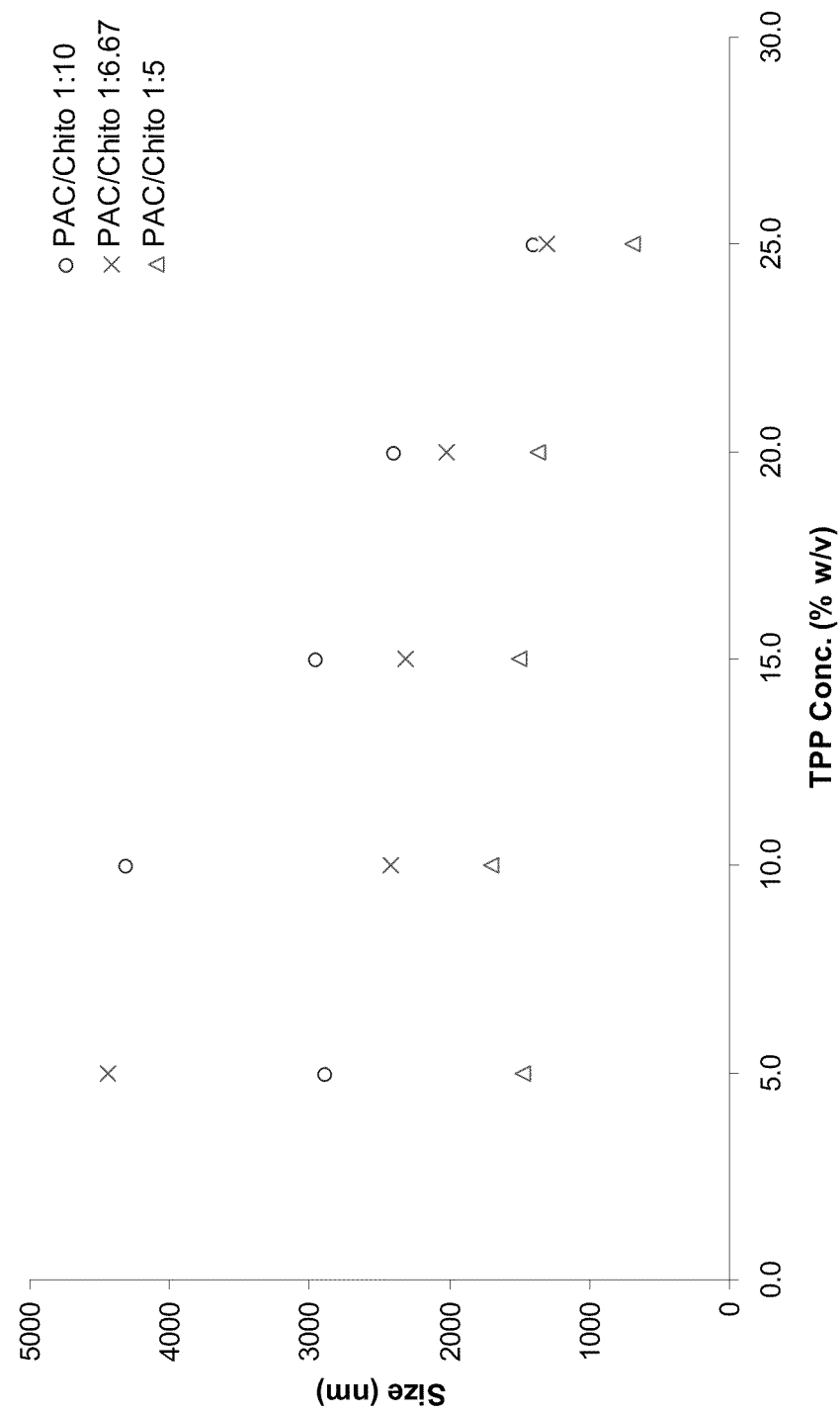
FIG. 24 illustrates the change in nanoparticle particle size as a function of TPP concentration, for certain ratios of specific tannin-chitosan composites (see Table 7-4).

Data used to prepare FIG. 24.
BATCH 2 LYOPHILIZED AND RE-SUSPENDED Jun. 17, 2009

| Sample ID | Size (nm) | SE (±) |
|---|---|---|
| PAC/Chito 1:10; TPP 1:20 | 2885.3 | 146.0 |
| PAC/Chito 1:10; TPP 1:10 | 4309.8 | 720.4 |
| PAC/Chito 1:10; TPP 1:6.67 | 2955.4 | 369.0 |
| PAC/Chito 1:10; TPP 1:5 | 2388.2 | 332.5 |
| PAC/Chito 1:10; TPP 1:4 | 1396.7 | 193.4 |
| PAC/Chito 1:6.67; TPP 1:20 | 4446.4 | 267.9 |
| PAC/Chito 1:6.67; TPP 1:10 | 2414.0 | 468.0 |
| PAC/Chito 1:6.67; TPP 1:6.67 | 2314.5 | 467.3 |
| PAC/Chito 1:6.67; TPP 1:5 | 2016.9 | 64.7 |
| PAC/Chito 1:6.67; TPP 1:4 | 1300.5 | 181.6 |
| PAC/Chito 1:5; TPP 1:20 | 1470.0 | 26.3 |
| PAC/Chito 1:5; TPP 1:10 | 1701.9 | 318.0 |

TABLE 7-4-continued

Data used to prepare FIG. 24.
BATCH 2 LYOPHILIZED AND RE-SUSPENDED Jun. 17, 2009

| Sample ID | Size (nm) | SE (±) |
|---|---|---|
| PAC/Chito 1:5; TPP 1:6.67 | 1505.3 | 82.9 |
| PAC/Chito 1:5; TPP 1:5 | 1366.7 | 342.4 |
| PAC/Chito 1:5; TPP 1:4 | 689.7 | 46.2 |

Summary.

TPP and PAC concentrations both affect particle size. TPP concentration and particle size share an inverse relationship. At all three proanthocyanidin concentrations tested, an increase in TPP concentration reduced particle size. Increasing the PAC concentration also reduces particle size. The graphic results indicate a logarithmic trend of increasing TPP concentration versus particle size. As PAC concentrations continue to increase beyond 1:5, there is a point at which increased PAC concentrations ceases to cause a decrease in particle size. Likewise, there is a maximum limit of how high the TPP concentration can be with continued decreases in particle size. The re-suspended particle data shows that the nanoparticles become unstable and may fall into solution after a period of seven days of refrigerated storage (~37° C.).

Example 8

Grape Seed Tannins-Chitosan Composite and Nano-Particle Synthesis

Determinations were made regarding how the amount of tannins in grape seed extract (GSE) and the amount of 3-polyphosphate affect particle size. The GSE-chitosan nanoparticles have similar physical and chemical characteristics to cranberry tannin-chitosan composites regarding particle size and the effect of the tannin to chitosan loading. The following procedure was used for the Grape Seed Extract (GSE)/Chitosan Nanoparticle preparation.

1.) A 5 mg/mL Chitosan Stock Solution was prepared. Five 5 grams of chitosan was dissolved into 1000 mL DI water with 1% acetic acid solution. The solution was vacuum filter with a Whatman #41 filter.

2.) A 1 mg/mL Chitosan Solution was prepared. DI water was used to dilute 20 mL of 5 mg/mL Chitosan solution into 100 mL.

3-1.) Stock Grape Seed Extract was diluted to create a GSE Working Stock. 0.2835 mL of stock Grape Seed Extract (51.41 mg Gallic Acid/mL) was diluted into 5.0 mL with DI water to yield a 2.915 mg GA/mL GSE Working Stock.

4.) Composite solutions were then prepared. Five mL of 1 mg/mL Chitosan solution was pipetted into fifteen 10 mL beakers each (solutions 1-15). The solutions were vigorously stirred. Constant stir rates were maintained and 0.343 mL (1.0 mg) of GSE Working Stock was pipetted into solutions 1-5, 0.257 mL (0.75 mg) was pipetted into solutions 6-10, and 0.1715 mL (0.5 mg) was pipetted into solutions 11-15. Stirring was continued for 15 minutes.

5.) Nanoparticles were then prepared. Varying volumes of TPP solution (1 mg/mL) were quickly pipetted into each solution. TPP volumes of 0.25 mL, 0.50 mL, 0.75 mL, 1.00 mL, and 1.25 mL were used for solutions 1-5, 6-10, and 11-15. An appropriate volume of DI water was added to each solution in order for all the solutions to have a total volume of 7 mL. The solutions were stirred for 15 additional minutes.

6.) Nanoparticle size was measured. The parameters of the particle size instrument were set to 3 runs at 30 seconds each and a Real Refractive Index of 1.420.

7.) The process was repeated using cranberry proanthocyanidins.

3-2.) Stock cranberry PAC was diluted to create a PAC Working Stock. 0.2445 mL of stock cranberry PAC's from Batch 3 (59.61 mg Gallic Acid/mL) was diluted into 5.0 mL with DI water to yield a 2.915 mg GA/mL PAC Working Stock.

Figure 25:
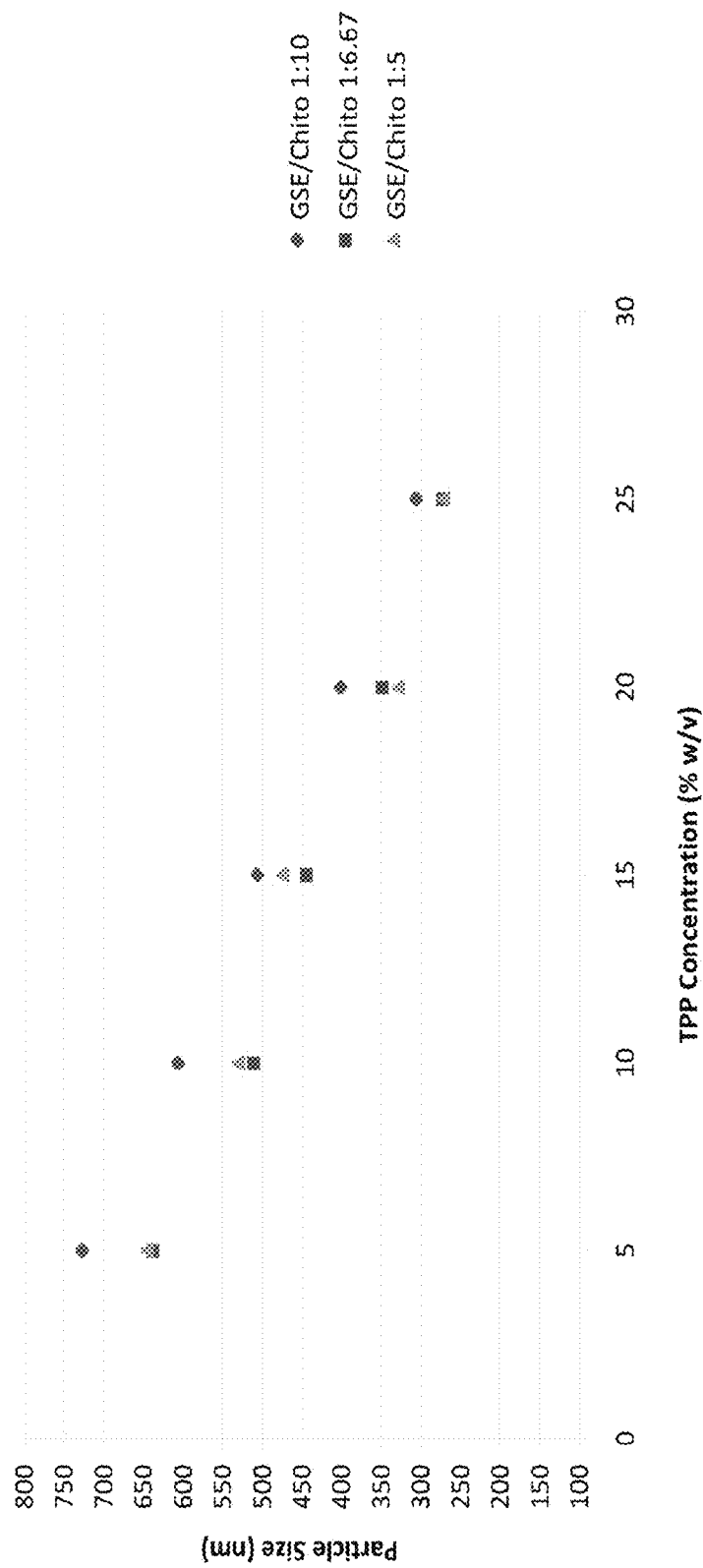
FIG. 25 illustrates the grape seed extract (GSE)/chitosan nanoparticle size distribution, as determined by the procedures of Example 8.
Figure 26:
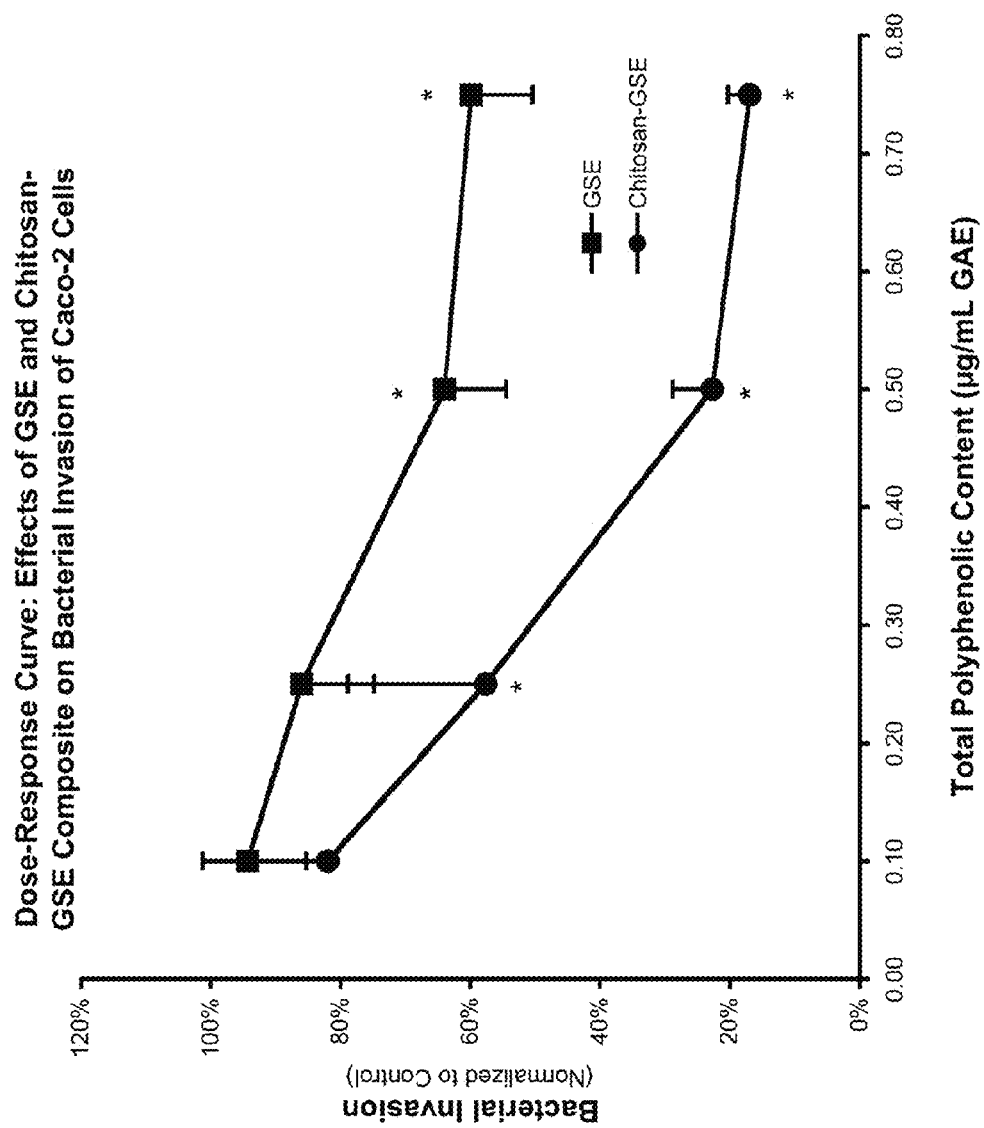
FIG. 26 illustrates a dose-response curve, as determined in Example 8, for the effects of grape seed extract (GSE) and chitosan-GSE composites on bacterial invasion of Caco-2 cells.

Preparation data and results are provided in Tables 8-1 and 8-2 and the results are illustrated in FIGS. 25 and 26. FIG. 25 illustrates the grape seed extract (GSE)/chitosan nanoparticle size distribution, and FIG. 26 illustrates a dose-response, showing the effects of GSE and chitosan-GSE composites on bacterial invasion of Caco-2 cells. The effects (mean±SD) of Grape Seed Extract (GSE) Tannins, and Chitosan-GSE composite nanoparticles on the invasion of Caco-2 cells by *E. coli* strain 5011 are clearly demonstrated. An asterisk indicates an effect that is statistically significant compared to the corresponding control. This data indicates that the Chitosan-GSE composite nanoparticles are significantly more active than GSE alone.

TABLE 8-1

Procedure Chart.

| Sample | Sample Comp. GSE&PAC/ Chitosan Ratio | TPP/ Chitosan Ratio | Chitosan (1 mg/mL) | GSE&PAC Working Stock (2.915 mg/mL) | TPP (1 mg/mL) | DI Water |
|---|---|---|---|---|---|---|
| 1 | 1 to 5 | 1 to 20 | 5.0 mL (5.0 mg) | 0.343 mL (1.00 mg) | 0.25 mL (0.25 mg) | 1.4069 mL |
| 2 | 1 to 5 | 1 to 10 | 5.0 mL (5.0 mg) | 0.343 mL (1.00 mg) | 0.50 mL (0.50 mg) | 1.1570 mL |
| 3 | 1 to 5 | 1 to 6.67 | 5.0 mL (5.0 mg) | 0.343 mL (1.00 mg) | 0.75 mL (0.75 mg) | 0.9069 mL |
| 4 | 1 to 5 | 1 to 5 | 5.0 mL (5.0 mg) | 0.343 mL (1.00 mg) | 1.00 mL (1.00 mg) | 0.6569 mL |
| 5 | 1 to 5 | 1 to 4 | 5.0 mL (5.0 mg) | 0.343 mL (1.00 mg) | 1.25 mL (1.25 mg) | 0.4069 mL |
| 6 | 1 to 6.67 | 1 to 20 | 5.0 mL (5.0 mg) | 0.257 mL (0.75 mg) | 0.25 mL (0.25 mg) | 1.4927 mL |
| 7 | 1 to 6.67 | 1 to 10 | 5.0 mL (5.0 mg) | 0.257 mL (0.75 mg) | 0.50 mL (0.50 mg) | 1.2427 mL |
| 8 | 1 to 6.67 | 1 to 6.67 | 5.0 mL (5.0 mg) | 0.257 mL (0.75 mg) | 0.75 mL (0.75 mg) | 0.9927 mL |

TABLE 8-1-continued

Procedure Chart.

| Sample | Sample Comp. GSE&PAC/ Chitosan Ratio | TPP/ Chitosan Ratio | Chitosan (1 mg/mL) | GSE&PAC Working Stock (2.915 mg/mL) | TPP (1 mg/mL) | DI Water |
|---|---|---|---|---|---|---|
| 9 | 1 to 6.67 | 1 to 5 | 5.0 mL (5.0 mg) | 0.257 mL (0.75 mg) | 1.00 mL (1.00 mg) | 0.7427 mL |
| 10 | 1 to 6.67 | 1 to 4 | 5.0 mL (5.0 mg) | 0.257 mL (0.75 mg) | 1.25 mL (1.25 mg) | 0.4927 mL |
| 11 | 1 to 10 | 1 to 20 | 5.0 mL (5.0 mg) | 0.1715 mL (0.50 mg) | 0.25 mL (0.25 mg) | 1.5785 mL |
| 12 | 1 to 10 | 1 to 10 | 5.0 mL (5.0 mg) | 0.1715 mL (0.50 mg) | 0.50 mL (0.50 mg) | 1.3285 mL |
| 13 | 1 to 10 | 1 to 6.67 | 5.0 mL (5.0 mg) | 0.1715 mL (0.50 mg) | 0.75 mL (0.75 mg) | 1.0785 mL |
| 14 | 1 to 10 | 1 to 5 | 5.0 mL (5.0 mg) | 0.1715 mL (0.50 mg) | 1.00 mL (1.00 mg) | 0.8285 mL |
| 15 | 1 to 10 | 1 to 4 | 5.0 mL (5.0 mg) | 0.1715 mL (0.50 mg) | 1.25 mL (1.25 mg) | 0.5785 mL |

TABLE 8-2

Summary of Average Particle Size.

| Sample ID | Run 1 | Run 2 | Run 3 | Average | SE (±) |
|---|---|---|---|---|---|
| GSE/Chito 1:5; TPP/Chito 1:20 | 749.9 | 701.6 | 729.1 | 726.9 | 14 |
| GSE/Chito 1:5; TPP/Chito 1:10 | 603.4 | 613.8 | 600.9 | 606 | 3.9 |
| GSE/Chito 1:5; TPP/Chito 1:6.67 | 492.3 | 511.8 | 514.5 | 506.2 | 7 |
| GSE/Chito 1:5; TPP/Chito 1:5 | 402.3 | 392.3 | 408.2 | 401 | 4.7 |
| GSE/Chito 1:5; TPP/Chito 1:4 | 302.5 | 314.1 | 301.8 | 306.1 | 4 |
| GSE/Chito 1:6.67; TPP/Chito 1:20 | 653.2 | 628.6 | 631.7 | 637.8 | 7.8 |
| GSE/Chito 1:6.67; TPP/Chito 1:10 | 512.5 | 525.1 | 494.2 | 510.6 | 9 |
| GSE/Chito 1:6.67; TPP/Chito 1:6.67 | 447.3 | 440.3 | 443.8 | 443.8 | 2 |
| GSE/Chito 1:6.67; TPP/Chito 1:5 | 346.9 | 356.4 | 341.5 | 348.3 | 4.4 |
| GSE/Chito 1:6.67; TPP/Chito 1:4 | 274.7 | 275.6 | 266.8 | 272.4 | 2.8 |
| GSE/Chito 1:10; TPP/Chito 1:20 | 679.1 | 601.4 | 654.6 | 645 | 22.9 |
| GSE/Chito 1:10; TPP/Chito 1:10 | 498.7 | 539.1 | 553.6 | 530.5 | 16.4 |
| GSE/Chito 1:10; TPP/Chito 1:6.67 | 502.9 | 471.4 | 447.7 | 474 | 16 |
| GSE/Chito 1:10; TPP/Chito 1:5 | 322.9 | 343.2 | 319.5 | 328.5 | 7.4 |
| GSE/Chito 1:10; TPP/Chito 1:4 | 262.9 | 279.9 | 270.6 | 271.1 | 4.9 |

Example 9

Tannin-Chitosan Composites as Therapeutic Biomaterials

This example demonstrates the application of tannin-chitosan composite nanoparticles for use as therapeutic biomaterials to control pathogenic microbial colonization of human epithelial cells. The tannin-chitosan composite nanoparticles can therefore be used for the treatment and prevention of human disease states such as, diarrhea, resultant of enterotoxigenic *Escherichia coli* (ETEC) and other pathogenic microbe colonization of the intestinal epithelial cells, and urinary tract infections (UTI) resulting from adhesion of p-fimbriated uropathogenic bacteria to uroepithelial cells.

Results show that tannin-chitosan composite nanoparticles significantly reduced invasion of intestinal epithelial cells by uropathogenic *E. coli*. Furthermore, scanning electron microscopy allowed for the identification of a putative mechanism by which invasion is inhibited. Tannin-chitosan composite nanoparticles are believed to coat and cross-link *E. coli* flagella, thereby inhibiting invasion.

Results.

Invasion of Intestinal Epithelial Cells.

Figure 27:
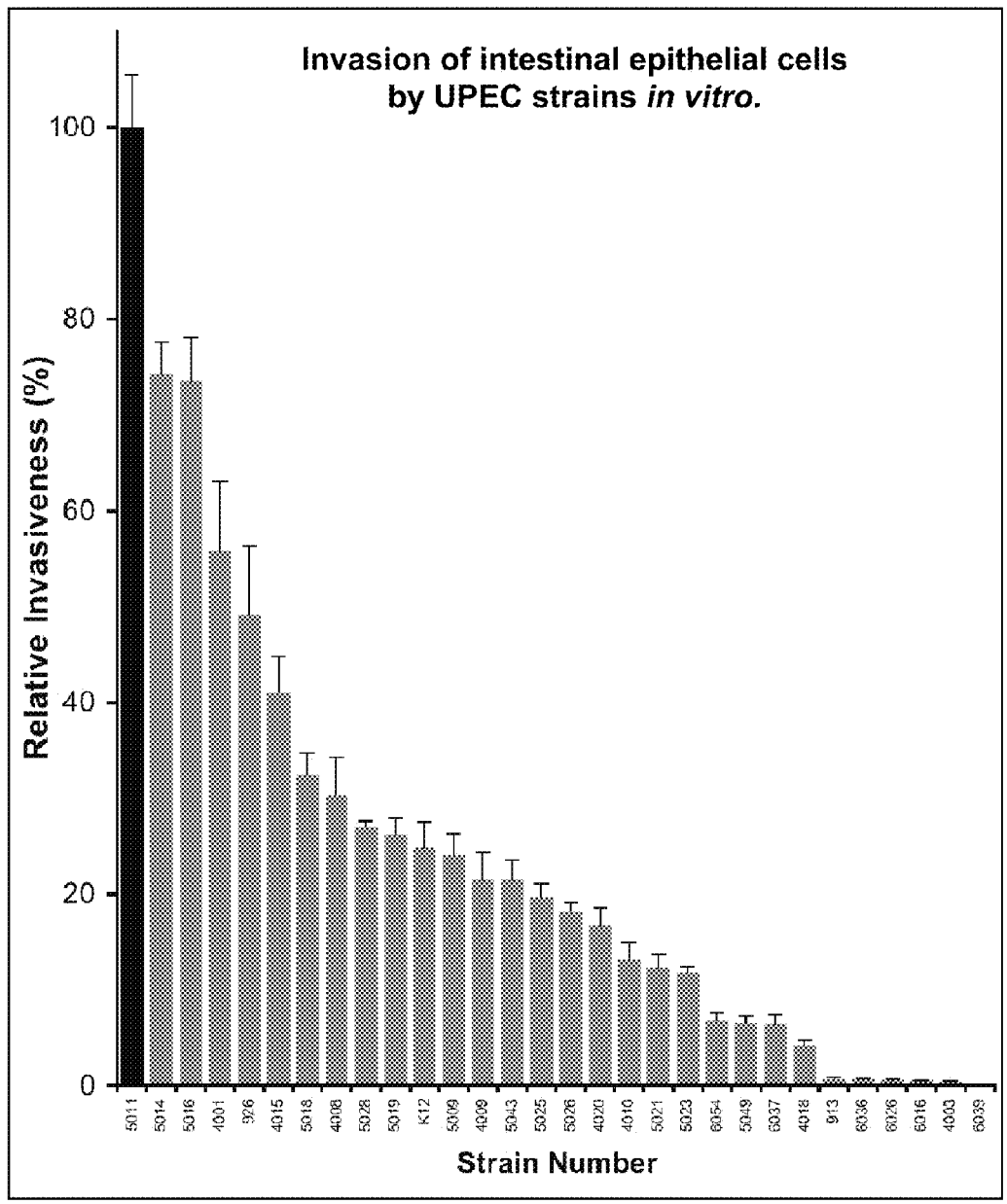
FIG. 27 illustrates relative invasion of gastrointestinal (GI) epithelial cells (Caco-2) by uropathogenic *Escherichia coli* (UPEC), according to the methods of Example 8. Thirty strains of UPEC isolated from women with chronic UTI. The most invasive strain was UPEC 5011 (black bar), which was selected for evaluation in invasion experiments.

Using an assay that developed to study the invasion of gastrointestinal (GI) epithelial cells (Caco-2) by uropathogenic *Escherichia coli* (UPEC), the relative invasiveness of 30 strains of UPEC isolated from women with chronic UTI was examined (FIG. 27). The relative ability of the UPEC strains to invade GI epithelial cells correlated with their ability to invade uroepithelial cells (prostate cells) in culture (data not shown). Of the strains, UPEC 5011 was found to be most invasive (FIG. 27). For this reason UPEC 5011 was used in all experiments.

Cranberry Tannin-Chitosan Composite Nano-Particles Inhibit Invasion of Intestinal Epithelial Cells.

We have developed LC and MALDI-TOF mass spectrometric techniques to first separate tannins from other polyphenolic compounds and subsequently characterize the structural heterogeneity and oligomeric distribution of tannins. In these experiments, tannins were extracted from cranberry press cake and 1) used alone or 2) combined with chitosan to form nano-particles composite materials. The tannins alone, chitosan nanoparticles alone and tannin-chitosan composite nanoparticles were then mixed with UPEC 5011 before incubation with Caco-2 cells.

Figure 28:
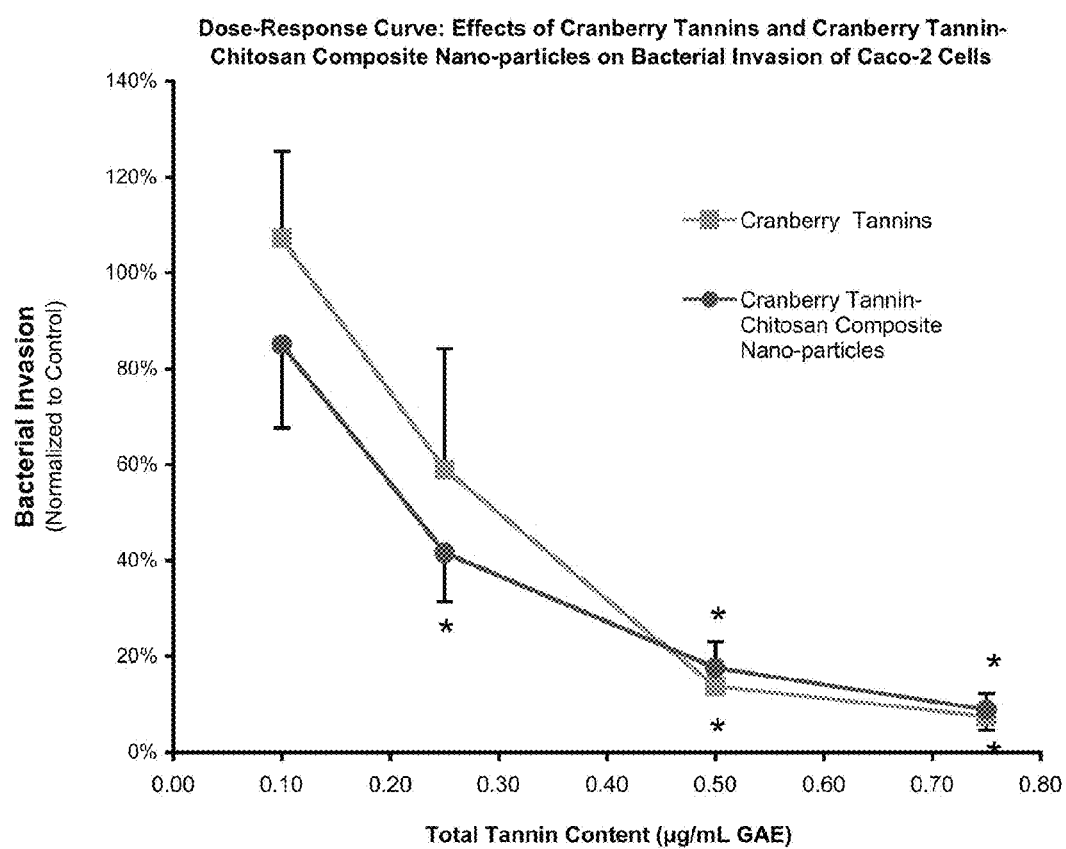
FIG. 28 illustrates the effects (mean±SD) of cranberry tannins, and cranberry tannin-chitosan composite nanoparticles on the invasion of Caco-2 cells by *E. coli* strain 5011. An asterisk indicates an effect that is statistically significant compared to the corresponding control.

Results of a dose-response experiment indicate the tannin-composite material significantly reduced invasion of epithelial cells at a lower dose than the tannin perpetration alone. The cranberry tannin preparation alone significantly inhibited the ability of the pathogen to invade the intestinal epithelial cells by ~82% at a total polyphenolic concentration (0.5 μg of gallic acid equivalence (GAE)/mL and by ~96% at 0.75 μg GAE/mL (FIG. 28). The cranberry tannin-composite nanoparticles significantly inhibited the ability of the pathogen to invade the intestinal epithelial cells by ~40% at a total polyphenolic concentration of 0.2 μg GAE/mL, by ~80% at 0.5 μg GAE/mL and by ~96% at 0.75 μg GAE/mL (FIG. 28).

Figure 29:
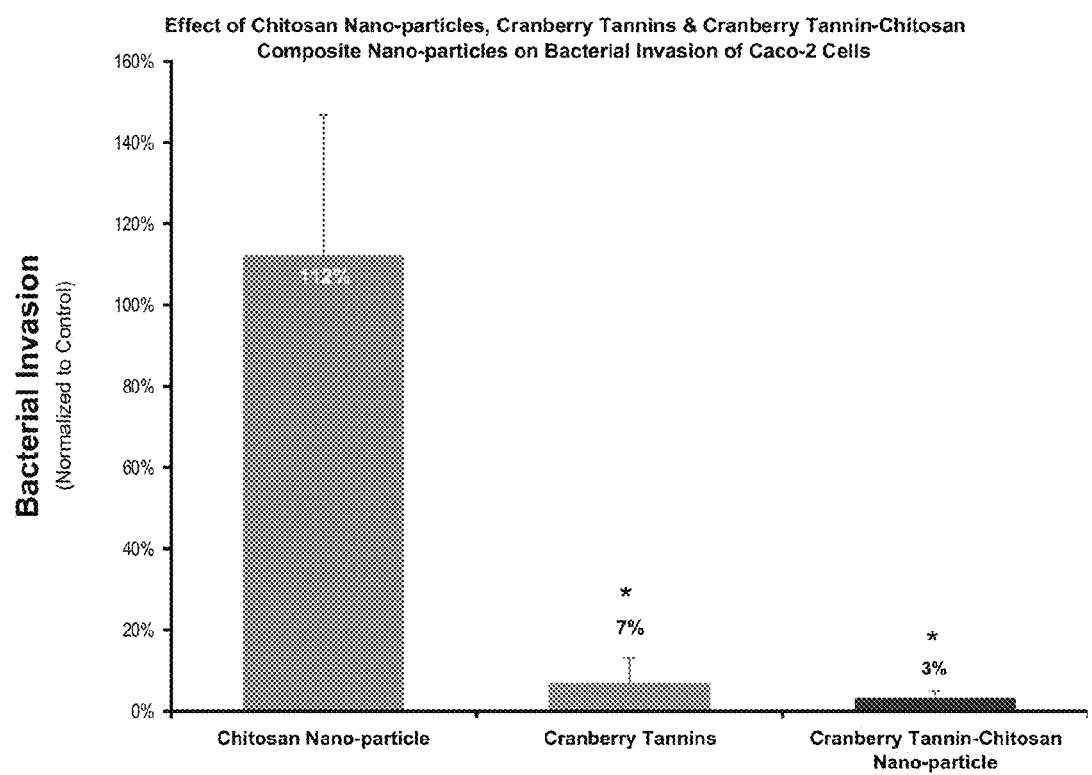
FIG. 29 illustrates the effects (mean±SD) of chitosan nanoparticles, cranberry tannins, and cranberry tannin-chitosan composite nanoparticles on the invasion of Caco-2 cells by *E. coli* strain 5011. An asterisk indicates an effect that is statistically significant compared to the corresponding control. Dose was 0.75 μg gallic acid equivalent (GAE).

The results illustrated in FIG. 29 shows the effects (mean±SD) of chitosan nanoparticles, cranberry tannins, and cranberry tannin-chitosan composite nanoparticles on the invasion of Caco-2 cells by *E. coli* strain 5011. An asterisk indicates an effect that is statistically significant compared to the corresponding control. Dose is 0.75 ug gallic acid equivalent. The results indicate that chitosan nanoparticles alone were not significantly different from controls in preventing UPEC 5011 invasion of intestinal epithelial cells.

Additional comparisons of tannin preparations with varying polymer length indicated that a higher degree of inhibition of invasiveness was achieved by tannins with greater degree of polymerization (DP). Cranberry tannin are believed to inhibit invasion by binding to the pathogen and disrupting the surface adhesion molecules required for invasion. Thus a tannin with greater DP is likely to have a greater affinity for the pathogen. The effects of this interaction was examined using scanning electron microscopy (SEM).

Effect of Cranberry Tannin-Chitosan Composite Nanoparticles on the Physical Structure UPEC Flagella.

Figure 30:
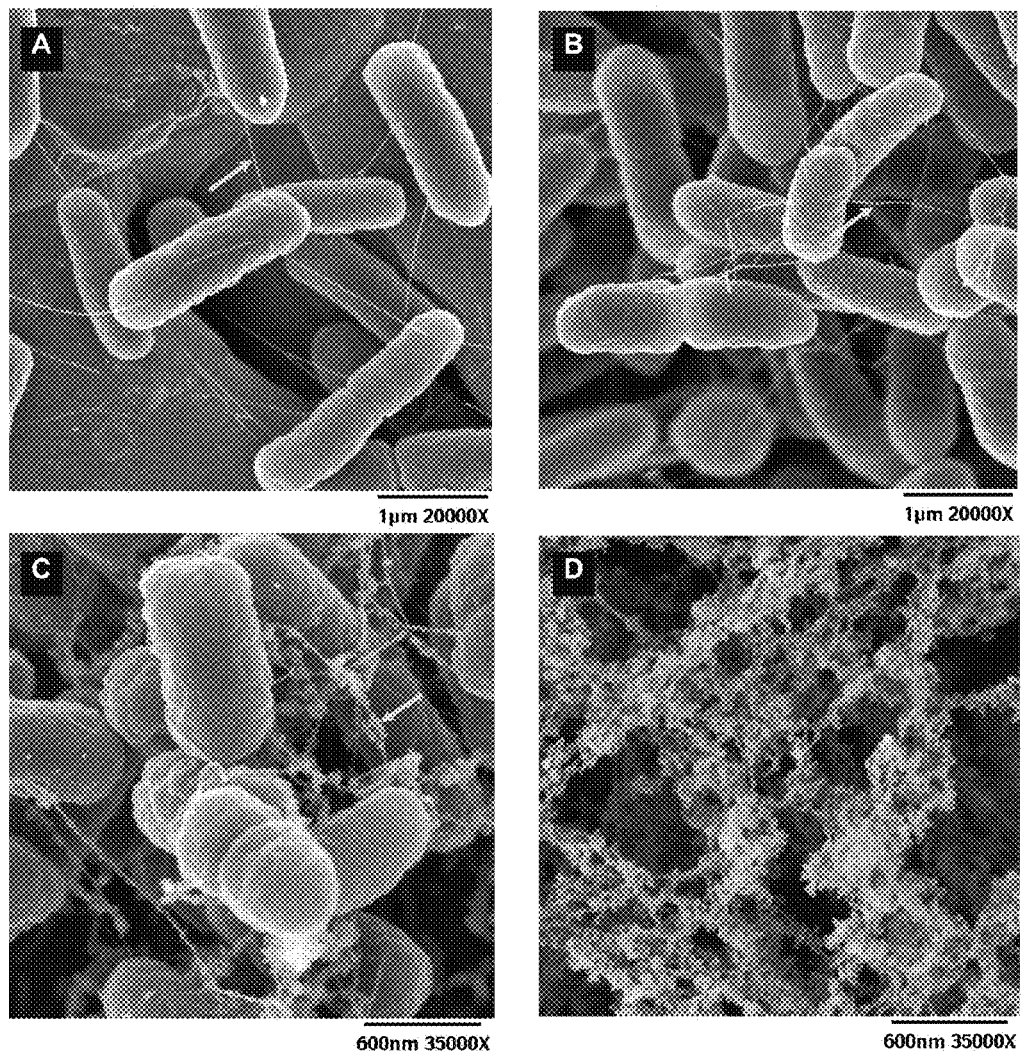
FIG. 30 illustrates Scanning Electron Microscopy (SEM) exploring the interactions of cranberry proanthocyanidin-chitosan composite nanoparticles with UPEC 5011 and its effect on cell invasion. A) UPEC 5011 alone (arrow indicates flagella); B) UPEC 5011+chitosan nanoparticle (arrow indicates no change to flagella); C) UPEC 5011+tannin-chitosan composite nanoparticle (arrow indicates coating and crosslinking of UPEC flagella); and D) tannin-chitosan composite nanoparticles alone (for comparison to material coating flagella).

FIG. 30 shows scanning electron micrographs exploring the effect of chitosan nanoparticles and tannin-chitosan composite nanoparticles on UPEC 5011 flagella structure and subsequent impact on invasion of intestinal epithelial cells in vitro. The arrow in Panel A shows the normal physical structure of flagella expressed by UPEC 5011 in suspension.

When the pathogen was exposed to a chitosan nanoparticle preparation, no disruption of the normal structure of flagella is observed (Panel B). When the pathogen was exposed to the tannin-chitosan composite nanoparticle material, extensive coating and cross-linking of flagella on multiple cells is seen (Panel C). It was also noted that this interaction created numerous aggregates of UPEC. Panel D is a scanning electron micrograph of the tannin-chitosan composite nanoparticle alone. These results indicate that the cranberry tannin-chitosan composite materials physically coat the flagella of UPEC, which in turn prevents invasion of the intestinal epithelial cell.

Data has also been obtained indicating that composites can affect bacterial fimbriae, thereby restricting bacterial locomotion by physically preventing the flagella from providing motion. Tannin-chitosan composites can also affect cell membrane integrity by inhibiting the production and expression of lipopolysaccharides.

Protocol for Preparation of CaCo2 Cells and *E. coli* Strain 5011 for Scanning Electron Microscopy.

Bacterial and Cell Preparation.

CaCo2 cells were cultured according to standard laboratory protocol. Sterile cover slips were placed into 12 wells of a 24-well plate. CaCo2 cells were seeded in each well 10 days before the experiment. Medium was changed every 48 hours. Three days prior to the experiment a static, aerobic culture of *E. coli* (strain 5011) was grown at 37° C. in 40 mL of Tryptose broth for 48 hours. One milliliter of bacteria was passed from the top of the broth into 40 mL of Tryptose broth and incubated overnight under the above conditions.

Day of Experiment.

The overnight bacterial culture was centrifuged at 1840×g for 10 minutes, washed twice in PBS, and was re-suspended in a final volume of 1 mL PBS. The optical density at 450 nm of a $\frac{1}{100}$ dilution of the bacterial suspension was determined, then compared to a previously generated growth curve. CaCo2 cells were washed twice with PBS.

Bacteria were used at a multiplicity of infection (MOI) of 100. Bacteria and cranberry products were mixed in a 15 mL conical tube and allowed to incubate at room temperature for 5 minutes. Cell culture medium was added to the bacteria and cranberry products, and divided amongst the appropriate wells of CaCo2 cells, if applicable. Cells are incubated for 1 hour at 37° C. (no $CO_2$ or humidity control), then washed once in PBS. Cell culture medium plus Gentamicin sulfate (100 m/mL final concentration) was added to the plate incubated for 1 hour at 37° C. (no $CO_2$ or humidity control). Cells were washed three times in PBS before SEM preparation.

SEM Preparation.

Cells were fixed in the 24-well plate overnight at 4° C. using a 2% Gluteraldehyde solution in 0.1M Phosphate buffer. Cells were washed in 0.1M phosphate buffer for 10 minutes. Cover slips were removed from the wells and stacked into a holder with washers between the cover slips to preserve the surface. Cells were washed again in the holder with 0.1M phosphate buffer for 10 minutes. Cells were subsequently washed in increasing concentrations of ethanol for 10 minutes each, according to the following sequence:

| Percent EtOH | Time (minutes) |
| --- | --- |
| 30 | 10 |
| 50 | 10 |
| 70 | 10 |
| 80 | 10 |
| 90 | 10 |
| 95 | 10 |
| 100 | 10 |
| 100 | 10 |
| Siv-dried | 10 |

The holder was placed in the critical point dryer chamber with ethanol. The dryer was cooled to 10° C. using $CO_2$. The ethanol was purged and replaced with $CO_2$, then incubated for 10 minutes. Two additional purges and incubations were performed. The chamber was then heated to 35° C.-42° C., increasing the pressure on the samples. The pressure was then slowly decreased (~100 psi/min) until reaching 0 psi. Samples were removed from the holder and placed in a desiccator until coated and observed on a scanning electron microscope.

Materials.
Tryptose Broth Recipe:
    10 g Tryptose (Fisher #211713);
    2.5 g NaCl (Fisher #BP358-212);
    0.5 g Dextrose (Fisher #215530);
    0.0025 g Thiamine Hydrochloride (Sigma #T4625-10 g).
Autoclave on the liquid cycle at 121° C. and 15 psi; no dry time.
Experimental Cell Culture Medium:
    RPMI-1640 (Fisher #SH30255.FS);
    Fetal Bovine Serum (Fisher #SH3007003). FBS is 5% total medium (v/v).
CaCo2 Standard Protocol Cell Culture Medium:
    DMEM (Fisher #BW12614F);
    Fetal Bovine Serum (Fisher #SH3007003). FBS is 10% total medium (v/v);
    Penicillin/Streptomycin Mix (Fisher #AT35712). Pen/Strep is 1% total medium (v/v);
    Nonessential Amino Acids (NEAA; Fisher #13-114E); NEAA is 1% total medium (v/v);
    Gluta-MAX (L-alanyl-L-glutamine, Invitrogen #35050-061). Gluta-MAX is 1% of the total medium (v/v).

Example 10

Pharmaceutical Dosage Forms

The following formulations illustrates representative pharmaceutical dosages forms that may be used for the therapeutic or prophylactic administration of a tannin-chitosan composition described herein, such as a nanoparticle or liposome (hereinafter referred to as 'Composition X'):

| (i) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Composition X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Composition X' | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Composition X' | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| 'Composition X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A composition comprising a matrix of chitosan and tannins, wherein the tannins comprise one or more oligomeric proanthocyanidins, the chitosan is electrostatically bonded to the one or more oligomeric proanthocyanidins, and the matrix of chitosan and tannins is in the form of a chitosan-tannin composite material, wherein the composition is a hydrogel film, the chitosan-tannin composite material does not include a crosslinking agent, and the tensile strength of the composite material is higher than that of the same hydrogel film containing chitosan but no oligomeric proanthocyanidin.

2. The composition of claim 1 wherein the tensile strength of the composite material is 700 MPa to about 825 MPa.

3. The composition of claim 2 in combination with a wound dressing.

4. The composition of claim 2 in combination with a dermal patch.

5. The composition of claim 2 in combination with a packaging biomaterial.

6. A composition comprising a matrix of chitosan and tannins, wherein the tannins comprise one or more oligomeric proanthocyanidins, the chitosan is electrostatically bonded to the one or more oligomeric proanthocyanidins, and the matrix of chitosan and tannins is in the form of a chitosan-tannin composite material, wherein the composition is in the form of a hydrogel film or a biogel, the chitosan-tannin composite material does not include a crosslinking agent, and the tensile strength of the composite material is about 600 MPa to about 825 MPa.

7. The composition of claim 6 in combination with a wound dressing.

8. The composition of claim 6 in combination with a dermal patch.

9. The composition of claim 6 in combination with a packaging biomaterial.

* * * * *